US008129564B2

(12) United States Patent
Prosch et al.

(10) Patent No.: US 8,129,564 B2
(45) Date of Patent: Mar. 6, 2012

(54) MITIGATING NECROSIS IN TRANSGENIC GLYPHOSATE-TOLERANT COTTON PLANTS TREATED WITH HERBICIDAL GLYPHOSATE FORMULATIONS

(75) Inventors: Stephen D. Prosch, Ballwin, MO (US); Michael E. Seitz, Dublin, CA (US); Eric A. Haupfear, St. Charles, MO (US); Eduardo Casanova, Chesterfield, MO (US); Peter E. Rogers, St. Louis, MO (US); David R. Eaton, St. Louis, MO (US); David Z. Becher, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 538 days.

(21) Appl. No.: 11/368,344

(22) Filed: Mar. 3, 2006

(65) Prior Publication Data
US 2007/0037708 A1    Feb. 15, 2007

Related U.S. Application Data

(60) Provisional application No. 60/713,948, filed on Sep. 1, 2005, provisional application No. 60/659,001, filed on Mar. 4, 2005.

(51) Int. Cl.
*C07F 9/22* (2006.01)
*C07C 205/00* (2006.01)
*A01N 57/00* (2006.01)

(52) U.S. Cl. ............................ 562/11; 562/553; 504/127

(58) Field of Classification Search ........................ None
See application file for complete search history.

(56) References Cited

U.S. PATENT DOCUMENTS

| 3,455,675 | A | | 7/1969 | Irani |
| 3,556,762 | A | | 1/1971 | Hamm |
| 3,853,530 | A | | 12/1974 | Franz |
| 4,486,359 | A | | 12/1984 | Brendel Nee Hajnoczki et al. |
| 4,535,060 | A | * | 8/1985 | Comai ..................... 435/252.33 |
| 4,624,937 | A | | 11/1986 | Chou |
| 5,087,740 | A | | 2/1992 | Smith |
| 5,094,945 | A | * | 3/1992 | Comai ............................. 435/6 |
| 5,317,003 | A | | 5/1994 | Kassebaum et al. |
| 5,463,175 | A | | 10/1995 | Barry et al. |
| 5,464,807 | A | | 11/1995 | Claude et al. |
| 5,633,435 | A | * | 5/1997 | Barry et al. ................... 800/288 |
| 5,668,085 | A | | 9/1997 | Forbes et al. |
| 5,750,468 | A | | 5/1998 | Wright et al. |

(Continued)

FOREIGN PATENT DOCUMENTS
EP         0274369 A1    7/1988
(Continued)

OTHER PUBLICATIONS

Jones et al., Journal of Cotton Science 3:19-26 (1999.*
(Continued)

*Primary Examiner* — Karl J Puttlitz
(74) *Attorney, Agent, or Firm* — Senniger Powers LLP; Joseph A. Schaper

(57) ABSTRACT

This invention relates generally to improved methods and herbicidal glyphosate compositions for use in controlling the growth of weeds and unwanted vegetation, and particularly for use in controlling weeds in a crop of transgenic glyphosate-tolerant cotton plants by over-the-top, foliar application of a herbicidal glyphosate formulation.

39 Claims, 11 Drawing Sheets

U.S. PATENT DOCUMENTS

| | | | |
|---|---|---|---|
| 6,040,497 A * | 3/2000 | Spencer et al. | 800/288 |
| 6,083,878 A | 7/2000 | Brants et al. | |
| 6,417,133 B1 | 7/2002 | Ebner et al. | |
| 6,448,476 B1 | 9/2002 | Barry | |
| 6,586,621 B2 | 7/2003 | Leiber et al. | |
| 6,603,039 B1 | 8/2003 | Ebner et al. | |
| 6,740,488 B2 * | 5/2004 | Rangwala et al. | 435/6 |
| 6,956,005 B2 | 10/2005 | Leiber | |
| 6,963,009 B2 | 11/2005 | Leiber et al. | |
| 7,049,270 B2 * | 5/2006 | Lennon et al. | 504/206 |
| 2001/0051591 A1 * | 12/2001 | Ferrett et al. | 504/103 |
| 2002/0068836 A1 | 6/2002 | Haupfear et al. | |
| 2003/0104943 A1 | 6/2003 | Lennon et al. | |
| 2004/0010160 A1 | 1/2004 | Coleman et al. | |
| 2005/0059840 A1 | 3/2005 | Haupfear et al. | |
| 2005/0223425 A1 * | 10/2005 | Clinton et al. | 800/279 |
| 2005/0261130 A1 * | 11/2005 | Lennon et al. | 504/206 |
| 2006/0020143 A1 | 1/2006 | Leiber | |
| 2006/0106248 A1 | 5/2006 | Scaia et al. | |
| 2006/0229466 A1 | 10/2006 | Arhancet et al. | |
| 2007/0037708 A1 | 2/2007 | Prosch et al. | |
| 2009/0011515 A1 | 1/2009 | Soleta et al. | |

FOREIGN PATENT DOCUMENTS

| | | | |
|---|---|---|---|
| JP | 09227583 | | 9/1997 |
| WO | 9533379 A2 | | 12/1995 |
| WO | 0015037 | * | 3/2000 |
| WO | 0015037 A1 | | 3/2000 |
| WO | 02/36782 A2 | | 5/2002 |
| WO | 0236782 A2 | | 5/2002 |
| WO | 03/092360 A2 | | 11/2003 |
| WO | 03092360 A2 | | 11/2003 |
| WO | 2004072235 A2 | | 8/2004 |
| WO | 2005012515 A2 | | 2/2005 |
| WO | 2005016519 A1 | | 2/2005 |
| WO | 2006096617 A2 | | 9/2006 |

OTHER PUBLICATIONS

Ambrus, et al., "Significance of Impurities in the Safety Evaluation of Crop Protection Products," Pure Appl. Chem., 2003, 75(7):937-973.

Herbicide Handbook, William K. Vencill ed., Weed Science Society of America, 8th Ed., 2002, pp. 69 and 329-330.

Adu-Tutu, K.O., et al., "Reduced Tillage and Crop Residue Effects on Cotton Weed Control, Growth and Yield," Arizona Cotton Report (P-138) May 2004, pp. 237-261.

McCloskey, W.B., et al., "Roundup Ready Flex Cotton: Glyphosate Tolerance and Weed Management 2002-2003," Arizona Cotton Report (P-138) May 2004, pp. 227-236.

* cited by examiner

US 8,129,564 B2

MITIGATING NECROSIS IN TRANSGENIC GLYPHOSATE-TOLERANT COTTON PLANTS TREATED WITH HERBICIDAL GLYPHOSATE FORMULATIONS

This application claims the benefit of U.S. provisional application Ser. No. 60/659,001, filed Mar. 4, 2005 and U.S. provisional application Ser. No. 60/713,948, filed Sep. 1, 2005, the entire contents of which are incorporated herein by reference.

BACKGROUND OF THE INVENTION

This invention relates generally to improved methods for controlling weeds in a crop of transgenic glyphosate-tolerant cotton plants by over-the-top, foliar application of a herbicidal glyphosate formulation. The present invention is further directed to herbicidal glyphosate compositions useful in practicing the weed control methods disclosed herein.

Cotton (i.e., Gossypium hirsutum) provides an ideal fiber for textile manufacture as well as oil for human consumption, feed for livestock and base chemicals for a variety of industrial products. Cotton production is well-established in the United States and many other areas of the world. As in other cultivated crops, weeds can cause significant yield losses and require careful management by the grower as they interfere through their competition for available resources including water, nutrients and light. In cotton, weeds can also impede harvest and have a negative economic impact on the grower by not only reducing cotton lint yields, but also lint quality. Weed control practices in cotton have included cultural, mechanical, biological and chemical methods. Among these, chemical weed control has been widely adopted along with the use of tillage (e.g., seed bed preparation, tillage) and cultural (e.g., crop rotation, field selection) methods.

N-(phosphonomethyl)glycine, known in the agricultural chemical art as glyphosate, is a highly effective and commercially important broad spectrum phytotoxicant useful in controlling the growth of germinating seeds, emerging seedlings, maturing and established woody and herbaceous vegetation, and aquatic plants. Glyphosate is used as a post-emergent herbicide to control the growth of a wide variety of annual and perennial grass and broadleaf weed species in cultivated crop lands, including cotton production, and is the active ingredient in the ROUNDUP family of herbicides available from Monsanto Company (Saint Louis, Mo.).

Glyphosate and salts thereof are conveniently applied in aqueous herbicidal formulations, usually containing one or more surfactants, to the foliar tissues (i.e., the leaves or other photosynthesizing organs) of the target plant. After application, the glyphosate is absorbed by the foliar tissues and translocated throughout the plant. Glyphosate noncompetitively blocks an important biochemical pathway that is common to virtually all plants. More specifically, glyphosate inhibits the shikimic acid pathway that leads to the biosynthesis of aromatic amino acids. Glyphosate inhibits the conversion of phosphoenolpyruvic acid and 3-phosphoshikimic acid to 5-enolpyruvyl-3-phosphoshikimic acid by inhibiting the enzyme 5-enolpyruvyl-3-phosphoshikimic acid synthase (EPSP synthase or EPSPS) found in plants.

Advances in genetic engineering have provided the requisite tools to transform cotton and other cultivated plants to contain foreign genes for improvement of certain agronomic traits and the quality of the product. One such trait of particular agronomic and environmental importance is herbicide tolerance, in particular, tolerance to glyphosate herbicide. Glyphosate-resistant or tolerant crop plants may reduce the need for tillage to control weeds, thereby effectively reducing soil erosion. Further, glyphosate-tolerant crop plants provide greater simplicity and flexibility in attaining adequate weed control.

Glyphosate-tolerant cotton can be produced, for example, by introducing into the genome of the plant, the capacity to express various native and variant plant or bacterial EPSPS enzymes that have a lower affinity for glyphosate and therefore retain their catalytic activity in the presence of glyphosate (See, for example, U.S. Pat. Nos. 5,633,435, 5,094,945, 4,535,060, 6,040,497 and 6,740,488). Glyphosate-tolerance has been introduced into cotton plants and is a successful product now widely used in cotton production. The current commercial ROUNDUP READY cotton event designated 1445 available from Monsanto Company provides excellent resistance to glyphosate. Glyphosate is typically applied over-the-top (OTT) of ROUNDUP READY cotton from emergence through the four leaf node stage of development (e.g., at rates of up to about 0.75 pounds glyphosate acid equivalent per acre (lb a.e./A or about 0.84 kg a.e./ha). ROUNDUP READY cotton varieties used in combination with ROUNDUP glyphosate herbicidal formulations have become the standard program for weed management in cotton production in the United States. The primary advantage to growers for using the ROUNDUP READY cotton system is that it allows simple and convenient application of glyphosate, a broad spectrum, post-emergence herbicide, to effectively control weeds and grasses with excellent crop safety and less dependence on pre-plant herbicide applications. Other benefits include a better fit into no-till and reduced tillage systems. ROUNDUP READY cotton has expanded the options for weed management and made the practice of weed control much easier, less expensive and more flexible. Growers have reported making fewer trips across fields to apply herbicides as well as making fewer cultivation trips, which conserves fuel and reduces soil erosion. Glyphosate-tolerant cotton, therefore, decreases the environmental risks posed by herbicides while at the same time increasing the efficacy of necessary chemical weed control.

Although widely accepted as a standard in cotton production, ROUNDUP READY cotton varieties do however impose some limitations on the grower. ROUNDUP READY cotton varieties possess reproductive bodies that are susceptible to glyphosate-mediated injury that may, in some cases, result in delayed maturity or reproductive injury as measured by flower pollen shed, flower drop, boll drop, and/or lint yield loss. Accordingly, in order to avoid or minimize such reproductive injury, over-the-top applications of glyphosate herbicides to cotton plants grown from seed of ROUNDUP READY cotton event 1445 and progeny thereof are generally discontinued from the fifth leaf node stage and beyond (e.g., through layby) and instead glyphosate is usually applied as a post-directed spray between the crop rows during this period of growth in order to minimize contact with the cotton plants. Directed herbicide application requires specialized equipment that is often susceptible to misapplication, must be operated at lower speeds and requires a greater number of trips per acre compared to broadcast applicators.

It is believed that the lack of reproductive glyphosate tolerance that limits later stage foliar application of glyphosate to cotton plants corresponding to ROUNDUP READY cotton event designated 1445 is the result of insufficient CP4 EPSPS expression in critical tissues, higher sensitivity of these tissues to glyphosate, and accumulation of high amounts of glyphosate in those strong sink tissues. Recently, as disclosed in International Publication No. WO 2004/072235, Monsanto Company has developed a new glyphosate-tolerant cotton event (designated MON 88913, to be commercially named ROUNDUP READY FLEX cotton and having seed deposited with American Type Culture Collection with Accession No. PTA-4854) to provide cotton growers with an improved product for management of economically damaging weeds. ROUNDUP READY FLEX cotton provides an increased margin of fruit retention and crop safety, due to increased tolerance to glyphosate in reproductive tissues. This allows for an expanded window for over-the-top ground application of glyphosate agricultural herbicides (e.g., at rates of up to about 1.125 pounds glyphosate acid equivalent per acre (lb a.e./A or about 1.26 kg a.e./ha) extending from cotton emergence up to layby, the critical timing for weed control in cotton. Through these enhanced treatment opportunities, the grower can more effectively manage weed control in cotton using over-the-top herbicide applications as compared to post-directed or hooded-sprayer applications.

Despite the widely-recognized advantages in weed control provided by ROUNDUP READY and ROUNDUP READY FLEX cotton, it has been observed that these transgenic cotton varieties, under certain environmental conditions, exhibit a susceptibility to leaf tissue necrosis following over-the-top application of glyphosate herbicides. In the case of over-the-top application of glyphosate herbicides to ROUNDUP READY FLEX cotton at later stages of plant development, the appearance of necrotic lesions on the treated cotton plants may appear to be more pronounced due to the more fully developed canopy and greater available leaf area. This phenomenon is rare and such leaf injury, if it is encountered at all, is generally limited with little or no further expression of injury and the cotton plants recover with essentially no yield loss or deleterious effect on fertility under standard or recommended ROUNDUP treatment protocols. In particular, the cotton apical growing point and subsequent leaves appear unaffected.

Accordingly, there exists a need for methods and herbicidal glyphosate formulations useful for over-the-top, foliar application to transgenic glyphosate-tolerant cotton plants that are effective in weed control and consistently avoid inducing significant leaf necrosis in the treated plants in the variable environmental conditions that may be encountered during the growing season.

SUMMARY OF THE INVENTION

As discussed in detail below, in accordance with the present invention, it has been discovered that the leaf necrosis phenomenon sometimes observed in transgenic glyphosate-tolerant cotton plants following over-the-top application of glyphosate herbicides and under certain growing conditions is induced, at least in part, by N-(phosphonomethyl)iminodiacetic acid (PMIDA) and/or salts thereof which are often present at relatively low concentrations in glyphosate herbicidal formulations. The present invention encompasses various aspects and embodiments directed to strategies for mitigating PMIDA-induced necrosis in transgenic glyphosate-tolerant cotton plants treated with herbicidal glyphosate formulations, including methods of weed control, glyphosate herbicidal compositions and formulations for use in the practice of such weed control methods as well as methods of manufacturing technical grade glyphosate product for use in preparing such glyphosate herbicidal compositions and formulations. Although the present invention has specific application in mitigating PMIDA-induced necrosis in transgenic glyphosate-tolerant cotton plants, many aspects and embodiments of the invention disclosed herein have wider application.

Accordingly, in various embodiments, methods are provided for selectively controlling weeds in a field containing a crop of transgenic glyphosate-tolerant cotton plants. The methods comprise applying a sufficient amount of a herbicidal glyphosate formulation comprising N-(phosphonomethyl)glycine or an agronomically acceptable salt thereof to the crop foliage and weeds to control growth of the weeds. In some embodiments, the crop of transgenic glyphosate-tolerant cotton plants have increased glyphosate tolerance in vegetative and reproductive tissues such that application of the herbicidal glyphosate formulation when at least five leaf nodes are present on a cotton plant of the crop does not incur significant glyphosate-mediated reproductive injury to the plant. In one embodiment, the concentration of N-(phosphonomethyl)iminodiacetic acid and salts thereof present in the glyphosate formulation and the application rate of the herbicidal glyphosate formulation are controlled so as to not induce significant leaf necrosis in the cotton plants.

In another embodiment, the glyphosate formulation comprises N-(phosphonomethyl)iminodiacetic acid or salt thereof and a safening agent in a concentration sufficient to inhibit significant leaf necrosis in the crop induced by N-(phosphonomethyl)iminodiacetic acid or salt thereof present in the glyphosate formulation.

In another embodiment, the herbicidal glyphosate formulation applied to the crop of transgenic glyphosate-tolerant cotton plants comprises N-(phosphonomethyl)iminodiacetic acid or salt thereof and an adjuvant other than an alkoxylated alkylamine. The adjuvant is present in an amount effective to decrease cell membrane permeability within the crop to decrease cellular uptake of the N-(phosphonomethyl)iminodiacetic acid or salt thereof in the crop treated with the formulation as compared to crops treated with an application mixture having the same composition as the formulation except that an alkoxylated alkylamine is substituted for the adjuvant.

Alternatively, the herbicidal glyphosate formulation comprises N-(phosphonomethyl)glycine, predominantly in the form of an agronomically acceptable salt thereof selected from the group consisting of alkali metal salts, alkylamine salts and alkanolamine salts of N-(phosphonomethyl)glycine, N-(phosphonomethyl)iminodiacetic acid or salt thereof and a safening agent comprising an adjuvant. The concentration of the adjuvant in the herbicidal glyphosate formulation is selected such that the rate of transfer of N-(phosphonomethyl)iminodiacetic acid or salt thereof into the foliar tissues of the crop of transgenic glyphosate-tolerant cotton plants is sufficiently slow to inhibit significant leaf necrosis in the crop induced by N-(phosphonomethyl)iminodiacetic acid or salt thereof present in the glyphosate formulation.

The present invention further provides herbicidal glyphosate compositions (e.g., spray solutions, tank mixes and concentrates) useful for killing or controlling the growth of weeds in a field containing a crop of transgenic glyphosate-tolerant cotton plants as well as in other weed control applications. In one embodiment, the composition comprises N-(phosphonomethyl)glycine or an agronomically acceptable salt thereof, N-(phosphonomethyl)iminodiacetic acid or salt thereof, and a safening agent in a concentration sufficient to inhibit significant leaf necrosis in the crop induced by N-(phosphonomethyl)iminodiacetic acid or salt thereof present in the glyphosate composition. Suitable safening agents may be selected from the group consisting of metal ions, antioxidants, humectants, light absorbing compounds, and mixtures thereof.

In another embodiment, the aqueous herbicidal concentrate composition comprises at least about 360 grams per liter (on an acid equivalent basis) of N-(phosphonomethyl)glycine or an agronomically acceptable salt thereof and less than 5 grams per liter (on an acid equivalent basis) of N-(phosphonomethyl)iminodiacetic acid or salt thereof. The composition further comprises aminomethylphosphonic acid and the weight ratio of N-(phosphonomethyl)iminodiacetic acid or a salt thereof to aminomethylphosphonic acid is not more than 0.25:1; or the composition further comprises at least one surfactant other than an alkoxylated alkyl amine or an alkoxylated phosphate ester; or the N-(phosphonomethyl)glycine is present predominantly in the form of the potassium, dipotassium, monoammonium, diammonium, sodium, monoethanolamine, n-propylamine, ethylamine, ethylenediamine, hexamethylenediamine or trimethylsulfonium salt thereof; or the composition further comprises a surfactant component comprising an alkoxylated alkylamine and an alkoxylated phosphate ester; or the N-(phosphonomethyl)glycine is present predominantly in the form of the isopropylamine salt thereof.

In another embodiment, the herbicidal glyphosate composition comprises N-(phosphonomethyl)glycine predominantly in the form of an agronomically acceptable salt thereof selected from the group consisting of alkali metal salts, alkylamine salts and alkanolamine salts of N-(phosphonomethyl)glycine; N-(phosphonomethyl)iminodiacetic acid or salt thereof; and a safening agent comprising an adjuvant in a concentration selected such that the rate of transfer of N-(phosphonomethyl)iminodiacetic acid or salt thereof into the foliar tissues of the crop of transgenic glyphosate-tolerant cotton plants is sufficiently slow to inhibit significant leaf necrosis in the crop induced by N-(phosphonomethyl)iminodiacetic acid or salt thereof present in the glyphosate formulation.

In another embodiment, the aqueous concentrate herbicidal glyphosate composition comprises N-(phosphonomethyl)glycine or an agronomically acceptable salt thereof, the concentration of the N-(phosphonomethyl)glycine or an agronomically acceptable salt thereof being at least about 360 or more grams per liter on an acid equivalent basis; N-(phosphonomethyl)iminodiacetic acid or salt thereof; a metal ion safening agent that is subject to formation of a complex or salt with N-(phosphonomethyl)iminodiacetic acid or an anion formed by deprotonation or partial deprotonation thereof, wherein the molar ratio of metal ions to N-(phosphonomethyl)iminodiacetic acid equivalent is at least about 0.4:1; and a surfactant component comprising at least one cationic surfactant.

In another embodiment, the aqueous concentrate herbicidal glyphosate composition comprises at least about 360 grams per liter (on an acid equivalent basis) of N-(phosphonomethyl)glycine or an agronomically acceptable salt thereof; less than 5 grams per liter (on an acid equivalent basis) of N-(phosphonomethyl)iminodiacetic acid or salt thereof; and aminomethylphosphonic acid (acid equivalent), wherein the weight ratio of N-(phosphonomethyl)iminodiacetic acid or a salt thereof to aminomethylphosphonic acid is not more than 0.25:1.

In another embodiment, the aqueous concentrate herbicidal glyphosate composition comprises at least about 360 grams per liter (on an acid equivalent basis) of N-(phosphonomethyl)glycine or an agronomically acceptable salt thereof, less than about 5 grams per liter (on an acid equivalent basis) of N-(phosphonomethyl)iminodiacetic acid or salt thereof, and at least one surfactant other than an alkoxylated alkyl amine or an alkoxylated phosphate ester.

In another embodiment, the aqueous concentrate herbicidal glyphosate composition comprises at least about 360 grams per liter (on an acid equivalent basis) of N-(phosphonomethyl)glycine predominantly in the form of the potassium, dipotassium, monoammonium, diammonium, sodium, monoethanolamine, n-propylamine, ethylamine, ethylenediamine, hexamethylenediamine or trimethylsulfonium salt thereof, and less than about 5 grams per liter (on an acid equivalent basis) of N-(phosphonomethyl)iminodiacetic acid or salt thereof.

In another embodiment, the aqueous concentrate herbicidal glyphosate composition comprises at least about 360 grams per liter (on an acid equivalent basis) of N-(phosphonomethyl)glycine or an agronomically acceptable salt thereof, less than about 5 grams per liter (on an acid equivalent basis) of N-(phosphonomethyl)iminodiacetic acid or salt thereof, and at least one surfactant component comprising an alkoxylated alkyl amine or an alkoxylated phosphate ester.

In another embodiment, the aqueous concentrate herbicidal glyphosate composition comprises at least about 360 grams per liter (on an acid equivalent basis) of N-(phosphonomethyl)glycine predominantly in the form of the isopropylamine salt thereof, and less than about 5 grams per liter (on an acid equivalent basis) of N-(phosphonomethyl)iminodiacetic acid or salt thereof.

In another embodiment, the aqueous concentrate herbicidal glyphosate composition comprises at least about 360 grams per liter (on an acid equivalent basis) of N-(phosphonomethyl)glycine or an agronomically acceptable salt thereof; less than 0.45 wt. % of N-(phosphonomethyl)iminodiacetic acid or salt thereof (acid equivalent) on a glyphosate, acid equivalent (a.e.), basis; and aminomethylphosphonic acid, wherein the weight ratio of N-(phosphonomethyl)iminodiacetic acid or a salt thereof (acid equivalent) to aminomethylphosphonic acid (acid equivalent) is not more than 0.25:1.

In another embodiment, the aqueous concentrate herbicidal glyphosate composition comprises at least about 360 grams per liter (on an acid equivalent basis) of N-(phosphonomethyl)glycine or an agronomically acceptable salt thereof, less than about 0.45 wt. % of N-(phosphonomethyl)iminodiacetic acid or salt thereof (acid equivalent) on an N-(phosphonomethyl)glycine, a.e., basis, and at least one surfactant other than an alkoxylated alkyl amine or an alkoxylated phosphate ester.

In another embodiment, the aqueous concentrate herbicidal glyphosate composition comprises at least about 360 grams per liter (on an acid equivalent basis) of N-(phosphonomethyl)glycine predominantly in the form of the potassium, dipotassium, monoammonium, diammonium, sodium, monoethanolamine, n-propylamine, ethylamine, ethylenediamine, hexamethylenediamine or trimethylsulfonium salt thereof, and less than about 0.45 wt. % (phosphonomethyl)iminodiacetic acid or salt thereof (acid equivalent) on an N-(phosphonomethyl)glycine, a.e., basis.

In another embodiment, the aqueous concentrate herbicidal glyphosate composition comprises at least about 360 grams per liter (on an acid equivalent basis) of N-(phosphonomethyl)glycine or an agronomically acceptable salt thereof, less than about 0.45 wt. % N-(phosphonomethyl)iminodiacetic acid or salt thereof on an N-(phosphonomethyl)glycine basis, and at least one surfactant component comprising an alkoxylated alkyl amine or an alkoxylated phosphate ester.

In another embodiment, the aqueous concentrate herbicidal glyphosate composition comprises at least about 360 grams per liter (on an acid equivalent basis) of N-(phosphonomethyl)glycine predominantly in the form of the isopropylamine salt thereof, and less than about 0.45 wt. % N-(phosphonomethyl)iminodiacetic acid or salt thereof (acid equivalent) on an N-(phosphonomethyl)glycine, a.e., basis.

In a further embodiment, the aqueous concentrate herbicidal glyphosate composition comprises at least about 360 grams per liter (on an acid equivalent basis) of N-(phosphonomethyl)glycine predominantly in the form of a salt thereof, less than about 0.45 wt. % N-(phosphonomethyl)iminodiacetic acid or salt (acid equivalent), and at least about 0.02 wt. % glycine or a salt thereof (acid equivalent), the weight percentages being on an acid equivalent basis relative to N-(phosphonomethyl)glycine, a.e.

In a still further embodiment, the aqueous concentrate herbicidal glyphosate composition comprises at least about 360 grams per liter (on an acid equivalent basis) of N-(phosphonomethyl)glycine predominantly in the form of a salt thereof, the preparation of the composition comprising hydrolyzing a dialkyl phosphonate intermediate, the intermediate comprising a carboxylic acid salt of dialkyl N-(phosphonomethyl) glycine or otherwise derived from reaction of a dialkylphosphite with N-methylolglycine.

The present invention also provides various technical grade glyphosate compositions useful in the preparation of herbicidal glyphosate compositions and formulations. In one embodiment the technical grade glyphosate composition comprises, on a dry basis, at least 95 wt. % N-(phosphonomethyl)glycine acid equivalent, less than 0.15 wt. % N-(phosphonomethyl)iminodiacetic acid or a salt thereof, and a byproduct selected from not more than 0.7 wt. % N-formyl-N-(phosphonomethyl)glycine or not more than 0.03 wt. % N-methyliminodiacetic acid.

In accordance with another embodiment, the technical grade glyphosate composition comprises at least 90 wt. % N-(phosphonomethyl)glycine acid equivalent, less than 0.6 wt. % N-(phosphonomethyl)iminodiacetic acid or a salt thereof, and aminomethylphosphonic acid, wherein the weight ratio of N-(phosphonomethyl)iminodiacetic acid or a salt thereof to aminomethylphosphonic acid is not more than 0.25:1, the weight percentages being on a dry basis.

In accordance with another embodiment, the technical grade glyphosate composition comprises at least 90 wt. % N-(phosphonomethyl)glycine acid or salt thereof, less than 0.45 wt. % N-(phosphonomethyl)iminodiacetic acid or a salt thereof, and at least 0.02 wt. % glycine or salt thereof, the weight percentages being on a dry acid equivalent basis.

In accordance with a further embodiment, the technical glyphosate composition comprises at least 90 wt. % N-(phosphonomethyl)glycine acid equivalent, between about 0.02 wt. % and about 0.25 wt. % N-(phosphonomethyl)iminodiacetic acid or a salt thereof, and a byproduct selected from not more than 0.6 wt. % N-formyl-N-(phosphonomethyl)glycine, the weight percentages being on a dry acid equivalent basis.

In another embodiment, the glyphosate product is selected from the group consisting of a technical grade glyphosate composition comprising at least about 90 wt. % glyphosate acid and a concentrated aqueous solution comprising at least about 360 grams per liter a.e. of an agronomically acceptable salt of glyphosate. The composition comprises less than about 0.45 wt. % N-(phosphonomethyl)iminodiacetic acid or a salt thereof (acid equivalent), and between about 0.05 and about 2 wt. % glyphosine or a salt thereof (acid equivalent), on a glyphosate, a.e., basis.

The present invention also provides various processes for the preparation of glyphosate by oxidation of N-(phosphonomethyl)iminodiacetic acid wherein the glyphosate product has a low N-(phosphonomethyl)iminodiacetic acid content. In one embodiment, the process comprises contacting an aqueous reaction medium containing N-(phosphonomethyl)iminodiacetic acid with a gas comprising molecular oxygen in the presence of a catalyst for the oxidation; recovering a glyphosate product from glyphosate obtained in the resulting product reaction solution, the recovery of the glyphosate product comprising separating such product from an aqueous mixture wherein the ratio of total N-(phosphonomethyl)iminodiacetic acid content to total glyphosate content is at least 25% greater than the corresponding ratio in the product reaction solution, oxygen having been caused to flow through the aqueous reaction medium in the presence of the catalyst to an extent sufficient to reduce the N-(phosphonomethyl)iminodiacetic acid content of the product reaction solution to a level such that the recovered glyphosate product has an N-(phosphonomethyl)iminodiacetic acid content less than about 600 ppm, basis glyphosate; and removing the glyphosate product from the process.

In another embodiment, the process comprises contacting an aqueous reaction medium containing N-(phosphonomethyl)iminodiacetic acid with a gas comprising molecular oxygen in the presence of a catalyst for the oxidation; recovering a glyphosate product from glyphosate obtained in the resulting product reaction solution, oxygen having been caused to flow through the aqueous reaction medium in the presence of the catalyst to an extent sufficient to reduce the N-(phosphonomethyl)iminodiacetic acid content of the product reaction solution to a level such that the recovered glyphosate product has an N-(phosphonomethyl)iminodiacetic acid content less than about 600 ppm, basis glyphosate; and removing the glyphosate product from the process.

In accordance with another embodiment, the process comprises oxidizing N-(phosphonomethyl)iminodiacetic acid in an aqueous reaction medium to produce a product reaction solution containing glyphosate and unreacted N-(phosphonomethyl)iminodiacetic acid; recovering glyphosate from the product reaction solution in a product form having a N-(phosphonomethyl)iminodiacetic acid content not greater than 600 ppm on a glyphosate basis, the recovery of the product form comprising contacting an aqueous solution comprising the product reaction solution, or a solution comprising N-(phosphonomethyl)iminodiacetic acid derived from the product reaction solution, with an anion exchange resin which has a selective affinity for N-(phosphonomethyl)iminodiacetic acid in preference to glyphosate.

In another embodiment, the process comprises oxidizing N-(phosphonomethyl)iminodiacetic acid in an aqueous reaction medium to produce a product reaction solution containing glyphosate and unreacted N-(phosphonomethyl)iminodiacetic acid; crystallizing glyphosate from a crystallizer feed solution comprising or derived from the product reaction solution; subjecting the resulting slurry of glyphosate crystals in mother liquor to solid/liquid separation; purging a fraction of the mother liquor for removal of N-(phosphonomethyl) iminodiacetic acid from the process; and recycling another fraction of the mother liquor to a crystallizer in which glyphosate is crystallized from the feed solution, the volume of the purge fraction relative to the volume of the recycle fraction being sufficient that the solid glyphosate crystals separated in the solid/liquid separation step have an N-(phosphonomethyl)iminodiacetic acid content lower than 600 ppm or can be contacted with an aqueous wash medium to produce a solid glyphosate product having such lower N-(phosphonomethyl)iminodiacetic acid content.

In a further embodiment, the process comprises contacting an aqueous medium containing N-phosphonomethyl-iminodiacetic acid in a primary reaction system with a gas comprising molecular oxygen in the presence of a particulate catalyst for the oxidation to produce a product slurry comprising a product reaction solution comprising glyphosate and unreacted N-(phosphonomethyl)iminodiacetic acid, and having the particulate catalyst suspended therein; separating the catalyst from the reaction product solution to produce a filtered product reaction solution; and contacting an aqueous solution comprising the filtered product reaction solution, or derived therefrom, with an oxidizing agent in a polishing reaction zone for further conversion of N-phosphonomethyl-iminodiacetic acid to glyphosate.

In a further embodiment, the process comprises contacting an aqueous reaction medium containing N-(phosphonomethyl)iminodiacetic acid with a gas comprising molecular oxygen in the presence of a noble metal on carbon catalyst, and in the absence of a concentration of a non-noble metal promoter that would be effective to either retard the oxidation of N-(phosphonomethyl)iminodiacetic acid or causes the rate of consumption of oxygen in the oxidation of formaldehyde or formic acid to be materially increased relative to the rate of consumption of oxygen in the oxidation of N-(phosphonomethyl)iminodiacetic acid; and maintaining contact of the reaction medium with gas comprising molecular oxygen for a time sufficient to reduce the N-(phosphonomethyl)iminodiacetic acid content of the resulting product reaction solution to not greater than 250 ppm.

In a further embodiment, the process comprises oxidizing N-(phosphonomethyl)iminodiacetic acid in an aqueous reaction medium to produce a product reaction solution containing glyphosate and unreacted N-(phosphonomethyl)iminodiacetic acid; transferring the product reaction solution to a product recovery process by which a plurality of glyphosate products are produced; and operating the product recovery process to produce at least two separate glyphosate salt products of differing N-(phosphonomethyl)iminodiacetic acid content, wherein the glyphosate basis N-(phosphonomethyl)iminodiacetic acid content of one of the products is less than about 1000 ppm one at least 25% lower than the N-(phosphonomethyl)iminodiacetic acid content of another of the plurality of glyphosate products.

In a still further embodiment, the process comprises contacting N-(phosphonomethyl)iminodiacetic acid with an oxidizing agent in an aqueous reaction medium within an oxidation reaction zone in the presence of a catalyst for the oxidation, thereby effecting oxidation of N-(phosphonomethyl)iminodiacetic acid and producing a reaction solution comprising glyphosate or another intermediate which can be converted to glyphosate; and further processing the reaction solution to produce a glyphosate product containing not more than about 600 ppm N-(phosphonomethyl)iminodiacetic acid or salt thereof, the oxidation of N-(phosphonomethyl)iminodiacetic acid in the aqueous reaction medium being continued until the concentration of N-(phosphonomethyl)iminodiacetic acid in the reaction medium has been reduced to a terminal concentration such that the further processing yields a not greater than about 600 ppm, basis glyphosate.

The present invention further provides a programmed control scheme for use in conjunction with the various processes for the preparation of glyphosate by oxidation of N-(phosphonomethyl)iminodiacetic acid. Such processes further comprise measuring select process variables which affect the N-(methylphosphonic)iminodiacetic acid content of one or more glyphosate products as produced by the process; controlling the select process variables via automated control loops to conform to set points respectively established in the control loops; transmitting signals to the programmed controller conveying the values of the measurements and the set points; computing adjustments to the set points in response to the signals in accordance with an algorithm inscribed in software with which the controller is programmed; and transmitting signals from the programmed controller to the control loops for adjustment of the set point to conform operation of the process to the algorithm.

The present invention further provides a process for the preparation of an aqueous herbicidal concentrate composition comprising at least about 360 grams per liter (on an acid equivalent basis) of N-(phosphonomethyl)glycine predominantly in the form of a salt thereof. The process comprises hydrolyzing a dialkyl intermediate comprising dialkyl N-(phosphonomethyl)glycine, a carboxylate salt of dialkyl N-(phosphonomethyl)glycine or other ester intermediate produced by reaction of a dialkyl phosphite with N-methylolglycine, to yield a solution comprising glyphosate or an agronomically acceptable salt of glyphosate; and recovering solid glyphosate acid or an aqueous concentrate comprising an agronomically acceptable salt of glyphosate in a concentration of at least about 360 grams per liter a.e.

The present invention further provides a method of supplying a glyphosate product for applications in which it is desirable to maintain the N-(phosphonomethyl)iminodiacetic acid content of the product at consistently less than about 0.06 wt. % on a glyphosate basis. The method comprises producing glyphosate in a manufacturing facility, the production of glyphosate in such facility comprising catalytic oxidation of N-(phosphonomethyl)iminodiacetic acid in an aqueous medium in the presence of a catalyst for the oxidation; during designated operations within the facility, conducting the process under conditions effective to consistently produce a glyphosate product having an N-(phosphonomethyl)iminodiacetic acid content less than about 0.06 wt. %, basis glyphosate; and segregating the glyphosate produced during the designated operations from other glyphosate product produced during other operations wherein the other glyphosate product has an N-(phosphonomethyl)iminodiacetic acid content greater than about 0.06 wt. %, basis glyphosate.

In a further aspect of the invention, a method for screening a herbicidal glyphosate formulation for use in foliar application to a crop of transgenic glyphosate-tolerant plants subject to leaf necrosis caused by N-(phosphonomethyl)iminodiacetic acid or a salt thereof present in herbicidal glyphosate formulations is provided. The method comprises (a) growing a plant of the crop until a predetermined developmental age or for a predetermined interval of time; (b) applying the herbicidal glyphosate formulation comprising N-(phosphonomethyl)glycine or a salt thereof to the plant; (c) maintaining the treated plant for a predetermined interval of time under predetermined temperature and humidity conditions selected to illicit a leaf necrosis injury response in the plant caused by N-(phosphonomethyl)iminodiacetic acid or a salt thereof present in the herbicidal glyphosate formulation; and (d) determining extent of leaf necrosis injury to the plant.

Further aspects and embodiments of the invention are described in the following specification and detailed in the claims set forth below.

DETAILED DESCRIPTION OF THE INVENTION

Figure 1:
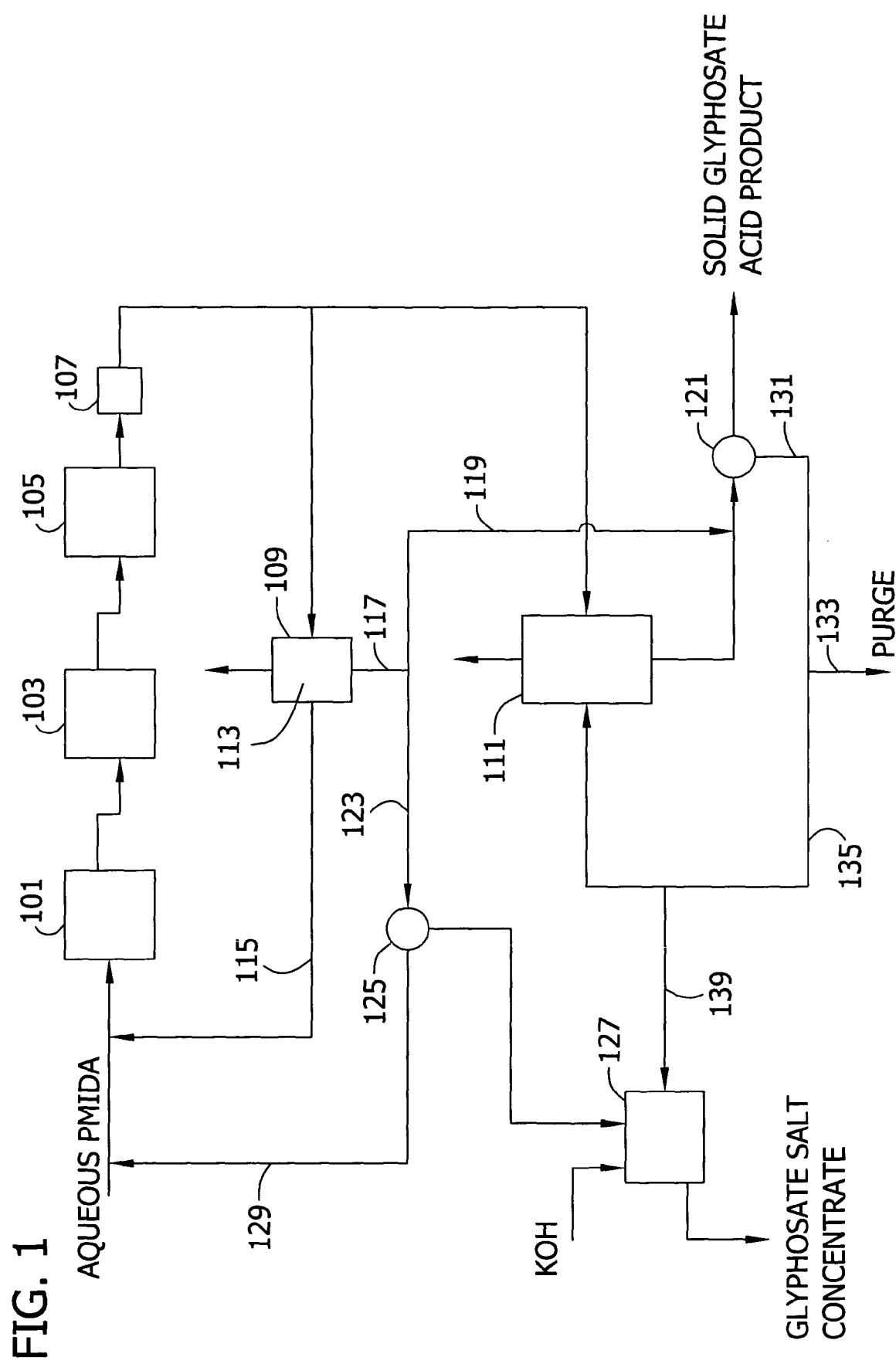
FIG. 1 is a schematic flow sheet illustrating a continuous process for the manufacture of glyphosate from N-(phosphonomethyl)iminodiacetic acid, in which the modifications of the present invention for production of a low N-(phosphonomethyl)iminodiacetic acid content glyphosate product may be implemented.

In accordance with the present invention, it has been discovered that the leaf necrosis phenomenon sometimes observed in transgenic glyphosate-tolerant cotton plants following over-the-top application of glyphosate herbicides and under certain growing conditions is induced, at least in part, by N-(phosphonomethyl)iminodiacetic acid (PMIDA) and/or salts thereof which are often present at relatively low concentrations in glyphosate herbicidal formulations. One conventional method of glyphosate manufacture, discussed in greater detail below, includes liquid phase catalytic oxidative cleavage of a carboxymethyl substituent from PMIDA (formula (1)) to produce N-(phosphonomethyl)glycine (formula (2)) in accordance with the following reaction:

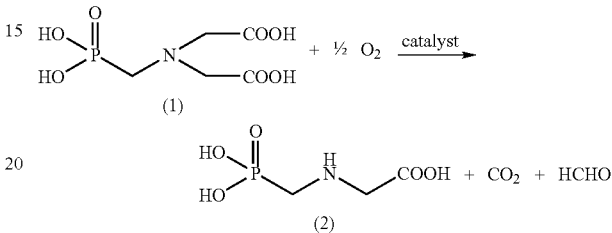

Under commercial scale conditions, high conversion of the PMIDA to the N-(phosphonomethyl)glycine product is readily attained. However, low concentrations (e.g., from about 0.15% to about 0.6% by weight dry basis) of unreacted PMIDA typically remain in the manufactured technical grade N-(phosphonomethyl)glycine product isolated from the oxidation reaction mixture. Moreover, PMIDA may also be present as a by-product or contaminant in N-(phosphonomethyl)glycine manufactured by other conventional methods known in the art. Residual PMIDA in manufactured N-(phosphonomethyl)glycine products is thus often present in herbicidal glyphosate compositions formulated using these products. Given the relatively limited water solubility of the organic acid N-(phosphonomethyl)glycine, aqueous herbicidal glyphosate compositions are typically formulated using one or more of the more water-soluble and agronomically acceptable salts of glyphosate and, in such cases, the PMIDA is also predominantly present in the composition as the corresponding salt, typically the corresponding mono- or dibasic salt. As used herein, unless the context requires otherwise, the term "PMIDA" includes N-(phosphonomethyl)iminodiacetic acid and/or salts and other derivatives thereof and the term "glyphosate" includes any herbicidally effective form of N-(phosphonomethyl)glycine that results in the production of the glyphosate anion in plants, including glyphosate acid and/or salts or other derivatives thereof.

In most applications, the low levels of PMIDA typically present in glyphosate herbicidal formulations are not a problem. However, as noted above, cotton, including transgenic glyphosate-tolerant cotton varieties, is susceptible under certain growing conditions to development of leaf necrosis induced by the presence of even relatively low levels of PMIDA often found in commercial herbicidal glyphosate formulations. As susceptibility to PMIDA-induced necrosis is common to both glyphosate-tolerant cotton (i.e., transgenic cotton) as well as non-transgenic cotton, it appears that the PMIDA-induced leaf necrosis phenomenon in glyphosate-tolerant cotton is unrelated to the transgene. PMIDA-induced leaf necrosis sometimes observed in transgenic glyphosate-tolerant cotton such as ROUNDUP READY and ROUNDUP READY FLEX cotton varieties is characterized by a rapid onset of symptomology, typically within about 2 days following over-the-top application of glyphosate herbicides. Additional symptom development beyond this period for the most part has not been observed, indicating that this phenomenon is not a systemic effect. Furthermore, symptom expression appears to be light activated.

Without being bound to any particular theory, these observations suggest that PMIDA-induced necrosis may operate through a mechanism similar to that seen with herbicides that function through the inhibition of the protoporphyrinogen-oxidase (PPO) enzyme. PPO is inhibited by a wide range of herbicides, such as, the diphenylethers, oxadiazoles, cyclic imides, phenyl pyrazoles and pyridine derivatives. PMIDA could act through the same mechanism as those herbicides wherein membrane disruption is initiated by the inhibition of PPO in the last stages of chlorophyll and heme biosynthetic pathways leading to a buildup of phytotoxic intermediates such as free radicals resulting in tissue necrosis. More particularly, it is believed that PPO catalyzes the oxidation of protoporphyrinogen IX (PPGIX) to protoporphyrin IX (PPIX). PPO inhibition leads to an accumulation of PPGIX, the first light-absorbing chlorophyll precursor. PPGIX accumulation is apparently transitory as it overflows its normal environment in the thylakoid membrane and oxidizes to PPIX. This oxidation may be catalyzed by a plasmalemma enzyme that has protox activity, but is insensitive to, it is believed, PMIDA. PPIX formed outside its native environment probably is separated from Mg chelatase and other pathway enzymes that normally prevent accumulation of PPIX. Light absorption by PPIX apparently produces triplet state PPIX which interacts with ground state oxygen to form singlet oxygen. Both triplet PPIX and singlet oxygen can abstract a hydrogen from unsaturated lipids, producing a lipid radical and initiating a chain reaction of lipid peroxidation. Lipids and proteins are attacked and oxidized, resulting in loss of chlorophyll and carotenoids and in leaky membranes which allows cells and cell organelles to dry and disintegrate rapidly. Quoting from *Herbicide Handbook* (William K. Vencill ed., Weed Science Society of America, 8th edition, pages 69 and 329-330, (2002)).

The expression of PMIDA-induced leaf necrosis and the severity of the resulting leaf injury are heavily dependent upon the prevailing growing conditions and environmental factors and is generally more severe as the PMIDA concentration in the glyphosate herbicidal composition and application rate increase. More particularly, conditions that favor slow metabolism in the cotton plant or metabolic stress generally following glyphosate application appear to be a key factor contributing to the onset and severity of leaf necrosis. For example, it has been observed that exposure to low temperatures is a contributor to PMIDA-induced leaf damage observed in greenhouse and growth chamber environments. It has been found that glyphosate-tolerant cotton plants experiencing "cool" growing conditions (i.e., maximum temperatures of about 80° F. (27° C.) or less) following foliar application of glyphosate herbicides have significantly increased tendency to exhibit leaf injury as compared to plants experiencing "hot" growing conditions (i.e., maximum temperatures of about 90° F. (32° C.). Cotton plants experiencing maximum temperatures of about 70° F. (21° C.) following glyphosate application showed a similar amount of leaf damage as compared to plants grown at 80° F. It has been further observed that cool growing conditions following glyphosate application produced significantly greater leaf injury than cool growing conditions experienced prior to glyphosate treatment. It is believed that cotton plant metabolism at growing temperatures of at least about 90° F. is sufficient to overcome the effects of PMIDA levels typically present in the glyphosate composition, but at 80° F. and lower maximum growing temperatures, plant metabolism may be too slow to overcome these effects, with resultant leaf damage.

If PMIDA-induced necrosis is observed, injury can range from minor necrotic lesions affecting on average from about 1% to about 5% of the total leaf surface area of the plant to more pronounced necrotic lesions affecting on average about 5%, 10%, 15%, 20%, 25%, 30% or more of the total leaf surface area of the affected plants. Minor necrotic lesions generally appear as multiple, very small, circular shaped and uniformly distributed lesions on the surface of the treated cotton leaf having a diameter of less than about 0.5 cm and may coalesce into larger necrotic lesions in the form of larger circular or irregularly shaped areas or patches on the treated cotton leaf surface having a largest dimension of greater than about 0.5 cm. In severe cases, necrotic lesions can become sufficiently large to result in highly visible leaf damage, or even loss of the affected leaves. PMIDA-induced leaf necrosis or tissue death is visibly distinct from "surfactant burn" such as "window panes" commonly associated with the use of certain surfactants in herbicidal formulations applied to glyphosate-tolerant crops.

In accordance with the present invention, a variety of strategies have been devised to allow for effective weed control in cotton production from transgenic glyphosate-tolerant cotton plants using glyphosate herbicidal compositions while mitigating PMIDA-induced necrosis so as to avoid significant leaf damage to the cotton crop grown under variable environmental conditions. One general approach is to control or limit the concentration of PMIDA in the manufactured glyphosate product and in turn the herbicidal glyphosate composition formulated using the product so that at the requisite application rate necessary to attain adequate weed control in the cotton crop, significant leaf necrosis is not induced in the treated plants. However, in some circumstances, a source of manufactured glyphosate having a sufficiently low concentration of PMIDA may be unavailable or it may be cost prohibitive or otherwise impractical to obtain or produce such a glyphosate product. Accordingly, another aspect of the present invention is to include in the glyphosate herbicidal composition containing appreciable levels of PMIDA certain safening agents that act to mitigate or inhibit PMIDA-induced necrosis in the cotton crop.

Although susceptibility to PMIDA-induced necrosis is common to cotton generally, this potential for leaf damage is particularly problematic in transgenic glyphosate-tolerant cotton plants because these varieties are engineered to allow over-the-top application of glyphosate herbicides. Accordingly, the strategies and methods disclosed herein for mitigating PMIDA-induced necrosis are particularly intended for the control of weeds in cotton production from transgenic glyphosate-tolerant cotton plants.

As used herein transgenic glyphosate-tolerant cotton plants includes plants grown from the seed of any cotton event that provides glyphosate tolerance and glyphosate-tolerant progeny thereof. Such glyphosate-tolerant cotton events include, without limitation, those that confer glyphosate tolerance by the insertion or introduction, into the genome of the plant, the capacity to express various native and variant plant or bacterial EPSPS enzymes by any genetic engineering means known in the art for introducing transforming DNA segments into plants to confer glyphosate resistance as well as glyphosate-tolerant cotton events that confer glyphosate tolerance by other means such as described in U.S. Pat. Nos. 5,463,175 and 6,448,476 and International Publication Nos. WO 2002/36782, WO 2003/092360 and WO 2005/012515.

Non-limiting examples of transgenic glyphosate-tolerant cotton events include the current commercial ROUNDUP READY cotton event designated 1445 and described in U.S. Pat. No. 6,740,488. Of particular interest in the practice of the present invention are methods for weed control in a crop of transgenic glyphosate-tolerant cotton plants in which glyphosate resistance is conferred in a manner that allows later stage application of glyphosate herbicides without incurring significant glyphosate-mediated reproductive injury. Non-limiting examples of such transgenic glyphosate-tolerant cotton plants include those grown from the seed of the ROUNDUP READY FLEX cotton event (designated MON 88913 and having representative seed deposited with American Type Culture Collection (ATCC) with Accession No. PTA-4854) and similar glyphosate-tolerant cotton events and progeny thereof as described in International Publication No. WO 2004/072235. ROUNDUP READY FLEX cotton event MON 88913 and similar glyphosate-tolerant cotton events may be characterized in that the genome comprises one or more DNA molecules selected from the group consisting of SEQ ID NO:1, SEQ ID NO:2, SEQ ID NO:3, and SEQ ID NO:4; or the genome in a DNA amplification method produces an amplicon comprising SEQ ID NO:1 or SEQ ID NO:2; or the transgenic glyphosate-tolerant cotton plants comprise a glyphosate tolerant trait that is genetically linked to a complement of a marker polynucleic acid, and the marker polynucleic acid molecule is homologous or complementary to a DNA molecule selected from the group consisting of SEQ ID NO:1 and SEQ ID NO:2 as described in International Publication No. WO 2004/072235, the entire contents of which are incorporated herein by reference. A sequence listing containing each of SEQ ID NOS: 1, 2, 3, and 4 as disclosed in International Publication No. WO 2004/072235 is contained herein. These sequences are listed as SEQ ID NOS: 1, 2, 3, and 4, respectively.

As noted above, the ROUNDUP READY FLEX cotton event MON 88913 allows for over-the-top application of glyphosate herbicides at advanced stages of plant development without incurring significant glyphosate-mediated reproductive injury (e.g., as quantified, for example, by flower pollen shed and/or lint yield). As compared to the previous commercial ROUNDUP READY cotton event designated 1445, ROUNDUP READY FLEX cotton event MON 88913 is particularly advantageous in allowing foliar application of glyphosate herbicide for weed control at a developmental age characterized by at least five leaf nodes present on a cotton plant of the crop. As used herein, a node having a leaf branch is referred to as a leaf node in accordance with the conventional node method used in assessing cotton plant developmental age. Furthermore, cotyledons are leaves originally contained in the seed and are not considered as plant leaves or nodes for purposes of determination of the stage of cotton development. That is, as generally accepted by those skilled in the art and as used herein, the stem point of cotyledon attachment is referenced as Node 0. The fifth and subsequent leaf nodes are typically the first reproductive (i.e., fruiting) branches and may develop a fruiting bud and associated leaf. A leaf node having a reproductive branch may be referred as a reproductive node. Cotton plants can develop as many as about 25 leaf nodes, with nodes 5-25 potentially developing into reproductive nodes. In practicing weed control in a crop of transgenic glyphosate-tolerant cotton grown from seed of ROUNDUP READY FLEX cotton event MON 88913 or similar cotton events and progeny thereof, glyphosate herbicidal formulations can be applied over-the-top of the crop at more advanced developmental ages characterized, for example, by six, ten, twelve, fourteen or more leaf nodes present on a cotton plant of the crop and up to and including layby without incurring significant glyphosate-mediated reproductive injury to the crop. The herbicidal glyphosate formulation may be applied over-the-top of the cotton crop at various intervals of advanced development, characterized, for example, by six or more leaf nodes and no more than ten, twelve, fourteen, sixteen, eighteen, twenty or twenty-five leaf nodes on a cotton plant of the crop. The strategies and methods disclosed herein for mitigating PMIDA-induced necrosis are particularly advantageous in weed control methods used in cultivation of ROUNDUP READY FLEX cotton and similar events that permit such later stage over-the-top application of glyphosate herbicides since the appearance of necrotic lesions on the treated cotton plants may appear to be more pronounced due to the more fully developed canopy and greater available leaf area.

By employing the various strategies discussed in detail below, PMIDA-induced leaf necrosis in transgenic glyphosate-tolerant cotton can be substantially avoided under the relevant growing conditions or at least sufficiently mediated or inhibited. The extent of leaf necrosis is readily quantified by plant biologists and technicians through visual assessment of the area of any necrotic lesions relative to the total leaf surface area of the cotton plants following treatment with a glyphosate herbicide. In the practice of the weed control methods of the present invention, PMIDA-induced necrotic lesions on the surface of the leaves of the transgenic glyphosate-tolerant cotton plants are generally inhibited so as on average to account for no more than about 25% of the total leaf area of the plants of the treated crop. Preferably, necrotic lesions on the surface of the leaves of the cotton plants treated in accordance with the present invention on average account for no more than about 20%, and even more preferably no more than about 15% of the total leaf area of the plants of the treated crop. By practicing the more preferred embodiments of the present invention disclosed herein, PMIDA-induced necrotic lesions on the surface of the leaves of the cotton plants may be advantageously inhibited so as to on average account for no more than about 10% or no more than about 5% of the total leaf area of the plants of the treated crop. In accordance with especially preferred embodiments of the present invention, onset of PMIDA-induced necrosis is substantially avoided under all relevant growing conditions including those noted above and discussed below that might otherwise tend to enhance the onset and severity of PMIDA-induced necrosis.

As noted above, the onset and severity of PMIDA-induced leaf necrosis in transgenic glyphosate-tolerant cotton plants is dependent on the prevailing growing conditions as well as the concentration of PMIDA in the glyphosate herbicide applied to the plants. In accordance with the present invention, it has been determined that under many growing conditions and at typical glyphosate application rates necessary for adequate weed control (e.g., at rates of from about 0.75 to about 1.125 lb glyphosate a.e./A or about 0.84 to about 1.26 kg glyphosate a.e./ha) significant PMIDA-induced leaf necrosis can generally be avoided by controlling the concentration of PMIDA in the herbicidal glyphosate composition such that the application rate of PMIDA is no more than about 2.5 g PMIDA acid equivalent per hectare, preferably no more than about 2.2 g PMIDA acid equivalent per hectare, more preferably no more than about 2 g PMIDA acid equivalent per hectare, and even more preferably no more than about 1.7 g PMIDA acid equivalent per hectare. However, because cotton plant susceptibility to PMIDA-induced necrosis is dependent upon environmental conditions that may vary widely from one growing location to another and throughout the growing season, in order to provide a safety factor and more consistently avoid the risk of expression of leaf injury, it is preferred to control the concentration of PMIDA in the herbicidal glyphosate composition and the application rate of the composition to the cotton plants to further reduce the application rate of PMIDA to no more than about 1.5 g PMIDA acid equivalent per hectare, even more preferably no more than about 1.2 g PMIDA acid equivalent per hectare, and still more preferably no more than about 1 g PMIDA acid equivalent per hectare. In accordance with even more preferred embodiments of the present invention, the concentration of PMIDA in the herbicidal glyphosate composition and the application rate of the composition are controlled such that the application rate of PMIDA is no more than about 0.7 g PMIDA acid equivalent per hectare, even more preferably no more than about 0.5 g PMIDA acid equivalent per hectare and especially no more than about 0.25 g PMIDA acid equivalent per hectare.

As apparent to those skilled in the art, based on typical glyphosate application rates necessary for adequate weed control in transgenic glyphosate-tolerant cotton (e.g., at rates of from about 0.75 to about 1.125 lb glyphosate a.e./A or about 0.84 to about 1.26 kg glyphosate a.e./ha), the composition including the concentration of PMIDA in the herbicidal glyphosate formulation applied to the plants, concentrates from which such formulations are prepared and ultimately the composition of the manufactured technical grade glyphosate product from which such compositions are prepared can be readily determined. Glyphosate manufacturing processes such as those including the oxidative cleavage of a PMIDA substrate or those utilizing glycine can be readily practiced or modified to produce a technical grade N-(phosphonomethyl) glycine product of sufficient glyphosate assay and having a PMIDA concentration suitable for producing herbicidal glyphosate compositions capable of achieving PMIDA application rates so as to not induce significant leaf necrosis in the treated plants. Exemplary process strategies for producing manufactured technical grade glyphosate products having sufficiently low PMIDA content are described in detail below.

In some situations, a source of manufactured glyphosate having a sufficiently low concentration of PMIDA may be unavailable or it may be cost prohibitive or otherwise impractical to obtain or produce such a glyphosate product. That is, it may not always be feasible or economically practical to control the concentration of PMIDA in the herbicidal glyphosate composition applied to the cotton plants at the rate necessary to attain adequate weed control while minimizing the PMIDA application rate to an extent sufficient to avoid inducing significant leaf necrosis in the treated plants. However, in accordance with another aspect of the present invention, glyphosate herbicidal composition containing appreciable levels of PMIDA (e.g., corresponding to an application rate in excess of about 2.5 g PMIDA acid equivalent per hectare and up to about 5 g or 10 g PMIDA acid equivalent per hectare or higher) that might otherwise lead to leaf necrosis can be safened by the inclusion of certain PMIDA safening agents or safeners that act to mitigate or inhibit PMIDA-induced necrosis in the cotton crop. Furthermore, even glyphosate herbicidal formulations containing reduced levels of PMIDA sufficient to attain a PMIDA application rate of no more than about 2.5 g PMIDA acid equivalent per hectare may further include a safening agent as an added measure of protection against PMIDA-induced necrosis.

Several classes of PMIDA safening agents suitable for inclusion in glyphosate herbicidal compositions containing PMIDA have been discovered. Some of these safening agents are believed to inhibit significant PMIDA-induced leaf necrosis by inhibiting buildup of phytotoxic free radicals in the tissues of cotton plants that might otherwise lead to membrane disruption and tissue death. Non-limiting examples of safening agents that interrupt free radical formation resulting from uptake of PMIDA in the foliar tissues of the treated cotton plants include antioxidants, certain metal ions and light absorbing compounds.

Antioxidants are believed to mitigate PMIDA-induced leaf necrosis by scavenging and destroying free radicals generated in the treated cotton plants. Indeed, observed reduction of PMIDA-induced necrosis through the use of antioxidants in accordance with the present invention is further evidence that the necrosis phenomenon is at least in part the result of free radical formation. More particularly, antioxidants added to glyphosate formulations of the present invention are believed to scavenge free radicals and retard the oxidation of organic plant materials such as lipids and proteins that can result in plant tissue damage such as by loss of chlorophyll and carotenoids and in leaky cell membranes with concomitant cell and cell organelle drying and disintegration.

Suitable antioxidants or free radical scavengers include those considered as generally recognized as safe (GRAS) as specified in 21 C.F.R. §182. For example, safening antioxidants may be selected from ascorbic acid, dehydroascorbic acid, ascorbyl palmitate, ascorbyl stearate, sodium ascorbate, sorbic acid, sodium sorbate, potassium sorbate, anoxomer, retinol, resorcinol, the various tocopherols and tocopha-trienes (e.g., D-α-tocopheryl acetate, D-α-tocopheryl acid succinate, D-β-tocopherol, D-γ-tocopherol, D-δ-tocopherol, D-α-tocotrienol, D-β-tocotrienol, Dγ-tocotrienol, DLα-tocopherol, DL-α-tocopheryl acetate, DL-α-tocbpheryl calcium succinate, DL-α-tocopheryl nicotinate, DL-α-tocopheryl linoleate/oleate and derivatives or stereo isomeric forms thereof), hydroquinone, butylated hydroxytoluene (BHT), butylated hydroxyanisole (BHA), t-butyl hydroquinone (TBHQ), propyl gallate, dodecyl gallate, isoamyl gallate, octyl gallate, reduced coenzyme-Q, flavones and isoflavones such as apigenin, quercetin, genistein and daidzein, pycnogenol, ubiquinone, ubiquinol, monosodium glutamate, butylated hydroxymethylphenol, dilauryl thiodipropionate, disodium ethylenediamine tetraacetate, tartaric acid, erythorbic acid, sodium erythorbate, ethoxyquin, ethyl protocatechuate, guaiac resin, gum guaiac, isopropyl citrate, monoglyceride citrate, lecithin, nordihydroguaiaretic acid, phosphoric acid, potassium lactate, potassium metabisulfite, potassium sulfite, sodium hypophosphite, sodium lactate, sodium metabisulfite, sodium sulfite, sodium thiosulfate, stannous chloride, tertiary butylhydroquinone, 3-t-butyl-4-hydroxyanisole, calcium ascorbate, calcium disodium EDTA, catalase, cetyl gallate, clove extract, coffee bean extract, 2,6-di-t-butylphenol, disodium citrate, edetic acid, 6-ethoxy-1,2-dihydro-2,2,4-trimethylquinoline, ethyl gallate, ethyl maltol, eucalyptus extract, fumaric acid, gentian extract, glucose oxidase, heptyl paraben, hesperetin, 4-hydroxymethyl-2,6-di-t-butylphenol, N-hydroxysuccinic acid, lemon juice, lemon juice solids, maltol, methyl gallate, methylparaben, phosphatidylcholine, pimento extract, potassium bisulfite, potassium sodium tartrate anhydrous, rice bran extract, rosemary extract, sage extract, sodium ascorbate, sodium erythorbate, sodium hypophosphate, sodium hypophosphate, sodium thiosulfate pentahydrate, soy flour, sucrose, α-terpineol, tocopherol, D-α-tocopherol, DL-α-tocopherol, tocopheryl acetate, D-α-tocopheryl acetate, DL-α-tocopheryl acetate, 2,4,5-trihydroxybutyrophenone, wheat germ oil, thiodipropionic acid and mixtures thereof. In some cases, a combination of antioxidants is used as the safening agent wherein the antioxidants work together to produce an effect in mitigating PMIDA-induced necrosis that is greater than that achieved using a comparable amount of each antioxidant individually.

Experimental results indicate that all antioxidants evaluated showed some ability to counteract PMIDA-induced necrosis in glyphosate treated cotton. In accordance with a preferred embodiment, the antioxidant safening agent is selected from hydroquinone, resorcinol, BHA, BHT and mixtures thereof.

The requisite amount of antioxidant to add to the herbicidal glyphosate compositions to avoid significant PMIDA-induced necrosis in the treated cotton plants depends on the PMIDA concentration, the selected antioxidant or combination of antioxidants and the relative ability of the antioxidant safening agent to scavenge free radicals and may be readily determined empirically by one skilled in the art through routine experimentation. The safening agent comprising one or more antioxidants is preferably added to herbicidal glyphosate compositions, including concentrates and tank mixes, at a molar ratio to PMIDA of from about 50:1 to about 1:1, from about 40:1 to about 1:1, from about 30:1 to about 1:1, from about 20:1 to about 1:1, from about 15:1 to about 1:1, from about 10:1 to about 1:1, from about 5:1 to about 1:1, from about 3:1 to about 1:1, or even from about 2:1 to about 1:1.

Certain metal ions present in the herbicidal glyphosate compositions may also act as a safening agent to mitigate PMIDA-induced leaf necrosis in the treated cotton plants. PMIDA, by virtue of the presence of carboxyl and a phosphonomethyl groups or ligands, can function as a strong complexing agent and can chelate or otherwise bind with free metal ions in solution and thereby be sequestered (e.g., not taken up into the foliar tissues of the cotton plant) or otherwise rendered bio-inactive to the cotton plant. PMIDA present in glyphosate compositions is believed to selectively bind or otherwise form a complex (e.g., a (II) or (III) coordination complex or chelate) or salt with metal ions and thereby render it biologically unavailable in the formation of free radicals in the cotton plant. That is, the metal ion added to the composition is subject to formation of a complex or salt with PMIDA (e.g., N-(phosphonomethyl)iminodiacetic acid or an anion formed by deprotonation or partial deprotonation thereof). Importantly, PMIDA forms more stable complexes with such metal ions than does glyphosate such that the PMIDA and not the glyphosate selectively complexes or binds with the metal ions, thereby avoiding significant negative impact on herbicidal activity that would occur if a significant amount of glyphosate were rendered inactive by complexing or binding with the metal ion.

The metal ion added to the glyphosate composition as a PMIDA safening agent may be any transition metal or other metal and is preferably agronomically acceptable and recognized as inert for permitted use in agricultural herbicide compositions. Suitable non-limiting examples of metal ion safening agents include aluminum, antimony, iron, chromium, nickel, manganese, cobalt, copper, zinc, vanadium, titanium, molybdenum, tin, barium and mixtures thereof. In one preferred embodiment, the metal ion is selected from aluminum, copper, iron, zinc and mixtures thereof. In another preferred embodiment, the safening agent comprises iron ions or a mixture of iron ions and zinc ions or a mixture of iron ions and copper ions. In one preferred embodiment, the metal ion safening agent added to the herbicidal composition for selective complexing or binding with PMIDA comprises a polyvalent metal ion (e.g., $Fe(III)$, $Al(III)$, $Zn(II)$, and $Cu(II)$).

The metal ion introduced into herbicidal glyphosate compositions may be derived from various salts (e.g., the salt of a strong acid such as a metal chloride or metal sulfate or the salt of a di-, tri- or other polycarboxylic acid or derivative) or other compounds by dissociation or dissolution in the composition or from the elemental metal. Suitable source compounds for the metal ions include, without limitation, aluminum chloride, aluminum hydroxide, aluminum oxide, aluminum sulfate, antimony trioxide, barium carbonate, barium sulfate, cobalt carbonate, cobalt sulfate, copper acetate, copper carbonate, copper hydroxide, copper nitrate, copper sulfate, cupric oxide, cuprous oxide, ferric ammonium sulfate, ferric chloride, ferric oxide, ferric oxide hydrate, ferric sulfate, ferrous ammonium sulfate, ferrous oxide, ferrous sulfate, iron, iron salts of di-, tri- or other polycarboxylic acids such as iron citrate, iron hydroxide oxide, ferosoferric oxide, nickel chloride, nickel acetate, nickel sulfate, potassium aluminum sulfate, potassium permanganate, sodium aluminate, sodium aluminum phosphate, sodium chromate, sodium iron(III) ethylenediaminetetraacetate, sodium molybdate, sodium permanganate, sodium potassium aluminum silicate, tin oxide, titanium sulfate, vanadyl sulfate, zinc acetate, zinc chloride, zinc hydroxide, zinc iron oxide, zinc naphthenate, zinc oxide, zinc oxide sulfate ($Zn_4O_3(SO_4)$), zinc sulfate (basic), zinc sulfate (monohydrate) and mixtures thereof.

In one preferred embodiment, the metal ion safening agent added to the herbicidal composition for selective complexing or binding with PMIDA comprises polyvalent iron (e.g., $Fe(III)$) and is derived from ferric ammonium sulfate, ferric chloride, ferric oxide, ferric oxide hydrate, ferric sulfate, ferrous ammonium sulfate, ferrous oxide, ferrous sulfate and/or iron salts of di-, tri- or other polycarboxylic acids such as iron citrate. In one preferred embodiment, a safening agent comprising polyvalent iron ions in the herbicidal glyphosate composition is derived from ferric sulfate, ferric chloride and/or iron citrate.

When preparing glyphosate concentrate compositions containing certain metal ion safening agents such as iron derived from iron oxide, ferric chloride or ferric sulfate, it may be necessary to first mix the metal ion with a suitable solubilizing or stabilizing ligand (sL) in an aqueous solution before combining it with the PMIDA-containing glyphosate. For example, aqueous solutions of the metal ion and solubilizing ligand may be mixed and then the mixture combined with glyphosate and other components of the composition. This practice inhibits precipitation of a metal salt of glyphosate and/or the precipitation of metal hydroxide in the composition thereby rendering the metal ion unavailable for complexing or binding with PMIDA. The severity of these solubility issues appears to be somewhat dependent upon the identity of the metal salt of glyphosate included in the concentrate composition and, for example, is more problematic when preparing iron safened concentrate compositions containing the potassium salt of glyphosate as compared to the isopropylamine salt of glyphosate. The solubilizing or stabilizing ligand, is selected to (1) form a complex with the metal ion with sufficient stability to be competitive with glyphosate's metal complex stability and sufficiently stable to prevent any metal salt hydrolysis to metal hydroxides at the pH of the composition (typically pH of 4 to 5); and (2) form a complex weaker than that formed by PMIDA, thereby allowing PMIDA to displace and replace this solubilizing ligand from the metal in the final composition. The metal-ligand formation constants are used to quantify the complex's stability, and can be readily determined by potentiometric titration or found in the literature. The complex stability for the solubilizing ligand can also be controlled by adjusting the amount used relative to the metal ion. Specifically, the molar ratio of solubilizing ligand to metal ion is optimized to eliminate the adverse effects that are observed on herbicidal activity and formulation homogeneity, detailed above, when simple, aqueous metal ions are used. This molar ratio is typically greater than 1, and is usually from about 1.5 to about 4 (sL/metal). The composition will thus contain three primary materials capable of complexing or binding with the metal ion (i.e., in order of decreasing stability, decreasing metal-ligand formation constant PMIDA>sL~ glyphosate). Examples of suitable solubilizing ligands include polyacids (e.g., polycarboxylic acids) and hydroxyl acids like citric acid, gluconic acid, oxalic acid, malonic acid, succinic acid, malic acid, tartaric acid, fumaric acid, maleic acid, glutaric acid, dimethylglutaric acid, adipic acid, trimethyladipic acid, pimelic acid, tartronic acid, suberic acid, azelaic acid, sebacic acid, 1,12-dodecanedioic acid, 1,13-tridecanedioic acid, glutamic acid, phthalic acid, isophthalic acid, lactic acid, terephthalic acid, or an anhydride, ester, amide, halide, salt or precursor of any of these acids, polyhydroxy compounds like fructose and catechol, amino acids, proteins and polysaccharides. In accordance with one preferred embodiment, the solubilizing ligand comprises a polycarboxylic acid such as citric acid.

An additional complication exists with aqueous solutions of iron (III). At a pH of up to about 2, ferric iron has a strong tendency to hydrolyze to form a binuclear species, $[Fe(H_2O)4(OH)2Fe(H_2O)4]^{4+}$ and at a pH above about 2 to 3 polynuclear Fe—OH species. The latter results in the precipitation of colloidal or hydrous ferric oxide. Glyphosate compositions have a pH around 4.5 units. However, this problem can likewise be overcome by employing a suitable solubilizing ligand as described above. The solubilizing ligand selected (e.g., citric acid, fructose) possesses a metal stability constants less than that of PMIDA, to allow PMIDA to displace the solubilizing ligand, but stable enough to prevent hydrolysis of Fe(III) as described above. As an alternative to or in addition to using a solubilizing ligand to overcome solubility and precipitation issues that might arise when preparing glyphosate concentrate compositions containing certain metal ion safening agents, it may be advantageous to use a mixture of metal ions to prepare a suitable safened concentrate. For example, a combination of iron ions and zinc ions or a combination of iron ions and copper ions may be employed.

The amount of metal ion safening agent introduced into the composition relative to PMIDA is selected to ensure the reduction of free (i.e., non-bound or non-complexed) PMIDA to a level sufficiently low so as to not induce significant leaf necrosis in the cotton crop and can be readily determined through routine experimentation. The minimally effective molar ratio of metal ion safening agent to PMIDA in the herbicidal glyphosate composition depends upon the PMIDA concentration. As the concentration of PMIDA in the manufactured glyphosate product from which herbicidal glyphosate compositions such as concentrates and tank mixes are prepared decreases, a lower molar ratio of metal ion safening agent to PMIDA (e.g., even less than 1:1) may be effectively utilized in the composition and satisfactory results obtained since free, biologically active PMIDA in the composition may be reduced by the safening agent to a level that prevents significant PMIDA-induced necrosis in the treated cotton plants at the designated application rate. The safening agent comprising one or more metal ions is generally added to herbicidal glyphosate compositions, including concentrates and tank mixes, at a molar ratio to PMIDA of at least about 0.15:1, at least about 0.2:1, at least about 0.25:1, at least about 0.3:1, at least about 0.35:1, at least about 0.4:1 and preferably at a molar ratio to PMIDA of at least about 0.45:1, at least about 0.5:1, at least about 0.55:1, at least about 0.6:1, at least about 0.65:1, at least about 0.7:1, at least about 0.75:1, at least about 0.8:1, at least about 0.85:1, at least about 0.9:1 or even at least about 0.95:1. Typically, the molar ratio of the metal ion safening agent to PMIDA in the herbicidal glyphosate composition is no greater than about 25:1, no greater than about 20:1, no greater than about 15:1, no greater than about 10:1, no greater than about 5:1, no greater than about 4:1, no greater than about 3:1 and preferably no greater than about 2.5:1. Often the concentration of PMIDA in the manufactured glyphosate product is sufficiently high such that the molar ratio of the metal ion safening agent to PMIDA in the herbicidal glyphosate composition including concentrates and tank mixes is at least about 0.5:1, typically from about 0.5:1 to about 25:1, from about 0.5:1 to about 20:1, from about 1:1 to about 25:1, from about 1:1 to about 20:1, from about 1:1 to about 15:1, from about 1:1 to about 10:1, from about 1:1 to about 9:1, from about 1:1 to about 8:1, from about 1:1 to about 7:1, from about 1:1 to about 6:1, from about 1:1 to about 5:1, from about 1:1 to about 4:1, preferably from about 1:1 to about 3:1, more preferably from about 1:1 to about 2.5:1, and even more preferably from about 1:1 to about 2:1. Utilizing a metal ion safening agent in the glyphosate herbicidal compositions of the present invention allows the application rate of free, biologically active PMIDA to be reduced to no more than about 2.5 g PMIDA acid equivalent per hectare and lower (e.g., as noted above and preferably no more than about 1.5 g, more preferably no more than about 1.2 g, more preferably no more than about 1 g, even more preferably no more than about 0.7 g, still more preferably no more than about 0.5 g and especially no more than about 0.25 g PMIDA acid equivalent per hectare) and thereby inhibit significant PMIDA-induced necrosis in the treated cotton plants.

In practicing the various embodiments of the present invention, it may be necessary to determine the PMIDA content of a material such as manufactured glyphosate product used in formulation of concentrates, tank mixes or other forms of herbicidal compositions or the PMIDA content of the formulated herbicidal compositions themselves, for example, to determine whether a safening agent is necessary, the quantity of safening agent to be employed as well as to assure compliance with the established compositional specifications. Analytical methods for determining PMIDA content are available to those skilled in the art. One such method using a high-pressure liquid chromatography procedure (HPLC) is described in Example 3 below.

Similarly, in practicing the embodiment described herein calling for use of certain metal ion safening agents, it may be necessary to accurately determine the metal ion content of an herbicidal glyphosate composition. Methods for analyzing a product or material to determine the concentration of metal ions such as those disclosed herein suitable for use as a safening agent are likewise available to those skilled in the art. By way of example, trace concentrations of iron in materials used and produced in the practice of the present invention may be measured using the test method based on photometric determination of the 1,10-phenanthroline complex formed with the iron(II) ion described in ASTM E 394-94.

In accordance with another embodiment of the invention, the safening agent included in the herbicidal glyphosate composition comprises a light absorbing compound that acts to protect the treated cotton plant from particular light spectra to inhibit free radical production associated with photo-activated PMIDA-induced necrosis. Generally, the light absorbing compound is selected so as to preferentially block at least a portion of the visible light spectrum near the wavelength(s) associated with PMIDA-induced free radical production in the treated cotton plant and to transmit other portions of the visible light spectrum necessary for adequate photosynthesis and plant health.

Suitable light absorbing compounds include certain dyes such as FD&C yellow dye #5 (commonly known as tartrazine and having the chemical name 3-carboxy-5-hydroxy-1-p-sulfophenyl-4-p-sulfophenylazopyrazole trisodium salt), FD&C Blue #1, FD&C Red #40, FD&C Red #33, FD&C Violet #1, Fast Green FCF, methylene blue and mixtures thereof. Tartrazine having a maximum light absorbance at a wavelength of about 425 nm, was tested as a safening agent in glyphosate spray solutions and found to significantly decrease PMIDA-induced necrosis in the treated cotton plants. The amount of tartrazine or other light absorbing compound introduced into the composition as a safening agent is selected to ensure absorbance of at least a portion of the visible light spectrum near the wavelength(s) associated with PMIDA-induced free radical production in the treated cotton plant so as to reduce the formation of free radicals to a level sufficient to not induce significant leaf necrosis in the cotton crop and can be readily determined through routine experimentation. For example, the safening agent comprising tartrazine or other dye is generally added to herbicidal glyphosate compositions, including concentrates and tank mixes, in an amount sufficient such that at least about 50, 60, 70, 80 or 90% or more of the incident light at the relevant wavelength(s) is absorbed. The preferred amount depends on the identity of the dye or other light absorbing compound and the relative ability of the material to absorb incident light at the relevant wavelength(s) associated with PMIDA-induced free radical production. Some dyes and other light absorbing compounds have a tendency to degrade or fade over time or upon exposure to light. Accordingly, in practicing this embodiment of the invention, it may be useful to incorporate the dye or other light absorbing compound into the glyphosate composition just prior to use or to take other measures to ensure the safening activity of the dye is not significantly diminished.

Humectants are another class of safening agents that may be employed in the practice of the present invention to inhibit PMIDA-induced necrosis in treated cotton plants. Humectants are believed to mitigate PMIDA-induced necrosis by protecting or aiding in the repair of cell membranes in the foliar tissues of the cotton plants damaged by free radicals and/or by modifying or altering the leaf surface/herbicidal formulation interface, thus affecting the uptake of PMIDA. Without being bound by any particular theory, it is postulated that humectants can be entrapped in the interstices of the cell wall surfaces, where they act as a hygroscopic agent, thus increasing the amount of water held in this area. The humectants employed in the compositions of this invention are preferably water-soluble and are substantially non-ionizable. By substantially non-ionizable it is meant that no significant or detectable disassociation in water occurs. Such humectants can be employed in addition to or substituted partially for, the water component of the inventive herbicidal glyphosate compositions.

Examples of suitable humectants include, without limitation, materials selected from the group consisting of glycerin, urea, guanidine, glycolic acid and glycolate salts (e.g., ammonium and quaternary alkyl ammonium), lactic acid and lactate salts (e.g., ammonium and quaternary alkyl ammonium), polyhydroxy alcohols such as sorbitol, xylitol, inositol, mannitol, pantothenol, glycerol, hexanetriol (e.g., 1,2,6-hexanetriol), 1,4-butanediol, tetramethyl-6-decyne-4,7-diol, PEG-5 pentaerythritol ether, polyglyceryl sorbitol, diethylene glycol, propylene glycol, butylene glycol, hexylene glycol and the like, polyethylene glycols, sugars and starches (e.g. sucrose), sugar and starch derivatives (e.g., alkoxylated glucose, hydrogenated partially hydrolyzed polysaccharides and hydrogenated starch hydrolysate), hyaluronic acid, lactamide monoethanolamine, acetamide monoethanolamine, sodium 2-pyrrolidone-5-carboxylate, collagen, gelatin, 10 to 20 mole ethoxylates or propoxylates of glucose (e.g., GLUCAM E-20) and mixtures thereof. Preferred humectants include sorbitol, xylitol, inositol, mannitol, pantothenol, glycerol and derivatives and mixtures thereof.

The humectant is preferably added to the glyphosate compositions, including concentrates and tank mixes, in a molar excess to PMIDA, for example, at a molar ratio to PMIDA of from about 1000:1 to about 1:1, from about 500:1 to about 1:1, from about 250:1 to about 1:1, from about 100:1 to about 1:1, from about 50:1 to about 1:1, from about 40:1 to about 1:1, from about 30:1 to about 1:1, from about 20:1 to about 1:1, from about 15:1 to about 1:1, from about 10:1 to about 1:1, from about 5:1 to about 1:1, from about 3:1 to about 1:1 or even from about 2:1 to about 1:1. The preferred ratio depends on the PMIDA concentration, the humectant and the relative ability the humectant safening agent to mitigate PMIDA-induced tissue damage and may be readily determined by one skilled in the art using routine experimentation.

It should be understood that in the practice of the present invention wherein a safening agent is used in a herbicidal glyphosate composition containing PMIDA to mitigate leaf necrosis in the treated cotton plants, the safening agent may comprise any combination of two or more materials selected from the various classes of safening agents disclosed herein and including combinations of antioxidants, metal ions, light absorbing compounds, humectants and/or certain surfactants effective in mitigating PMIDA-induced necrosis as disclosed in greater detail below. Moreover, it should be understood that many of the specific safening agents disclosed herein may be multifunctional and, although identified within a particular class of safening agents, may provide safening against PMIDA-induced necrosis through one or more mechanisms common to other classes of safening agents.

In another embodiment of the present invention, an adjuvant is selected to control, or moderate, the rate of PMIDA uptake into the cotton plant such that the plant can metabolize the PMIDA without development of significant leaf necrosis. Alternatively, the adjuvant can render the PMIDA less biologically active before cellular uptake and translocation of the PMIDA in the plant.

In one embodiment, the adjuvant is a compound having at least two hydroxyl substituents that are oriented no more than 6 atoms apart and in the same spatial orientation within the molecule. Such adjuvants include diols, triols, polyols, and the like, such as alkanediols, alkenediols, alkynediols, benzenediols, dialkanolamines, trialkanolamines, polyalkylene glycols, dialkylene glycols, trialkylene glycols, and alkylpolyglucosides. Some suitable adjuvants are nonionic surfactants, such as esters of polyhydric alcohols, alkoxylated amides, alkoxylated alkylphenols, alkoxylated arylphenols, fatty alcohol alkoxylates, alcohol alkoxylates, and alkylpolyglucosides. Commercially available alkylpolyglucosides include AGRIMUL APG 2067, APG 2069 (nonyl/decyl polyglucoside having an average of 1.6 polyglucoside units) and APG 2076 all from Cognis, BEROL AG6202 (2-ethyl-1-hexylglycoside from Akzo Nobel) and AL2042 (octyl/decyl with an average of 1.7 glycoside units available from Imperial Chemical Industries PCL).

In an embodiment of the invention, the glyphosate composition is formulated such that the weight ratio of the PMIDA uptake-moderating adjuvant to PMIDA present in the glyphosate composition is selected so that the rate of transfer of PMIDA into the foliar tissues of the plant is sufficiently low enough to inhibit significant leaf necrosis. Stated another way, the adjuvant, when applied as part of an aqueous glyphosate spray composition, is of the type and present in a sufficient concentration to prohibit the crop of transgenic glyphosate-tolerant cotton plants from cellularly uptaking and translocating an amount of PMIDA thereof sufficient to induce significant leaf necrosis in the cotton plant. One way to accomplish this is to select an adjuvant which, when compared to an equivalent amount by weight of an alkoxylated alkylamine surfactant (e.g., ethoxylated tallowamine), provides less intimate contact between the applied herbicidal composition and the microtopographically rough surface of the cotton plant, for example by increasing the contact angle of the composition, so as to minimize spreading of the composition into crevices and pores in the plant. Another means for decreasing the rate of PMIDA uptake is to select an adjuvant that minimizes sticking or adhesion to a plant surface when used in an aqueous spray composition as compared to the same composition containing the alkoxylated alkylamine rather than the selected adjuvant. Yet another way of reducing the rate of PMIDA uptake is to select an adjuvant that causes the spray composition to dry faster, minimizing penetration through the leaf cuticle relative to the same composition containing the alkoxylated alkylamine rather than the selected adjuvant. These various adjuvant selection strategies may also negatively impact the herbicidal activity of glyphosate and therefore are preferably employed so as to provide a differential effect to obtain the desired reduction in PMIDA-induced necrosis in the treated cotton plant without significantly undermining glyphosate herbicidal activity under the relevant growing conditions.

The PMIDA uptake-moderating adjuvant is preferably added to the glyphosate composition at a weight ratio to PMIDA of between about 200:1 to 1:1, 150:1 to 1:1, 100:1 to 1:1, 75:1 to 1:1, 50:1 to 1:1, 40:1 to 1:1, 30:1 to 1:1, 20:1 to 1:1 or even 10:1 to 1:1. A preferred ratio depends on the PMIDA concentration, the identity of the adjuvant and the relative ability of that adjuvant to control, or moderate, the rate of PMIDA uptake into the cotton plant. A preferred ratio may be readily determined by one skilled in the art using routine experimentation.

It is to be noted that the present invention encompasses any glyphosate formulation disclosed herein (e.g., concentrate, solid or tank mix) which comprises reduced amounts of PMIDA or any one of the PMIDA safening agents or safeners described above, as well as any combination or mixture which includes any one, two, three, four, five or six of these safeners. Exemplary combinations are set forth in greater detail in Formulation Tables A-E, below (which illustrate that glyphosate acid and/or salts or other derivatives thereof, can be combined with a safening agent or a reduced amount of PMIDA to form a herbicidal composition comprising two to seven components, wherein: G=glyphosate; AO=antioxidant; MI=metal ion; LA=light absorbing compound; H=humectant; CU=adjuvant for mitigating cellular uptake of PMIDA or biological activity of PMIDA; P=reduced amount of PMIDA; and Active No. is a herbicide combination reference number):

TABLE A

Glyphosate in Combination with One Safener or a Reduced Amount of PMIDA

| Active No. | Herbicides |
|---|---|
| 1 | G + AO |
| 2 | G + MI |
| 3 | G + LA |
| 4 | G + H |
| 5 | G + CU |
| 6 | G + P |

TABLE B

Glyphosate in Combination with Two Safeners or One Safener and a Reduced Amount of PMIDA

| Active No. | Herbicides |
|---|---|
| 7 | G + AO + P |
| 8 | G + AO + MI |
| 9 | G + AO + H |
| 10 | G + AO + CU |
| 11 | G + AO + LA |
| 12 | G + P + MI |
| 13 | G + P + H |
| 14 | G + P + CU |
| 15 | G + P + LA |
| 16 | G + MI + H |
| 17 | G + MI + CU |
| 18 | G + MI + LA |
| 19 | G + H + CU |
| 20 | G + H + LA |
| 21 | G + CU + LA |

TABLE C

Glyphosate in Combination with Three Safeners or Two Safeners and a Reduced Amount of PMIDA

| Active No. | Herbicides |
|---|---|
| 22 | G + AO + P + MI |
| 23 | G + AO + P + H |
| 24 | G + AO + P + CU |
| 25 | G + AO + P + LA |
| 26 | G + AO + MI + H |
| 27 | G + AO + MI + CU |
| 28 | G + AO + MI + LA |
| 29 | G + AO + H + CU |
| 30 | G + AO + H + LA |
| 31 | G + AO + CU + LA |
| 32 | G + P + MI + H |
| 33 | G + P + MI + CU |
| 34 | G + P + MI + LA |
| 35 | G + P + H + CU |
| 36 | G + P + H + LA |
| 37 | G + P + CU + LA |
| 38 | G + MI + H + CU |
| 39 | G + MI + H + LA |
| 40 | G + MI + CU + LA |
| 41 | G + H + CU + LA |

TABLE D

Glyphosate in Combination with Four Safeners or Three safeners and a Reduced Amount of PMIDA

| Active No. | Herbicides |
|---|---|
| 42 | G + AO + P + MI + H |
| 43 | G + AO + P + MI + CU |
| 44 | G + AO + P + MI + LA |
| 45 | G + AO + P + H + CU |
| 46 | G + AO + P + H + LA |
| 47 | G + AO + P + CU + LA |
| 48 | G + AO + MI + H + CU |
| 49 | G + AO + MI + H + LA |
| 50 | G + AO + MI + CU + LA |
| 51 | G + AO + H + CU + LA |
| 52 | G + P + MI + H + CU |
| 53 | G + P + MI + H + LA |
| 54 | G + P + MI + CU + LA |
| 55 | G + P + H + CU + LA |

TABLE D-continued

Glyphosate in Combination with Four Safeners or
Three safeners and a Reduced Amount of PMIDA

| Active No. | Herbicides |
|---|---|
| 56 | G + MI + H + CU + LA |

TABLE E

Glyphosate in Combination Five Safeners or Four
Safeners and a Reduced Amount of PMIDA

| Active No. | Herbicides |
|---|---|
| 57 | G + AO + P + MI + H + CU |
| 58 | G + AO + P + MI + H + LA |
| 59 | G + AO + P + MI + CU + LA |
| 60 | G + AO + P + H + CU + LA |
| 61 | G + AO + MI + H + CU + LA |
| 62 | G + P + MI + H + CU + LA |

The safeners as described above can be added to any glyphosate liquid concentrate, solid concentrate, technical grade glyphosate product, ready-to-use concentrate, or spray composition. Glyphosate is typically formulated as a salt in an aqueous liquid concentrate, a solid concentrate, an emulsion or a microemulsion. Suitable salt forms of glyphosate which may be used in accordance with any of the formulations of the present invention include, for example, alkali metal salts, for example sodium and potassium salts, ammonium salts, di-ammonium salts such as dimethylammonium, alkylamine salts, for example dimethylamine and isopropylamine salts, alkanolamine salts, for example ethanolamine salts, alkylsulfonium salts, for example trimethylsulfonium salts, sulfoxonium salts, and mixtures or combinations thereof. Examples of commercial formulations of glyphosate include, without restriction: ROUNDUP ULTRA, ROUNDUP ULTRAMAX, ROUNDUP CT, ROUNDUP EXTRA, ROUNDUP BIOACTIVE, ROUNDUP BIOFORCE, RODEO, POLARIS, SPARK and ACCORD, all of which contain glyphosate as its isopropylammonium salt (IPA); ROUNDUP DRY and RIVAL which contain glyphosate as its ammonium salt; ROUNDUP GEOFORCE, a sodium glyphosate formulation; TOUCHDOWN, a glyphosate trimesium salt formulation, TOUCHDOWN IQ, a glyphosate diammonium salt formulation, TOUCHDOWN TOTAL IQ, a potassium glyphosate formulation, and ROUNDUP WEATHERMAX, a potassium glyphosate formulation.

The relative amount of glyphosate present in a contemplated herbicidal composition (i.e., a particulate solid concentrate, or liquid concentrate, or alternatively a ready-to-use, or tank-mix, composition) may vary depending upon many factors, including for example the weed species to be controlled and the method of application. Generally speaking, however, the concentration of glyphosate, and optionally a surfactant and/or some other adjuvant or additive (as described elsewhere herein), in the herbicidal compositions of the invention is sufficient to provide at least about 70% control (as determined by means known in the art) within about 50 days, preferably about 40 days, more preferably about 30 days, still more preferably about 20 days, still more preferably about 15 days, still more preferably about 10 days, still more preferably about 5 days, and even still more preferably about 1 day, or less, after application of the composition to a weed. In a more preferred embodiment, the concentration of glyphosate, and optionally a surfactant and/or some other additive, in the herbicidal compositions of the invention is sufficient to provide at least about 80%, more preferably at least about 85%, still more preferably at least about 90%, and still more preferably at least about 95%, control, or more, within about 50 days, preferably about 40 days, more preferably about 30 days, still more preferably about 20 days, still more preferably about 15 days, still more preferably about 10 days, still more preferably about 5 days, and even still more preferably about 1 day, or less, after application of the composition to a weed.

Additionally, the concentration of glyphosate, and optionally a surfactant and/or some other adjuvant or additive (as described elsewhere herein), in the herbicidal compositions of the invention is sufficient to provide at least about 70% control of weed regrowth (as determined by means known in the art) for at least about 20, preferably at least about 30, more preferably at least about 40, still more preferably at least about 50, still more preferably at least about 60, still more preferably at least about 70, still more preferably at least about 80, or even still more preferably at least about 90, days after application of the composition to a weed. In a more preferred embodiment, the concentration of glyphosate, and optionally a surfactant and/or some other adjuvant or additive, in the herbicidal compositions of the invention is sufficient to provide at least about 80%, more preferably at least about 85%, still more preferably at least about 90%, or still more preferably at least about 95% control, or more, for at least about 20, more preferably at least about 30, still more preferably at least about 40, still more preferably at least about 50, still more preferably at least about 60, still more preferably at least about 70, still more preferably at least about 80, or even still more preferably at least about 90, days after application to the weed.

Accordingly, liquid concentrate compositions of the invention are formulated to include glyphosate in a concentration of at least about 50 grams, preferably at least about 75 grams, and more preferably at least about 100, 125, 150, 175, 200, 225, 250, 275, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690 or 700 grams (acid equivalent or a.e.) per liter, or more. The glyphosate concentration ranges, for example, from about 50 to about 680 grams (a.e.) per liter, from about 100 to about 600 grams (a.e.) per liter (gpl), from about 250 to about 600 grams (a.e.) per liter, or from about 360 to about 540 grams (a.e.) per liter. When expressed as a weight percentage based on the total weight of the glyphosate concentrate, a liquid concentrate of the invention comprises at least about 10 wt. % glyphosate (acid equivalent or a.e.), preferably at least about 15 wt. %, and more preferably at least about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, or 68 wt. % a.e., or more. The glyphosate concentration ranges, for example, from about 10 wt. % to about 70 wt. % a.e., more preferably from about 20 wt. % to about 68 wt. % a.e., and even more preferably from about 25 wt. % to about 45 wt. % a.e. If the concentrate is applied as a ready-to-use composition, the glyphosate concentration is typically from about 1 wt. % to about 3 wt. % a.e., and more preferably from about 1 wt. % to about 2 wt. % a.e.

When expressed as a weight percentage based on the total weight of the glyphosate concentrate, solid concentrate compositions of the invention are formulated to include glyphosate in a concentration of at least about 5 wt. % glyphosate (acid equivalent or a.e.), preferably at least about 20 wt. % a.e., and more preferably at least about 25, 30, 35, 40, 45, 50, 55, 60, 65, 70, 75, 80, 85, 90, or 95 wt. % a.e., or more. The glyphosate concentration ranges, for example, from about 5 wt. % to about 97 wt. % a.e., more preferably from about 30 wt. % to about 85 wt. % a.e., and even more preferably from about 50 wt. % to about 75 wt. % a.e.

Spray compositions of the invention are formulated for application of at least about 1 gallon of spray composition per acre, preferably at least about 2, 3, 4, 5, 6, 7, 8, 9, 10, 11, 12, 13, 14, 15, 16, 17, 18, 19, or 20 gallons per acre, or more. The spray volume of the spray composition ranges, for example, from about 1 gallon to about 100 gallons per acre, more preferably from about 2 gallons to about 40 gallons per acre, and more preferably from about 2 gallons to about 5 gallons per acre for an aerial application and from about 5 gallons to about 20 gallons per acre for a ground application. The glyphosate in such spray compositions is applied to glyphosate-tolerant transgenic cotton plants at rates of from about 0.75 to about 1.125 lb glyphosate a.e./A or about 0.84 to about 1.26 kg glyphosate a.e./ha.

Preparation of Glyphosate Compositions

Unless otherwise noted herein, the herbicidal compositions of the invention that include one or more PMIDA safening agents or safeners can be prepared on site by the end-user shortly before application to the foliage of the vegetation to be killed or controlled by mixing in an aqueous solution (i) a glyphosate composition, (ii) a safener, and (iii) any optional components, such as a suitable surfactant or other adjuvant(s). Such compositions are typically referred to as "tank-mix" compositions. Typically, herbicidal compositions of the present invention that are ready to be applied directly to foliage can be made with a glyphosate concentration as described elsewhere herein. In one embodiment, an additive composition or mixture is provided for the end-user to provide the PMIDA safener to be added to the tank mix. The additive composition or mixture can optionally include surfactant and/or other adjuvant components typical in a glyphosate tank mix, and can be provided as a liquid or solid. For example, the end-user can be provided with a sachet of solid material that can be added to the aqueous solution and mixed to dissolve the material.

Alternatively, the herbicidal compositions of the invention may be provided to the end-user already formulated, either at the desired dilution for application (i.e., "ready-to-use" compositions) or requiring dilution, dispersion, or dissolution in water by the end-user (i.e., "concentrate" compositions). Such pre-formulated concentrates can be liquids or particulate solids.

With respect to the particulate solids, or dry formulations, of the present invention, it is to be noted that these may be in the form of powders, pellets, tablets flakes or granules. These dry formulations are typically dispersed or dissolved into water prior to use. Preferably, there are no substantially water insoluble constituents present at substantial levels in such formulations such that the formulations are substantially water soluble. In dry formulations of the present invention, the glyphosate itself may provide the support for other formulation constituents, or there may be additional inert ingredients which provide such support. One example of an inert support ingredient that may be used in accordance with the present invention is ammonium sulfate. It will be recognized by one skilled in the art that as used herein, the term "dry" does not imply that dry formulations of the present invention are 100% free of water. Typically, dry formulations of the present invention comprise from about 0.5% to about 5% (by weight) water. It is preferred that the dry formulations of the present invention contain less than about 1% (by weight) water. Additionally, it is preferred for at least some embodiments that the particulate solid exhibits a dissolution rate of not more than about 5 minutes, about 4 minutes, about 3 minutes, about 2 minutes, or even about 1 minute.

Dry, water-soluble or water-dispersible formulations in accordance with the present invention can be produced by any process known in the art, including spray drying, fluid-bed agglomeration, pan granulation, or extrusion. In dry formulations, glyphosate may be present as a salt, or as an acid. Formulations containing glyphosate acid may optionally contain an acid acceptor such as an ammonium or alkali metal carbonate or bicarbonate, ammonium dihydrogen phosphate or the like so that upon dissolution or dispersion in water by the user a water-soluble salt of glyphosate is produced.

Also embraced by the present invention are liquid concentrate formulations having an aqueous phase wherein glyphosate is present predominantly in the form of a salt, and a non-aqueous phase optionally containing a second herbicidal active ingredient that is relatively water-insoluble. Such formulations illustratively include emulsions (including macro- and microemulsions, water-in-oil, oil-in-water and water-in-oil-in-water types), suspensions and suspoemulsions. The non-aqueous phase can optionally comprise a microencapsulated component, for example a microencapsulated herbicide. In formulations of the invention having a non-aqueous phase, the concentration of glyphosate a.e. in the composition as a whole is nonetheless within the ranges recited herein for aqueous concentrate formulations.

It is to be noted that the herbicidal spray compositions of the present invention are applied as aqueous solutions or dispersions, whether they are manufactured ready for application or result from the further dilution of a liquid glyphosate concentrate or the addition of water to a particulate solid glyphosate concentrate. However, the term "aqueous," as used herein, is not intended to exclude the presence of some small amount of non-aqueous solvent, so long as the predominant solvent present, is water. Herbicidal spray compositions, also known as tank-mixes, typically contain from about 0.5% to about 2% by weight per volume (w/v) percent glyphosate a.e. and more typically about 1% w/v a.e.

Application

Generally speaking, the present invention is additionally directed to a method of killing or controlling weeds or unwanted vegetation in a field containing a crop (e.g., of transgenic glyphosate-tolerant cotton plants having increased glyphosate tolerance in vegetative and reproductive tissues). In one embodiment, the method comprises the steps of diluting an aqueous glyphosate concentrate or diluting a solid particulate glyphosate concentrate in a suitable volume of water to form a tank mix, and applying a herbicidally effective amount of the tank mix to foliage of cotton plants genetically transformed to tolerate glyphosate, and simultaneously to foliage of weeds growing in close proximity to such plants. This method of use results in control of the weeds or unwanted vegetation while leaving the cotton plants substantially unharmed.

It should be understood that while the present invention is particularly directed to killing or controlling weeds or unwanted vegetation in a crop of transgenic glyphosate-tolerant cotton plants such as ROUNDUP READY and ROUNDUP READY FLEX cotton that are susceptible to PMIDA-induced leaf necrosis following over-the-top foliar application of glyphosate herbicides, the herbicidal glyphosate compositions and methods of weed control disclosed herein are not limited to such application and may be effectively employed generally in weed management to kill or control the growth of unwanted vegetation in cultivated crop lands as well as in other industrial and residential applications.

The practice of the present invention can be employed to kill or control the growth of a wide variety of unwanted plants, including annual and perennial grass and broadleaf weed species, by applying to the foliar tissues of the plants aqueous glyphosate compositions of the present invention. Particularly important annual dicotyledonous plant species include, without limitation, velvetleaf (*Abutilon theophrasti*), pigweed (*Amaranthus* spp.), buttonweed (*Borreria* spp.), oilseed rape, canola, indian mustard, etc. (*Brassica* spp.), commelina (*Commelina* spp.), filaree (*Erodium* spp.), sunflower (*Helianthus* spp.), morningglory (*Ipomoea* spp.), kochia (*Kochia scoparia*), mallow (*Malva* spp.), wild buckwheat, smartweed, etc. (*Polygonum* spp.), purslane (*Portulaca* spp.), Russian thistle (*Salsola* spp.), sida (*Sida* spp.), wild mustard (*Sinapis arvensis*) and cocklebur (*Xanthium* spp.).

Particularly important annual monocotyledonous plant species that may be killed or controlled using the compositions of the present invention include, without limitation, wild oat (*Avena fatua*), carpetgrass (*Axonopus* spp.), downy brome (*Bromus tectorum*), crabgrass (*Digitaria* spp.), barnyardgrass (*Echinochloa crus-galli*), goosegrass (*Eleusine indica*), annual ryegrass (*Lolium multiflorum*), rice (*Oryza sativa*), ottochloa (*Ottochloa nodosa*), bahiagrass (*Paspalum notatum*), canarygrass (*Phalaris* spp.), foxtail (*Setaria* spp.), wheat (*Triticum aestivum*) and corn (*Zea mays*).

Particularly important perennial dicotyledonous plant species for control of which a composition of the invention can be used include, without limitation, mugwort (*Artemisia* spp.), milkweed (*Asclepias* spp.), Canada thistle (*Cirsium arvense*), field bindweed (*Convolvulus arvensis*) and kudzu (*Pueraria* spp.).

Particularly important perennial monocotyledonous plant species for control of which a composition of the invention can be used include, without limitation, brachiaria (*Brachiaria* spp.), bermudagrass (*Cynodon dactylon*), yellow nutsedge (*Cyperus esculentus*), purple nutsedge (*C. rotundus*), quackgrass (*Elymus repens*), lalang (*Imperata cylindrica*), perennial ryegrass (*Lolium perenne*), guineagrass (*Panicum maximum*), dallisgrass (*Paspalum dilatatum*), reed (*Phragmites* spp.), johnsongrass (*Sorghum halepense*) and cattail (*Typha* spp.).

Other particularly important perennial plant species for control of which a composition of the invention can be used include, without limitation, horsetail (*Equisetum* spp.), bracken (*Pteridium aquilinum*), blackberry (*Rubus* spp.) and gorse (*Ulex europaeus*).

The herbicidal composition of the present invention is applied to plants at a rate sufficient to give the desired biological effects: control of weed growth without inducing significant leaf necrosis in cotton plants. These application rates are usually expressed as amount of glyphosate per unit area treated, e.g. grams per hectare (g/ha). What constitutes a "desired effect" varies according to the standards and practice of those who investigate, develop, market and use compositions and the selection of application rates that are herbicidally effective for a composition of the invention is within the skill of those skilled in the art. Typically, the amount of the composition applied per unit area to give 85% control of a weed species as measured by growth reduction or mortality is often used to define a commercially effective rate.

The selection of application rates that are herbicidally effective for a composition of the invention is within the skill of the ordinary agricultural scientist. Those of skill in the art will likewise recognize that individual plant conditions, weather and growing conditions, as well as the specific active ingredients and their weight ratio in the composition, will influence the degree of herbicidal effectiveness achieved in practicing this invention.

The herbicidal spray compositions included in the present invention can be applied to the foliage of the plants to be treated through any of the appropriate methods that are well known to those having skill in the art, including aerial application, and ground application techniques (e.g., a ground boom, a hand sprayer, rope-wick, etc.).

If desired, the user can mix one or more adjuvants with a composition of the invention and the water of dilution when preparing the application composition. Such adjuvants can include additional surfactant and/or an inorganic salt such as ammonium sulfate with the aim of further enhancing herbicidal efficacy.

Optional Formulation Components

Glyphosate formulations typically comprise adjuvants that enhance glyphosate herbicidal efficacy or otherwise enhance stability of the formulation. For example, glyphosate salts generally require the presence of a suitable surfactant to optimize uptake into the plant. As used herein, "surfactant" is intended to include a wide range of adjuvants that can be added to herbicidal glyphosate formulations to enhance the herbicidal efficacy thereof as compared to the efficacy of the glyphosate salt in the absence of such adjuvant. In particular, surfactants facilitate the translocation of glyphosate through the waxy leaf surface and into the plant. The surfactant can be provided in the formulation and/or can be added by the end user to a diluted spray composition.

Surfactant classes that have been formulated with glyphosate include cationics, nonionics, anionics, amphoterics, zwitterionics and mixtures thereof. Surfactants typically tending to provide the most useful glyphosate enhancement are generally, but not exclusively, cationic surfactants. Examples of cationic surfactant classes include alkylamine alkoxylates (including etheramines and diamines) such as tallowamine alkoxylate, cocoamine alkoxylate, etheramine alkoxylate, tallow ethylenediamine alkoxylate and amidoamine alkoxylates; alkylamine quaternary amines such as alkoxylated quaternary alkyl amines (e.g., ethoxylated quaternary alkyl amines or propoxylated quaternary alkyl amines); alkylamine acetates such as tallowamine acetate or octylamine acetate; amine oxides such as ethoxylated amine oxides (e.g., N,N-bis(2-hydroxyethyl)cocoamine-oxide), nonethoxylated amine oxides (e.g., cetyldimethylamine-oxide) and amidoamine oxides; and quaternary ammonium salts. Suitable cationic surfactants are described, for example, in U.S. Pat. Nos. 3,853,530, 5,750,468, 5,668,085, 5,317,003 and 5,464,807, European Patent No. 0274369, International Publication No. WO 95/33379, and U.S. Application Publication No. 2003/0104943 A1, the entire disclosures of which are incorporated herein by reference.

A preferred class of cationic surfactants commonly used in glyphosate formulations is ethoxylated alkylamines of formula (3):

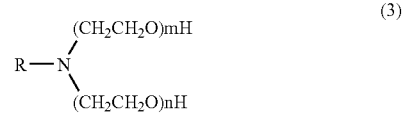

(3)

wherein m+n is between about 2 and about 25 and R is a branched or straight chain alkyl group having from about 12 to about 22 carbon atoms. Preferably, R is a coco or tallow group. Examples of such alkylamines include TRYMEEN 6617 (from Cognis) and ETHOMEEN C/12, C/15, C/20, C/25, T/12, T/15, T/20 and T/25 (from Akzo Nobel) where "C" indicates R being coco and "T" indicates R being tallow.

Another preferred class of cationic surfactants commonly used in glyphosate formulations are etheramines such as those described in U.S. Pat. No. 5,750,468 including those of the following formulae (4) to (6):

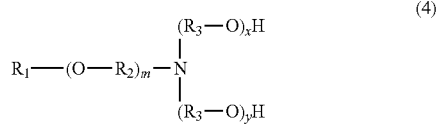

wherein $R_1$ is a straight or branched chain $C_6$ to about $C_{22}$ alkyl, aryl or alkylaryl group, m is an average number from 1 to about 10, $R_2$ in each of the m (O—$R_2$) groups is independently $C_1$-$C_4$ alkylene, $R_3$ groups are independently $C_1$-$C_4$ alkylene, and x and y are average numbers such that x+y is in the range from 2 to about 60;

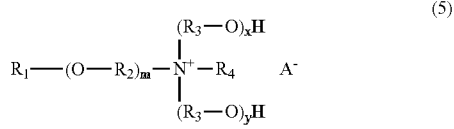

wherein $R_1$ is a straight or branched chain $C_6$ to about $C_{22}$ alkyl, aryl or alkylaryl group, m is an average number from 1 to about 10, $R_2$ in each of the m (O—$R_2$) groups is independently $C_1$-$C_4$ alkylene, $R_3$ groups are independently $C_1$-$C_4$ alkylene, $R_4$ is $C_1$-$C_4$ alkyl, x and y are average numbers such that x+y is in the range from 0 to about 60, and A- is an agriculturally acceptable anion;

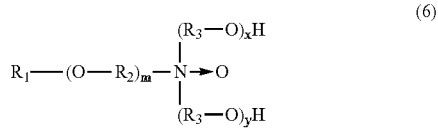

wherein $R_1$ is a straight or branched chain $C_6$ to about $C_{22}$ alkyl, aryl or alkylaryl group, m is an average number from 1 to about 10, $R_2$ in each of the m (O—$R_2$) groups is independently $C_1$-$C_4$ alkylene, $R_3$ groups are independently $C_1$-$C_4$ alkylene, and x and y are average numbers such that x+y is in the range from 2 to about 60.

Examples of preferred nonionic surfactants include alkylpolyglucosides, glycerol esters, ethoxylated glycerol esters, ethoxylated castor oil, ethoxylated reduced sugar esters, polyhydric alcohol esters, ethoxylated amides, ethoxylated polyethylene glycol esters, ethoxylated alkyl phenols, ethoxylated arylphenols, fatty alcohol ethoxylates, ethylene oxide copolymers, propylene oxide copolymers, organosilicones, fluoro-organics and mixtures thereof.

Examples of preferred anionic surfactants include polyalkoxylated phosphate esters and diesters; fatty soaps such as ammonium tallowate and sodium stearate; alkyl sulfates such as sodium $C_{8-10}$ alcohol sulfate, sodium oleyl sulfate, and sodium lauryl sulfate; sulfated oils such as sulfated castor oil; ether sulfates such as sodium lauryl ether sulfate, ammonium lauryl ether sulfate, and ammonium nonylphenol ether sulfate; sulfonates such as petroleum sulfonates, alkylbenzene sulfonates (e.g., sodium (linear) dodecylbenzene sulfonate or sodium (branched) dodecylbenzene sulfonate), alkylnapthalene sulfonates (e.g., sodium dibutylnapthalene sulfonate), alkyl sulfonates (e.g., alpha olefin sulfonates), sulfosuccinates such as dialkylsulfosuccinates (e.g., sodium dioctylsulfosuccinate) and monoalkylsulfosuccinate and succinamides (e.g., disodium laurylsulfosuccinate and disodium N-alkylsulfosuccinamate); sulfonated amides such as sodium N-methyl N-coco taurate; isethionates such as sodium cocoyl isethionate; N-acyl sarcosinates such as N-lauroyl sarcosine, sodium lauryl sarcosinate, sodium cocoyl sarcosinate and sodium myristoyl sarcosinate; and phosphates such as alkylether ethoxylate phosphates and alkylarylether ethoxyated phosphates; saturated carboxylic and fatty acids such as butyric, caproic, caprylic, capric, lauric, palmitic, myristic or stearic acid; and unsaturated carboxylic acids such as palmitoleic, oleic, linoleic or linoleic acid.

Exemplary amphoteric surfactants include betaines such as simple betaines (e.g., cocodimethylbetaine), sulfobetaines, amidobetaines, and cocoamidosulfobetaines; imidazolinium compounds such as disodium lauroamphodiacetate, sodium cocoamphoacetate, sodium cocoamphopropionate, disodium cocoaminodipropionate, and sodium cocoamphohydoxypropyl sulfonate; and other amphoteric surfactants such as alkyl hydroxyethylglycines (e.g., N-alkyl, N,-bis(2-hydroxyethyl) glycine) and alkylaminedipropionates.

A glyphosate formulation of the invention can comprise any combination of the surfactants described above so long as the surfactant does not induce significant leaf necrosis in cotton plants when it is formulated in the glyphosate composition. In one combination described in International Publication No. WO 00/15037, an alkylpolyglycoside surfactant is combined with an alkoxylated alkylamine surfactant. Such a surfactant combination can be used in a glyphosate composition of the present invention and applied to transgenic glyphosate-tolerant cotton plants without inducing significant leaf necrosis if the PMIDA content of the composition is controlled and/or a PMIDA safener is added to the glyphosate composition (e.g., a humectant, metal ions, light absorber, or antioxidant).

Other additives and adjuvants typically employed in glyphosate formulations can be combined with or included in the glyphosate compositions of the present invention. For instance, urea, ammonium sulfate, viscosity modifiers, dispersants, organic solvents, glycols, buffers, antifoam agents, di-carboxylic acids and/or polycarboxylic acids are all suitable additives.

Optionally, one or more of the compositions of the present invention may further comprise one or more additional pesticides, such as for example, water-soluble herbicidal active ingredients or water-insoluble herbicidal active ingredients, including without restriction acifluorfen, asulam, benazolin, bentazon, bialaphos, bispyribac, bromacil, bromoxynil, carfentrazone, chloramben, 2,4-D, 2,4-DB, dalapon, dicamba, dichlorprop, diclofop, difenzoquat, diquat, endothall, fenac, fenoxaprop, flamprop, fluazifop, fluoroglycofen, fomesafen, fosamine, glufosinate, haloxyfop, imazameth, imazamethabenz, imazamox, imazapic, imazapyr, imazaquin, imazethapyr, ioxynil, MCPA, MCPB, mecoprop, methylarsonic acid, naptalam, nonanoic acid, paraquat, sulfamic acid, 2,3,6-TBA, TCA, acetochlor, aclonifen, alachlor, ametryn, amidosulfuron, anilofos, atrazine, azafenidin, azimsulfuron, benfluralin, benfuresate, bensulfuron-methyl, bensulide, benzofenap, bifenox, bromobutide, bromofenoxim, butachlor, butamifos, butralin, butroxydim, butylate, cafenstrole, carbetamide, carfentrazone-ethyl, chlomethoxyfen, chlorbromuron, chloridazon, chlorimuron-ethyl, chlornitrofen, chlorotoluron, chlorpropham, chlorsulfuron, chlorthaldimethyl, chlorthiamid, cinmethylin, cinosulfuron, clethodim, clodinafop-propargyl, clomazone, clomeprop, cloransulam-methyl, cyanazine, cycloate, cyclosulfamuron, cycloxydim, cyhalofop-butyl, daimuron, desmedipham, desmetryn, dichlobenil, diclofop-methyl, diflufenican, dimefuron, dimepiperate, dimethachlor, dimethametryn, dimethenamid, dinitramine, dinoterb, diphenamid, diuron, EPTC, esprocarb, ethalfluralin, ethametsulfuron-methyl, ethofumesate, ethoxysulfuron, etobenzanid, fenoxaprop-ethyl, fenuron, flamprop-methyl, flazasulfuron, fluazifop-butyl, fluchloralin, flumetsulam, flumiclorac-pentyl, flumioxazin, fluometuron, fluorochloridone, fluoroglycofen-ethyl, flupoxam, flurenol, fluridone, flurtamone, fluthiacet-methyl, fomesafen, halosulfuron, haloxyfop-methyl, hexazinone, imazosulfuron, indanofan, isoproturon, isouron, isoxaben, isoxaflutole, isoxapyrifop, lactofen, lenacil, linuron, mefenacet, metamitron, metazachlor, methabenzthiazuron, methyldymron, metobenzuron, metobromuron, metolachlor, metosulam, metoxuron, metribuzin, metsulfuron, molinate, monolinuron, naproanilide, napropamide, naptalam, neburon, nicosulfuron, norflurazon, orbencarb, oryzalin, oxadiargyl, oxadiazon, oxasulfuron, oxyfluorfen, pebulate, pendimethalin, pentanochlor, pentoxazone, phenmedipham, piperophos, pretilachlor, primisulfuron, prodiamine, prometon, prometryn, propachlor, propanil, propaquizafop, propazine, propham, propisochlor, propyzamide, prosulfocarb, prosulfuron, pyraflufen-ethyl, pyrazolynate, pyrazosulfuronethyl, pyrazoxyfen, pyributicarb, pyridate, pyriminobac-methyl, quinclorac, quinmerac, quizalofop-ethyl, rimsulfuron, sethoxydim, siduron, simazine, simetryn, sulcotrione, sulfentrazone, sulfometuron, sulfosulfuron, tebutam, tebuthiuron, terbacil, terbumeton, terbuthylazine, terbutryn, thenylchlor, thifensulfuron, thiobencarb, tiocarbazil, tralkoxydim, triallate, triasulfuron, tribenuron, trietazine, trifluralin, triflusulfuron and vernolate.

In one embodiment, a glyphosate concentrate or spray composition is prepared from a manufactured technical grade glyphosate product comprising at least about 90, 91, 92, 93, 94, 95, 96, 97, 98 or 99 wt. % glyphosate acid equivalent (a.e.); less than about 0.05, 0.06, 0.07, 0.08, 0.09, 0.10, 0.20, 0.30, 0.40, 0.50 or 0.60 wt. % PMIDA (on an acid equivalent basis); and aminomethylphosphonic acid (AMPA), wherein the weight ratio of PMIDA to AMPA is not more than 0.18:1, 0.19:1, 0.20:1, 0.21:1, 0.22:1, 0.23:1, 0.24:1, or 0.25:1, the weight percentages being on a dry basis. Preferably the glyphosate concentration is at least about 95 wt. % on an acid equivalent basis.

In another embodiment, a glyphosate concentrate or spray composition is prepared from a manufactured technical grade glyphosate product comprising at least about 90, 91, 92, 93, 94, 95, 96, 97, 98 or 99 wt. % glyphosate acid equivalent (a.e.); less than about 0.05, 0.06, 0.07, 0.08, 0.09, 0.10, 0.11, 0.12, 0.13, 0.14 or 0.15 wt. % PMIDA (on an acid equivalent basis); and a by-product selected from not more than about 0.2, 0.3, 0.4, 0.5, 0.6, or 0.7 wt. % N-formyl glyphosate (NFG) or not more than about 0.01, 0.02 or 0.03 wt. % N-methyl iminodiacetic acid (NMIDA), the weight percentages being on a dry basis. Preferably the glyphosate concentration is at least about 95 wt. % on an acid equivalent basis.

An aqueous herbicidal concentrate composition of the invention, for example, comprises at least about 360, 370, 380, 390, 400, 410, 420, 430, 440, 450, 460, 470, 480, 490, 500, 510, 520, 530, 540, 550, 560, 570, 580, 590 or 600 or more grams glyphosate per liter (on an acid equivalent basis), less than about 0.3, 0.35, 0.4, 0.5, 0.6, 0.7, 0.8, 0.9, 1, 2, 3, 4 or 5 grams per liter (on an acid equivalent basis) of PMIDA, and AMPA, wherein the weight ratio of PMIDA to AMPA is not more than 0.25:1.

In another embodiment, an aqueous herbicidal concentrate composition comprises at least about 360, 370, 380, 390, 400, 410, 420, 430, 440, 450, 460, 470, 480, 490, 500, 510, 520, 530, 540, 550, 560, 570, 580, 590 or 600 or more grams glyphosate per liter (on an acid equivalent basis), less than about 0.3, 0.35, 0.4, 0.5, 0.6, 0.7, 0.8, 0.9, 1, 2, 3, 4 or 5 grams per liter (on an acid equivalent basis) of PMIDA, and at least one surfactant other than an alkoxylated alkyl amine or an alkoxylated phosphate ester.

In one embodiment, the glyphosate herbicidal composition in accordance with the present invention is in the form of an aqueous concentrate and comprises glyphosate (e.g., N-(phosphonomethyl)glycine or an agronomically acceptable salt thereof), PMIDA, a surfactant component comprising a cationic surfactant and a metal ion safening agent which forms a complex or salt in the composition with PMIDA or an anion formed by deprotonation or partial deprotonation thereof. The molar ratio of the metal ion safening agent comprising one or more metal ions to PMIDA acid equivalent is typically at least about 0.4:1, at least about 0.45:1, at least about 0.5:1, at least about 0.55:1, at least about 0.6:1, at least about 0.65:1, at least about 0.7:1, at least about 0.75:1, at least about 0.8:1, at least about 0.85:1, at least about 0.9:1 or at least about 0.95:1. Preferably, the concentration PMIDA in the manufactured technical grade glyphosate product from which such concentrates are formulated is managed below about 3000 ppm, more preferably from about 1200 to about 2500 ppm, such that effective safening of the concentrate composition is achieved at molar ratio of metal ion safening agent to PMIDA acid equivalent of from about 1:1 to about 6:1, from about 1:1 to about 5:1, from about 1:1 to about 4:1, from about 1:1 to about 3:1, from about 1:1 to about 2.5:1 and preferably from about 1:1 to about 2:1.

In such aqueous concentrate formulations, the glyphosate is preferably predominantly present in the form of an agronomically acceptable salt of N-(phosphonomethyl)glycine selected from the group consisting of alkali metal salts, alkylamine salts, and mixtures or combinations thereof. In accordance with one especially preferred embodiment, the glyphosate is predominantly present in the form of the potassium salt and the concentration of the glyphosate salt is at least about 360, 370, 380, 390, 400, 410, 420, 430, 440, 450, 460, 470, 480, 490, 500, 510, 520, 530, 540, 550, 560, 570, 580, 590 or 600 or more grams per liter on an acid equivalent basis. Examples of preferred cationic surfactant components for use in such concentrates include the ethoxylated alkylamines of formula (3) and the etheramines of formulae (4) to (6). Preferably, the metal ion safening agent comprises polyvalent iron (e.g., Fe(III)) and may be suitably derived from ferric sulfate and combined with citric acid as a solubilizing ligand in the concentrate composition as described above. Alternatively, iron citrate may be used in the formulation of such iron ion-safened concentrates.

Glyphosate Manufacturing Processes

In a preferred process for the manufacture of glyphosate, an aqueous solution of N-(phosphonomethyl)iminodiacetic acid (PMIDA) is contacted with an oxidizing agent in the presence of a catalyst. The catalyst may be, for example, a particulate activated carbon as described by Chou in U.S. Pat. No. 4,624,937, a noble metal on carbon catalyst as described by Ebner et al. in U.S. Pat. No. 6,417,133, or a transition metal/nitrogen composition on carbon as described in U.S. Application Publication No. U.S. 2004/0010160 A1; International Publication No. WO 2005/016519 A1; and in copending and co-assigned U.S. application Ser. No. 11/357,900, filed Feb. 17, 2006, entitled TRANSITION METAL-CONTAINING CATALYSTS AND CATALYST COMBINATIONS INCLUDING TRANSITION METAL-CONTAINING CATALYSTS AND PROCESSES FOR THEIR PREPARATION AND USE AS OXIDATION CATALYSTS, all of which are expressly incorporated herein by reference.

Conventionally, the oxidation reaction is conducted in one or more stirred tank reactors wherein the catalyst is slurried in an aqueous solution of PMIDA. The reactor(s) may be operated in either a batch or continuous mode. Where reaction is conducted in a continuous mode, the aqueous reaction medium may be caused to flow through a plurality of continuous stirred tank reactors (CSTRs) in series. The oxidizing agent is preferably molecular oxygen, though other oxidants such as, for example, hydrogen peroxide or ozone, may also be used. Where molecular oxygen is used, the reaction is conveniently conducted at a temperature in the range from about 70° C. to about 140° C., more typically in the range from about 80° C. to about 120° C. Where a particulate noble metal catalyst is used, it is typically slurried in the reaction solution at a concentration of from about 0.5% to about 5% by weight.

In a series of CSTRs, the temperature of each reactor is independently controlled, but typically each reactor is operated in substantially the same temperature range as the other(s). Preferably, the temperature is controlled at a level which maintains glyphosate in solution and achieves substantial oxidation of by-product formaldehyde and formic acid, without excessive formation of either by-product iminodiacetic acid (IDA), which typically results from oxidation of PMIDA, or by-product aminomethylphosphonic acid (AMPA), which typically results from oxidation of glyphosate. Formation of each of these by-products tends to increase with temperature, with IDA formation occurring principally in the first or second reactor where PMIDA concentration is high, and AMPA being formed principally in the last or penultimate reactor where glyphosate concentration is relatively high. Where the oxidant is molecular oxygen, it may be introduced independently into one or more, preferably all, of the series of CSTRs. Typically, the oxygen pressure may be in the range of from about 15 to about 300 psig, more typically in the range of from about 40 to about 150 psig. Where CSTRs are arranged for cascaded flow without intermediate transfer pumps, the pressure in each successive CSTR is preferably lower than the pressure in the immediately preceding CSTR so as to assure a positive differential for promoting forward flow. Typically, oxygen pressure in the first of a series of CSTRs is operated an a level approximating its pressure vessel rating, while each of the remaining reactors in the series are operated at a pressure that is within its rating but also sufficiently below the pressure prevailing in the immediately preceding reactor to ensure forward flow. For example, in a system comprising three such reactors in series, the first reactor might be operated at a pressure in the range of from about 105 to about 125 psig, the second reactor at from about 85 to about 100 psig and the third reactor at from about 60 to about 80 psig.

A process comprising a series of CSTRs for production of glyphosate is illustrated in FIG. 1. Catalytic oxidation of PMIDA is conducted in a series of CSTRs 101 to 105 in each of which an aqueous solution of PMIDA is contacted with molecular oxygen in the presence of a particulate catalyst slurried in the aqueous medium. A reaction slurry exiting the final CSTR 105 is directed to a catalyst filter 107 wherein particulate catalyst is removed for recycle to the reaction system. For recovery of glyphosate product, filtered reaction solution is divided between a vacuum crystallizer 109, typically operated without substantial heat input (i.e., adiabatically) and an evaporative crystallizer 111 wherein water is driven off the aqueous phase by transfer heat from a heat transfer fluid such as steam. A crystallization slurry 113 produced in vacuum crystallizer 109 is allowed to settle, and the supernatant mother liquor 115, which contains some unreacted PMIDA, is decanted and may be recycled to the reaction system, typically to CSTR 101. A solid technical grade glyphosate product may be recovered from the underflow slurry 117 exiting the decantation step. According to the optional process alternative illustrated in FIG. 1, the concentrated vacuum crystallizer slurry 117 underflowing from the decantation is divided into two fractions. One fraction 119 is mixed with the crystal slurry exiting the evaporative crystallizer 111 and directed to a centrifuge 121 which separates a solid, crystalline technical grade glyphosate acid product that may be used or sold in the form of the solid wet centrifuge cake. The other vacuum crystallizer underflow slurry fraction 123 is directed to another centrifuge 125 which separates a solid crystalline product that is used to prepare a concentrated glyphosate salt solution. For this purpose, solids exiting centrifuge 125 are directed to a salt makeup tank 127 where they are neutralized with a base such as potassium hydroxide (KOH) or isopropylamine in an aqueous medium to a typical concentration of from about 400 to 650 grams per liter, acid equivalent.

Mother liquor 129 from centrifuge 125 typically contains PMIDA in a proportion sufficient to justify recycle thereof to reactor 101. Mother liquor 131 from centrifuge 121 is divided into a purge fraction 133 which is removed from the process, and a recycle fraction 135 which is returned to evaporative crystallizer 111.

In addition to unreacted PMIDA, the reaction solution typically contains small proportions of other impurities that are innocuous but generally ineffective as herbicides, and which can compromise the crystallization step and/or reduce productivity. These must ultimately be removed from the process, in part via purge 133 and in part as minor components of glyphosate products. To balance the proportion of impurities purged in fraction 133 with those removed in the concentrated aqueous salt product, a mother liquor transfer line 139 is provided for optional transfer of mother liquor from line 135 to neutralization tank 127.

Figure 2:
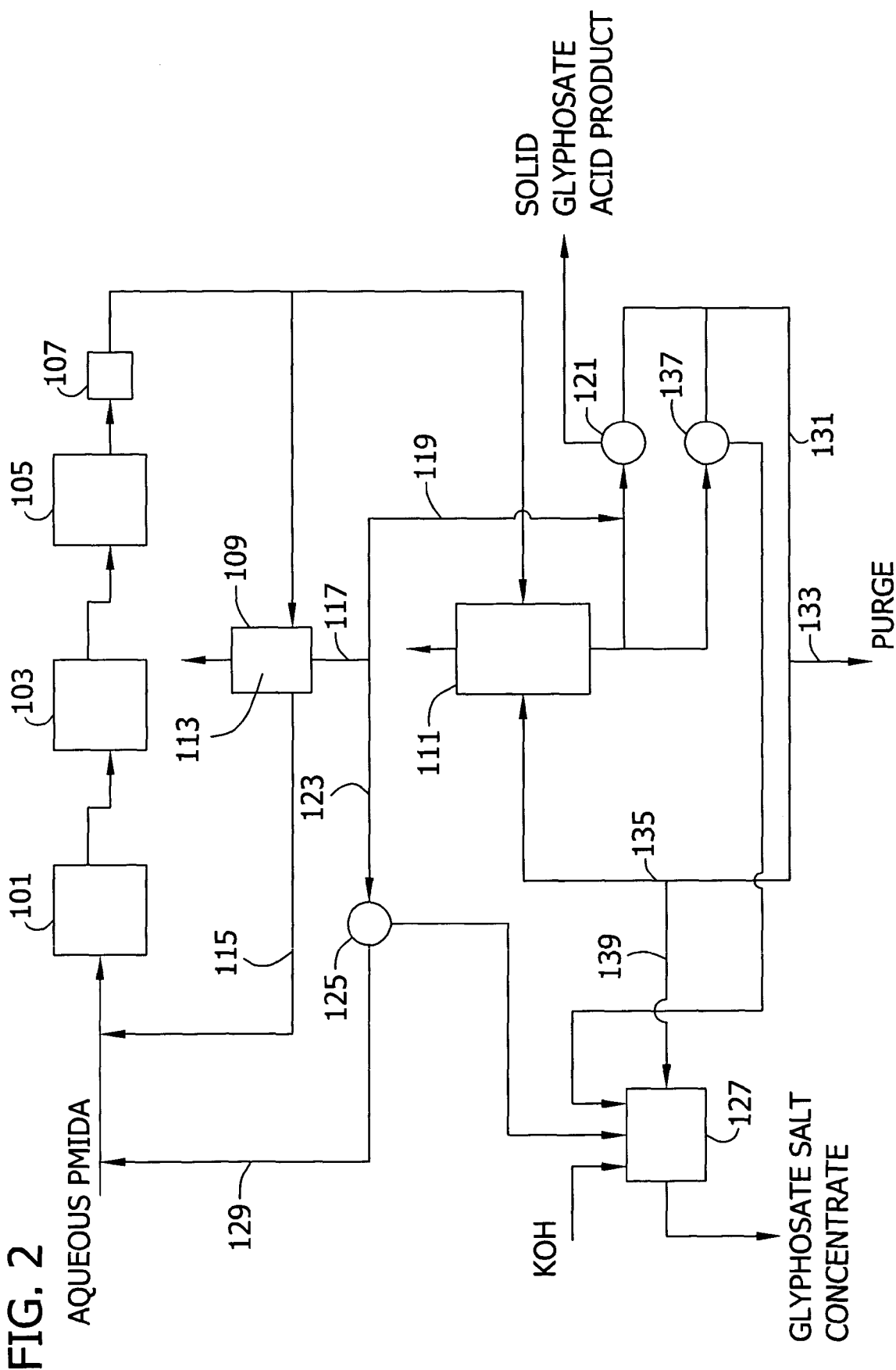
FIG. 2 is a schematic flow sheet illustrating an alternative embodiment of the process of FIG. 1 in which N-(phosphonomethyl)iminodiacetic acid that accumulates in the product recovery area can be removed from the process in a controlled manner, more particularly in a manner that allocates N-(phosphonomethyl)iminodiacetic acid removal between a solid glyphosate acid product, a concentrated glyphosate salt solution, and a purge stream.

FIG. 2 illustrates a modest refinement of the process of FIG. 1 wherein the crystal slurry exiting evaporative crystallizer 111 is divided between centrifuge 121 and a parallel centrifuge 137. The centrifuge wet-cake from centrifuge 121 is removed from the process and may be utilized or sold as a solid technical grade glyphosate product, but the wet-cake from centrifuge 137 is directed to tank 127 for use in preparing a glyphosate salt concentrate. The mother liquor draining from both centrifuges 121 and 137 is combined as stream 131 which is divided between purge stream 133 and stream 135 which is recycled to the evaporative crystallizer.

In operation of the continuous oxidation process depicted in FIGS. 1 and 2, a slurry comprising an aqueous solution typically comprising from about 6.5% to about 11% by weight PMIDA is introduced continuously into CSTR 101. The aqueous reaction medium formed in CSTR 101 may typically contain from about 2% to about 5% by weight of a particulate noble metal catalyst suspended therein. For example, the catalyst may comprise a bifunctional noble metal on carbon catalyst as described in U.S. Pat. Nos. 6,417,133, 6,603,039, 6,586,621, 6,963,009, and 6,956,005 and published U.S. Application Publication No. 2006/0020143, which are expressly incorporated herein by reference. A source of oxygen, e.g., air, or preferably oxygen enriched air or substantially pure oxygen, is sparged into the aqueous reaction medium within reactor 101 at pressure in the range from about 105 to about 125 psig and reaction is typically conducted at a temperature in the range from about 900 to about 115° C. Typically, a PMIDA conversion to glyphosate in the range of about 82% to about 85% is realized in reactor 101. Reaction solution containing slurried catalyst exiting CSTR 101 flows to second stage CSTR 103 which is operated under substantially the same temperature conditions as CSTR 101, but with oxygen sparged at an oxygen pressure in the range from about 85 to about 100 psig. PMIDA conversion achieved at the exit of reactor 103 is typically in the range from about 90% to about 97% (i.e., conversion within the second reactor is from about 8% to about 15%, basis, the PMIDA charged to reactor 101).

Reaction solution with slurried catalyst exiting CSTR 103 flows to a third CSTR 105. Oxygen is sparged into reactor 105 at a pressure in the range of from about 60 to about 80 psig. Typically, the temperature of the reaction solution in reactor 105 is maintained in substantially the same range as in reactors 101 and 103. PMIDA conversion in reactor 103 is typically 3% to 5%, basis the PMIDA entering reactor 101, resulting in an overall PMIDA conversion in the continuous reaction system from about 97% to about 99.5%.

Reactors 101 through 105 are vented under feed back pressure control. In a preferred mode of operation, the flow rate of oxygen to each reactor is controlled to establish and maintain a target consumption of the oxygen that is introduced into the reactor in the oxidation of PMIDA and reaction by-products such as formaldehyde and formic acid. The proportionate consumption of oxygen introduced into the reactor is referred to herein as the oxygen utilization. In conventional operation, the pressure is preferably established at a level that provides an oxygen utilization of at least 60%, preferably at least about 80%, more preferably at least about 90%. Consistent with the preferred oxygen utilization, the oxygen feed is divided among a series of CSTRs generally in proportion to the reaction rate prevailing in each of the reactors. Preferably, the reactors are sized to provide a residence time effective to accomplish a substantial fraction of the conversion in the first of a series of, e.g., three CSTRs. For example, 65% to 80% of the oxygen may be fed to the first of three reactors, 20% to 30% to the second, and 1% to 5% to the third. Typically, reaction in all but the last of a series of CSTRs is mass transfer limited, i.e., pseudo zero order. Under finishing conditions in the last reactor, the reaction is non-zero order, e.g., approximately first order. As discussed hereinbelow, as the catalyst mass ages, deactivates, conversion may be maintained by increasing the oxygen flow rates, at the same or different allocations of oxygen among reactors (e.g., in the process of FIGS. 1 and 2 by increasing the proportion of oxygen introduced into reactor 101 or 103), to accomplish more of the conversion in the reactors upstream of the last reactor.

Where the oxygen utilization is relatively high, especially where it is greater than about 80% or about 90%, it has been found that the PMIDA content of the effluent from the final reactor is typically in the range of from about 800 to 1300 ppm on a total reaction solution basis. Where glyphosate is recovered by crystallization from the reaction solution in the manner described above, the PMIDA content of the glyphosate product(s) is generally substantially higher than in the product reaction solution exiting reactor 105. Due to recycle of mother liquor containing PMIDA, the aqueous crystallizer feed solutions from which glyphosate is crystallized generally contain PMIDA in a ratio to glyphosate that is at least 25% higher, or in various steady state operations at least 50% higher, than the ratio of PMIDA to glyphosate in the product reaction solution. The extent of PMIDA buildup is limited by the volume of purge fraction 133. However, when a process of the type illustrated in FIGS. 1 and 2 has reached substantially steady state operation, a PMIDA range of from about 800 to about 2500 ppm in the final reaction solution may typically translate into a concentration of 2000 to 6000 ppm in the final glyphosate product, provided that a purge stream is provided in which a reasonable fraction, perhaps up to 10%, of the PMIDA contained in the reaction solution is purged from the process. Where more than one form of product is produced (e.g., where product is provided in both the form of solid technical grade glyphosate product and a concentrated solution of a glyphosate salt) the PMIDA content may vary between the plural products, depending in part on the direction and division of various process streams in the product recovery scheme.

It will be understood that a variety of other schemes may be used for the preparation of a glyphosate reaction solution by the catalyzed oxidation of a PMIDA substrate and for recovery of a technical grade glyphosate product(s) from a glyphosate reaction solution in the form of a solid and/or a concentrated glyphosate salt solution. For example, the filtered reaction solution may all be directed to an evaporative crystallizer and the product recovered from the crystallizer slurry in a filter or centrifuge for use either as glyphosate acid or in the preparation of a concentrated salt solution. In such process, the mother liquor may be divided into a purge fraction and a fraction which is recycled to the evaporative crystallizer. Alternatively, all or a portion of the mother liquor which is not purged may be recycled to the reaction system. Various oxidation reaction systems for the catalytic oxidation of a PMIDA substrate and alternative process schemes for recovering technical grade glyphosate product from the oxidation reaction solution, including schemes utilizing adiabatic vacuum crystallization, are known and described, for example, by Haupfear et al. in U.S. Application Publication Nos. U.S. 2002/0068836 A1 and U.S. 2005/0059840 A1, the entire contents of which are expressly incorporated herein by reference.

Modifications in PMIDA Oxidation Reaction Conditions and Systems

In accordance with the present invention, it has been discovered that oxygen flow to the reactor(s) may be optionally adjusted in a manner that reduces the concentration of PMIDA in the final reaction solution, resulting in a generally proportionate decrease in the PMIDA content of the recovered glyphosate product or products. Generally, it has been found that increasing oxygen flow in one or more of the reactors enhances the conversion of PMIDA to glyphosate. The exact relationship of oxygen flow to PMIDA conversion varies significantly with the other conditions of the process, with the nature of the catalyst, with catalyst age and concentration, with batch vs. continuous operation, with product throughput, and with the peculiarities of the configuration a specific reactor, its oxygen feed point, agitation system and gas flow patterns. However, those skilled in the art can readily adjust the oxygen flow rate for a specific reactor or series of reactors to obtain a desired response in increased conversion of PMIDA. By way of example, where a continuous reaction system of the type illustrated in FIG. 1 is operating at a residual PMIDA level of 800 to 1500 ppm in the reaction solution exiting CSTR 105, the PMIDA content of the product reaction solution may be reduced to from about 150 to about 250 ppm by a proportionate increase in the sum of the oxygen flow rates to reactors 101 to 105 of roughly from about 0.1 to about 2% relative to the sum of flow rates that yields a PMIDA content of 800 ppm under otherwise identical process conditions. Alternatively, such reduction in PMIDA content of the product reaction solution may be achieved by increasing the flow rate of oxygen to the last of the series of reactors, reactor 105, by at least about 5%, typically from about 10% to about 30% relative to the flow rate which yields a PMIDA content of 800 ppm under otherwise identical reaction conditions.

Over an extended period of operations, the catalyst may deactivate to the extent that desired conversion can no longer be achieved by adjustment of oxygen flow to the last of a series of CSTRs. However, up to a limit defined by useful catalyst life (or at augmentation or partial replacement with fresh catalyst), the desired conversion can still be maintained by progressively increasing the oxygen flow to the earlier reactors, e.g., reactors 101 and 103 in FIGS. 1 and 2. Preferably, the oxygen flow rate is increased sufficiently to actually increase the conversion in the reaction solution exiting the penultimate reactor, so that the duty imposed on the last reactor is reduced. Thus, the desired ultimate conversion is obtained even though the productivity of the last reactor per se has declined. Conversion can also be increased by increasing residence time in the reactors. As those skilled in the art will appreciate, an infinite number of combinations of flow rates to the respective reactors may be available to achieve the desired level of PMIDA in the product reaction solution.

It has further been discovered that maintaining a desired PMIDA content in the reaction solution exiting the final reactor can be facilitated by selection of the system for monitoring the composition of the reaction solution. In a particularly preferred embodiment of the invention, the composition of the reaction solution exiting the final reactor is monitored by passing the reaction solution, or a sample of such solution, through a device of the type described in co-assigned U.S. provisional application Ser. No. 60/667,783, filed Apr. 1, 2005, entitled CONTROL OF PMIDA CONVERSION IN MANUFACTURE OF GLYPHOSATE. For example, the conversion can be estimated by cumulative heat generation arising from the oxidation of PMIDA, by the instantaneous rate of heat generation, or combination of both. From the instantaneous rate, the conversion and rate constant may also be inferred in the manner described in the aforesaid application, particularly if analyzed in combination with laboratory kinetic data and historical operational process data. Other methods for monitoring conversion include measuring the cumulative or instantaneous oxygen consumption, and/or the cumulative and/or instantaneous rate of carbon dioxide generation, and/or a function of the power consumed in maintaining a select current density, or a select potential difference between electrodes immersed in the reaction solution. A device useful for the latter purpose comprises a pair of electrodes immersed in the reaction solution or a sample thereof, and is controlled to maintain a select current density or impose a select voltage or schedule of voltages between the electrodes. In the latter instance, the device typically comprises a third electrode function as a reference electrode for use in maintaining the desired voltage. Where the device is controlled to maintain a select current density, the voltage required to maintain the current is indicative of the residual PMIDA content in the solution. As long as PMIDA is present, and the current is established at a level sufficient to consume $C_1$s such as formaldehyde and formic acid, the requisite voltage may approximate that required for the electrochemical oxidation of PMIDA. As PMIDA is exhausted, the voltage increases to a level effective for electrochemical oxidation of glyphosate. Where a select voltage or schedule of voltages is applied, the current observed at a voltage effective for electrochemical oxidation of PMIDA is indicative of residual PMIDA content. In the process of FIGS. 1 and 2, such an electrochemical oxidation probe is conveniently located in the stream exiting the catalyst filter 107, preferably following a polishing filter downstream of the catalyst filter which is effective for removal of catalyst fines.

Figure 3:
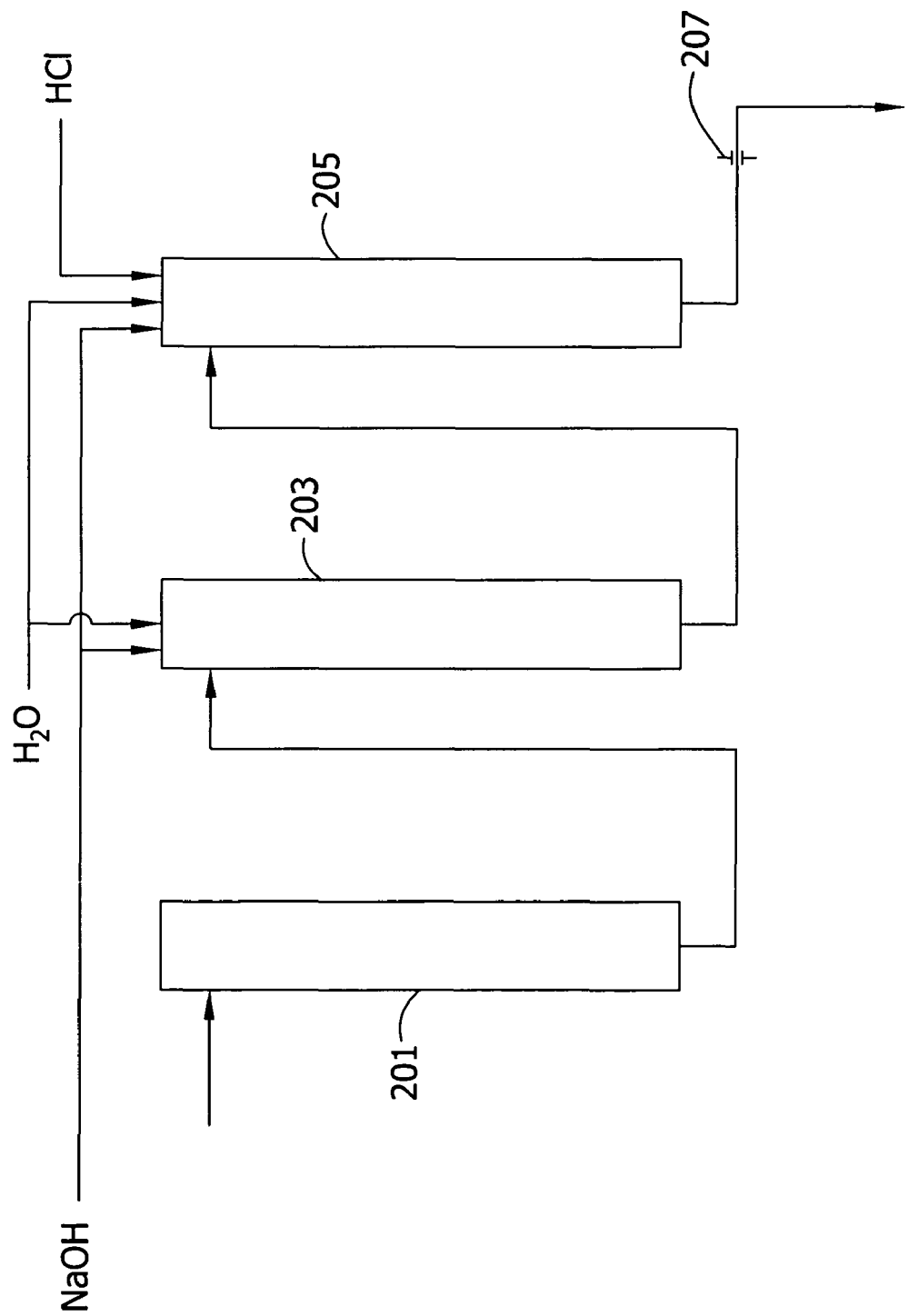
FIG. 3 is a schematic flow sheet illustrating an exemplary ion exchange system, which may be used in conjunction with the process for the manufacture of glyphosate illustrated in FIG. 1 or 2.

In a further advantageous embodiment of the process of the invention, cumulative or instantaneous heat generation, oxygen consumption, or carbon dioxide generation, or an electrochemical oxidation probe are monitored and used to estimate the conversion in and/or composition of the reaction solution exiting the next to last reactor (reactor 103 in FIGS. 1 and 2), and/or the third last reactor (i.e., reactor n−2 in a series of n reactors; e.g., reactor 101 in FIGS. 1 and 3). Where an electrochemical oxidation probe is used in the third last reactor, it is preferably operated to maintain a target current density. By periodically reversing the polarity, the electrodes are kept clean in the catalyst slurry environment. Optionally, further intelligence for controlling PMIDA levels exiting the reaction system may be provided by application of mathematical models which project conversions based on input of current process signals into a program based on first principles and/or historical operating data. By these means, the process operator, or a process management control system, can increase the oxygen flow to the earlier reactor or reactors as the catalyst mass deactivates, thereby reducing the demand on the final reactor and achieving the desired conversion and residual PMIDA content in the solution exiting the last reactor.

In a batch reaction system, the PMIDA content of the reaction solution may optionally be reduced by extending the cycle during which a source of oxygen is sparged into the aqueous reaction medium. For a given operation, a conventional oxygen flow cycle may be identified by any convenient conventional means, as, for example, by periodic analysis of samples from the reactor. Where performance as a function of time is reasonably consistent, timing of the batch may be sufficient and sampling may not be necessary. In any case, it has been discovered that, by extending the oxygen sparging cycle by from about 2 to about 15 minutes, more typically from about 5 to about 10 minutes, PMIDA conversion can be increased to reduce residual PMIDA content from a range from about 275 to about 350 ppm to a range from about 50 to about 100 ppm or even lower.

Because the oxidation reaction is exothermic, means are provided for transfer of reaction heat from the reaction mixture in the reactor(s) under feedback temperature control. Thus, if a cooling fluid such as cooling tower water is passed through a heat exchanger (e.g., cooling coils) for controlling the reaction temperature, the extent of reaction can be estimated from the cumulative heat dissipation over the batch cycle, as may be determined from an integrated average of the product of cooling fluid flow rate and temperature rise through the heat exchanger during the course of the batch. Since the oxidation reaction is between zero order and first order for PMIDA (Langmuir-Hinshelwood kinetics), and the first order region is generally below 1000 ppm PMIDA, the residual PMIDA content may also be inferred from the residual rate of reaction at the end of the batch. As the catalyst ages and its activity declines, the effect on first order rate constants can be periodically tracked by sampling near the end of the batch. In operation of a batch process, the rate and extent of catalyst deactivation may be monitored by keeping track of "oxygen practice," as measured by the ratio to glyphosate produced of cumulative quantity of oxygen used to reach the target conversion. This index, which may be expressed in kg oxygen per metric ton of glyphosate (or alternatively in lbs. per hundredweight), increases as the catalyst deactivates for a given PMIDA payload. A similar index may be used for a series of CSTRs, but at higher starting and ending values.

The achievement of a low PMIDA content in the filtered aqueous reaction product stream by increased oxygen flow or extended batch cycle typically involves a modest penalty in glyphosate yield and an increase in the concentration of certain impurities, prominently aminomethylphosphonic acid (AMPA). Where a noble metal on carbon catalyst is used for the reaction, these schemes may also typically result in an increased rate of deactivation of catalyst, resulting in increased catalyst consumption. However, the reduced PMIDA content generally affords a benefit in the preparation of herbicidal glyphosate compositions for the control of weeds in genetically-modified cotton crops that outweighs the adverse effects on yield, catalyst consumption and the minor increase in impurities.

In accordance with the invention, several additional modifications to the oxidation reaction system have been identified that can be used in lieu of, or in combination with increased oxygen flow and/or extended batch cycle as described above.

Alternatively, or in addition to increasing oxygen flow to the reactor(s), enhanced conversion of PMIDA can be achieved by operation at relatively high reaction temperature within the aforesaid range of from about 70° to 140° C., and/or by modification of the catalyst system.

Conversion of PMIDA is promoted by operation at elevated temperature (e.g., in the range of about 110° C. or above) typically from about 110° to about 1.25° C. Because higher temperature leads to increased by-product formation, such as by oxidation of glyphosate to AMPA, the temperature is preferably not increased to more than the extent that may be necessary, either alone or in combination with other modifications such as oxygen flow rate, to achieve the target level of PMIDA. A significant effect on PMIDA conversion can be achieved by operation in the range of from about 115° to about 125° C., or perhaps optimally in the range of from about 118° to about 125° C.

The catalyst system may be modified by an increased charge of noble metal on carbon catalyst, by adding activated carbon to the catalyst system, and/or by altering the selection of promoter for the noble metal on carbon catalyst. If a fresh catalyst charge is increased beyond a threshold level (e.g., above a concentration in the range of from about 1.5% to about 2% by weight) the effect may be to increase the oxidation of PMIDA to IDA rather than glyphosate. However, while PMIDA may oxidize to IDA resulting in an overall selectivity loss, the net effect is still to reduce the PMIDA content of the final glyphosate product. Moreover, when a catalyst mass has been used through a substantial number of recycles, activity of the catalyst mass may usefully be increased by purging some fraction of the spent catalyst and adding fresh catalyst in its place. When this method is followed, PMIDA conversion may be significantly enhanced without significant formation of IDA (i.e., selectivity to glyphosate may be substantially preserved).

An activated carbon catalyst such as the catalyst that is described by Chou in U.S. Pat. No. 4,624,937, is highly effective for oxidation of PMIDA to glyphosate, even if not as effective for oxidation of by-product $C_1$ species such as formaldehyde and formic acid. The carbon catalyst is also relatively inexpensive compared to the noble metal on carbon catalyst, though it is typically consumed at a substantially higher rate. Thus, a fairly liberal addition of carbon catalyst to either a batch reactor, or to the last of a series of cascaded CSTRs, (e.g., in a proportion of at least about 1.5% by weight, typically from about 2.5% to about 3.5% by weight, basis, the noble metal on carbon catalyst charge) can materially reduce the residual PMIDA content in the final reaction solution.

Certain transition metals such as Bi and Te are effective as promoters to improve the effectiveness of a noble metal on carbon catalyst for oxidation of by-product $C_1$ species such as formaldehyde and formic acid. However, data indicate that the oxidation of PMIDA may be marginally retarded by such promoters, perhaps by directing oxygen to contact and react with $C_1$ species in preference to PMIDA. When used either alone or in combination with activated carbon for preparation of low PMIDA content glyphosate, a noble metal on carbon catalyst can either have no promoter, or have a promoter whose identity and loading is selected to minimize any negative effect on the kinetics of the PMIDA oxidation. In this connection, a particular reactor, such as the final reactor in a series of CSTRs, can be dedicated to substantial extinction of PMIDA, and the use of a catalyst which has no promoter, or in which the promoter is selected to be favorable to PMIDA oxidation, can be limited to the dedicated reactor.

Because further thermal effects are minimal once a relatively high conversion has been achieved, a finishing reactor, such as the final reactor in a series of continuous reactors, can readily be operated as a flow reactor (e.g., with a fixed catalyst bed) rather than a back-mixed reactor, so as to enhance the driving force for extinction of PMIDA. Moreover, such finishing reactor can be added, for example, as reactor n+1 after a series of n CSTRs, for example as the fourth reactor following reactor 105 of FIG. 1. Optionally, the catalyst loaded in such reactor can predominantly or exclusively comprise activated carbon.

In order to minimize residual PMIDA in the product reaction solution exiting the final stage of a cascaded continuous stirred tank reaction system, it is helpful to minimize short circuiting of aqueous medium from the reactor inlet to the reactor exit. Thus, in accordance with principles known to the art, the feed point, exit point, baffle array, agitation pattern and agitation intensity may be selected to minimize the extent of short circuiting. Where a CSTR is provided with an external heat exchanger through which the reaction mixture is circulated for removal of the heat of reaction, the reaction mixture may conveniently be withdrawn from the reactor at a forward flow port in the circulating line. Advantageously, the inlet for reaction medium can be positioned in the same circulating line downstream of the exit port by a distance sufficient to avoid any short circuiting due to axial backmixing. For example, the exit port can be placed in the circulating line upstream of the heat exchanger and the inlet port can be located immediately downstream of the heat exchanger.

In accordance with the invention, further process modifications outside the principal PMIDA oxidation system, may be used to reduce the PMIDA content of the finished glyphosate product(s). Such additional modifications, as described hereinbelow, may be used together with or lieu of any combination of the modifications to the reaction system that are described above.

PMIDA Purge

For example, in the process of FIG. 1, the volume of purge stream fraction 133 can be increased relative to evaporative crystallizer mother liquor recycle fraction 135, thus reducing the steady state inventory of PMIDA in the glyphosate product recovery area of the process. The extent of purge required to obtain a given specification for a given form of glyphosate product varies depending on the PMIDA content of the filtered reaction product stream and the exact material balance of the overall process, and especially the material balance of the glyphosate recovery area. The effect of increased purge may be augmented by a more extended wash of the separated glyphosate solids that are obtained as a centrifuge wet-cake in centrifuges 121 and 125, or in filters or centrifuges that may be used in alternative schemes for product recovery. Increased wash volume is ordinarily integrated with the purging scheme because either the wash liquor itself must be purged; or, if the wash liquor is combined with one or more of the recycle mother liquor streams, it marginally increases the amount of PMIDA that must be purged from the process. In either case, the net purge volume is generally increased by an increment corresponding to the volume of the wash liquor. An increase of wash volume might be achieved independently of the purge fraction where the quality of the wash solution permits its use in preparing the aqueous solution of PMIDA which is introduced into the reaction system.

Allocation of PMIDA Among Plural Grades of Glyphosate

The processes as illustrated in FIGS. 1 and 2 are also adapted for the production of different grades of glyphosate, e.g., one grade that has a PMIDA content less than 600 ppm for use in glyphosate compositions for application to genetically-modified cotton crops to inhibit PMIDA-induced necrosis, and another grade of higher PMIDA content that is quite satisfactory for multiple other applications. Generally, the centrifuge wet-cake produced in centrifuge 125 has a lower PMIDA content than the wet-cake produced in centrifuge 121 (or 137) because the mother liquor from the vacuum crystallizer is less concentrated than the mother liquor from the evaporative crystallizer, and because no recycle mother liquor stream is introduced into vacuum crystallizer 109. The PMIDA content of the solid glyphosate acid product removed from the process by centrifuge 121 can be balanced with the PMIDA content of the salt concentrate exiting the process from neutralization tank 127 by increasing the fraction of vacuum crystallizer slurry underflow 117 from the decantation step that is directed to evaporative crystallizer centrifuges 121 relative to that which is directed to centrifuge 125 and/or by increasing the fraction of evaporative crystallizer slurry that is directed to centrifuge 137 for production of evaporative crystallizer centrifuge wet-cake to be incorporated into the concentrated glyphosate salt solution in salt makeup tank 127. If desired, the PMIDA content can be unbalanced, and a disproportionately low PMIDA content salt concentrate prepared by minimizing the fraction of vacuum crystallizer slurry 117 directed to centrifuge 121, and transferring mother liquor from the evaporative crystallizer circuit to the neutralization tank via mother liquor transfer line 139 and/or by eliminating the fraction of evaporative crystallizer slurry that is directed to centrifuge 137.

Alternatively, a low PMIDA content solid glyphosate acid product can be prepared by diverting PMIDA to the salt makeup tank 127. In this case, a relatively high fraction of the vacuum crystallizer slurry underflowing the decantation step is directed to centrifuge 121, and a high fraction of the evaporative crystallizer slurry is sent to centrifuge 137. According to these various process schemes, the process material balance can be managed to contemporaneously, or indeed simultaneously, to produce two separate glyphosate products of distinctly different glyphosate basis PMIDA content.

As a further alternative to the preparation of low PMIDA content glyphosate product, the product obtained during process startup can be segregated and dedicated for use in glyphosate composition for application to and weed control in genetically-modified cotton crops. By starting up with water in the evaporators, neutralization tank and process storage vessels (not shown), the impact of PMIDA in recycle mother liquor can be avoided immediately after startup, and kept to a modest level during the early portion of the transient period in which the product recovery area gravitates to steady state operation.

Further alternative process schemes for allocating residual PMIDA among two or more glyphosate products are described by Haupfear et al. in U.S. Application Publication No. U.S. 2005/0059840 A1, the entire text of which is expressly incorporated herein by reference.

Whether by sequential operation, segregated operations, or control of process material balance to simultaneously yield different grade products, the processes of the invention can be implemented to yield a plurality of differing grade products, including a low PMIDA product having a glyphosate basis PMIDA content typically less than about 1000 ppm, preferably less than about 600 ppm, and at least 25% lower than at least one other, or preferably any other, of such plurality. Moreover, using any one or more of the various process stratagems described above (or below), a low PMIDA product may be produced having a glyphosate basis PMIDA content that is less than about 1000 ppm, or less than about 600 ppm, and at least about 50% lower, or even at least about 75% lower, than the PMIDA content of another of the plurality of products, or preferably any such plurality.

Ion Exchange

In a further alternative embodiment of the invention, PMIDA may be removed from one or more process streams by ion exchange. A variety of options may be followed in providing for removal of PMIDA by ion exchange. For example, an ion exchange column could be used to remove PMIDA from mother liquor as it is recycled from the evaporative crystallizer centrifuge 121 (and/or 137) before separation of purge fraction 133, or in recycle mother liquor fraction 135 after separation of the purge fraction, or in stream 129 from centrifuge 125. Alternatively, or additionally, an ion exchanger could be positioned in the filtered reaction solution stream ahead of the point where it is divided between the vacuum crystallizer 109 and the evaporative crystallizer 111 in FIG. 1.

In an ion exchanger, the PMIDA-bearing process stream is contacted with an anion exchange resin, preferably an anion exchange resin that has a greater affinity for the more strongly acidic PMIDA anion than for the relatively more weakly acidic glyphosate anion and for many of the other compounds in this stream. Because the process stream from which PMIDA is to be removed typically has a high ratio of glyphosate to PMIDA, the resin's affinity for PMIDA should be significantly greater than its affinity for glyphosate. Efficient separation of PMIDA is enhanced where the affinity of the resin for PMIDA is at least two times, three times, four times, five times, 10 times, 20 times or as much as 100 times its affinity for glyphosate. Weakly basic exchange resins are preferred. Functional sites of conventional weak base anion exchange resins typically comprise secondary amine or tertiary amines. Available anion exchange resins typically comprise, for example, a styrene butadiene polymer having a secondary or tertiary amine site which may be protonated in acidic solution to function as an anion exchanger. Suitable commercially available resins include, for example: AMBERLYST A21, AMBERLITE IRA-35, AMBERLITE IRA-67, AMBERLITE IRA-94 (all from Rohm & Haas, Philadelphia, Pa.), DOWEX 50 x 8-400 (Dow Chemical Company, Midland, Mich.), LEWATIT MP-62, IONAC™ 305, IONACM 365 and IONAC™ 380 (Sybron Chemicals, Birmingham, N.J.), and DUOLITE a-392 (Diamond Shamrock Corp., Dallas, Tex.).

A complication in removal of PMIDA by ion exchange can arise from the presence of a substantial fraction of chlorides in the filtered reaction solution, which tend to be concentrated somewhat in the solution ultimately subjected to ion exchange such as evaporative crystallizer mother liquor 131. When an acidic solution such as mother liquor recycle solution 131 is passed over an anion exchange resin, chloride ions are retained at the protonated amine sites preferentially to PMIDA. Where this is the case, two columns may typically be provided in series, with the first column dedicated to removal of chloride ions, with either a strong or weak base anion exchange resin, and the effluent from the first column passed through a second column comprising a weak base exchange resin wherein PMIDA anions are removed. Each column may be eluted and the anion exchange resin regenerated by passage of a caustic solution, typically sodium hydroxide (NaOH), through the column.

The solution from which PMIDA and/or chlorides are to be removed is passed through the column in which the desired exchange occurs until breakthrough of the ion to be removed is observed in the effluent from the column. Breakthrough may occur when the entire column has reached an equilibrium level of chloride ion or PMIDA as the case may be. As saturation is approached, the capacity of the column for the target anion may be reduced to some extent by the presence of the anions of components that are of comparable acidity as the target anion, e.g., phosphate and N-formylglyphosate (NFG). Breakthrough may be determined by any conventional means of detection, including, for example, conductivity, absorbance of light (254 nm), pH and the like. In a preferred method, PMIDA breakthrough is detected by monitoring conductivity of the column eluate. For example, as described in U.S. provisional application Ser. No. 60/667,783, a potential may be applied between a working electrode and another electrode immersed in the column eluate or a sample thereof, and measurement made of a function of the power consumed in maintaining a select current density, or a select potential difference between the electrodes. Alternatively, the end point of an ion exchange cycle can be practiced by volumetric control of the quantity of aqueous solution passed through the column (i.e., the cumulative quantity of mother liquor or other PMIDA-containing stream passed through the anion exchange bed relative to the volume of the bed, typically expressed in "bed volumes.").

After an ion exchange cycle is complete, the column can be eluted to remove the anion that has been collected therein.

A column in which chlorides have been collected from a process stream may be eluted with a caustic solution (e.g., NaOH) to regenerate free amine sites and produce an eluate salt solution that may typically be discarded. Interstitial caustic is removed by washing the column with water. Unless interstitial caustic is removed, it is recycled to the crystallizer with adverse impact on the crystallization.

A column in which PMIDA has been collected from a process stream may first be washed with water to displace process liquid from the column. Thereafter, the column may be eluted with a strong acid to remove PMIDA for recovery; and then regenerated, typically with a caustic solution such as NaOH, and then washed with water to remove interstitial caustic. Eluate comprising PMIDA can be recycled to the oxidation reaction system for further conversion of the PMIDA to glyphosate. Illustrative examples of acids that can be used for elution of PMIDA from an ion exchange column include strong mineral acids such as hydrochloric acid or sulfuric acid. In various embodiments, the ion exchange resin may be contacted with a wash solution or multiple wash solutions during a series of wash steps subsequent to elution. Suitable wash solutions include, for example, water, a buffer solution, a strong base such as KOH, NaOH, or $NH_4OH$ or a weaker base such as $Na_2CO_3$.

During elution of an ion exchange column loaded with PMIDA, the column effluent is monitored for the conjugate base of the strong acid (e.g., chloride ion when Cl is detected in the effluent). Upon appearance of chlorides, recycle of eluate to the PMIDA oxidation step is terminated, and the column is washed with water, then caustic and then again water to return it to the free amine state. If desired, buffers and/or solvents may be used in washing of the column after elution, but this is not ordinarily necessary or useful.

Ion exchange can be conducted at ambient or elevated temperature. More particularly, the mother liquor from the evaporative crystallizer centrifuge 121 (and/or 137) may be treated by ion exchange resin without heating or cooling prior to introduction into the ion exchange column. Typically, this stream has a temperature in the range of from about 45° to about 85° C., more typically from about 55° to about 75° C. Column dimensions and flow rates through the column are governed by standard column design principles and can be readily determined by one skilled in the art.

If desired, a third column can be provided downstream of the PMIDA column for recovery of glyphosate by ion exchange. See, for example, the process as described in U.S. Pat. No. 5,087,740, which is expressly incorporated by reference herein.

In various embodiments, a still further ion exchange column may be provided for recovery of platinum or other noble metal that may have been leached from the catalyst used in the oxidation of PMIDA. Such a process for recovery of noble metal by ion exchange is described in copending and co-assigned U.S. application Ser. No. 11/273,410, filed Nov. 14, 2005, entitled RECOVERY OF NOBLE METALS FROM AQUEOUS PROCESS STREAMS, which is also expressly incorporated herein by reference. Preferably, ion exchange for recovery of noble metal is conducted upstream of the ion exchanger used for separation of PMIDA or removal of chlorides.

In a continuous process such as that illustrated in FIG. 1, a pair of ion exchange columns can be provided in parallel for each ion exchange operation that is conducted as part of the process. In this manner, one column can be used for removal of target anion while the other is being eluted and regenerated.

Although ion exchange has been described above with reference to ion exchange columns, the resin may alternatively be added directly with agitation as a solid phase reagent to the process stream from which the PMIDA (or other target anion) is to be removed. Ion exchange operations have been described above with reference to the continuous processes depicted in FIGS. 1 and 2. Removal of excess PMIDA by ion exchange is also useful in a simplified glyphosate product recovery scheme in which all product reaction solution is directed to a single glyphosate recovery stage such as a single evaporative crystallizer. A single crystallizer typically may be used where the oxidation reaction is conducted in a batch mode. In such a process, glyphosate crystals are separated from the crystallization slurry by filtration or centrifugation, and the mother liquor typically recycled to the crystallizer. In extended operations, a fraction of mother liquor is purged to remove impurities. Ion exchange for removal of PMIDA from the mother liquor allows reduction of the purge fraction necessary to provide a given PMIDA specification in the glyphosate product. Also, the PMIDA which is removed can be recovered by elution as described above and recycled to the oxidation reactor.

FIG. 3 illustrates an exemplary ion exchange system, located, for example, in stream 131 of FIG. 1 or 2, upstream of the purge 133. As illustrated, the system comprises three columns in series, a platinum (or other noble metal) recovery column 201, a chloride removal column 203 and a PMIDA removal column 205. Column 201 comprises an adsorption zone which may comprise activated carbon, or more typically a weak base anion exchange resin, strong base anion exchange resin, strong acid cation exchange resin weak acid cation exchange resin, chelating resin, or in some instances, mixtures thereof. Specific resins useful in the recovery of solubilized platinum are described in U.S. Ser. No. 11/273,410, expressly incorporated herein by reference. Preferably, a chelating resin is used. Column 203 comprises an anion exchange zone containing a resin of the type described hereinabove for removal of chlorides, and column 205 comprises an anion exchange zone containing a resin of the type described for the removal of PMIDA.

Although only a single column is depicted for each recovery or removal operation in FIG. 3, typically at least a pair of columns is provided in parallel at each stage to allow one column to be eluted, regenerated, and washed while the other is in operation for removal of Pt, Cl⁻ or PMIDA, respectively. Operating conditions for column 201 are described in U.S. Ser. No. 11/273,410. As further described in the '410 application, breakthrough of noble metal from column 201 may be detected by ICP-MS, ICP-OES, or AA. A simple conductivity device is effective for determining breakthrough of chlorides from column 203 or 205.

While FIG. 3 depicts separate columns (or column pairs) in series for chloride removal and PMIDA removal, respectively, the two columns function as a single adsorption system so far as adsorption phenomena are concerned, at least in the case where the ion exchange properties of the resins used in columns 203 and 205 are substantially the same. In any case, all adsorbable components of the solution are initially adsorbed on column 203 but PMIDA is progressively displaced by Cl⁻ as the column becomes loaded. PMIDA desorbed from or passing through column 203 is adsorbed on the anion exchange resin in column 205. When column 203 (or a corresponding adsorption zone within a single column) becomes loaded with chloride, the latter ions eventually break through in the effluent from column 203 (or corresponding zone) and begin displacing the PMIDA from column 205 (or a corresponding downstream adsorption zone of a single column). Separating the adsorption bed into two columns facilitates monitoring the chloride wave and scheduling regeneration of anion exchange resin for sustained operations. Breakthrough from column 205 may result from either saturation of the resin therein with PMIDA or displacement of PMIDA by chloride. In either case, breakthrough may occur before maximum PMIDA loading is realized, with the PMIDA content of the effluent progressively increasing as column saturation is approached, rising to the level in the inlet mother liquor stream when saturation is reached. Where chloride displaces PMIDA, the PMIDA loading reaches a maximum and then begins to decline as it is displaced by chloride. In the system depicted in FIG. 3, this conditions can be avoided if column 203 is regenerated as soon as chloride breakthrough is observed. In either case, process operators can identify an optimum balance between PMIDA removal efficiency and column loading.

Regardless of whether the chloride and PMIDA ions are removed in physically separate adsorption beds in series or in a single adsorption bed, the adsorption system may be considered to comprise two distinct adsorption zones, one in which chlorides are being adsorbed and another in which PMIDA is being adsorbed. However, the size and location of these adsorption zones are not static. The boundary between the zones moves as the chloride wave advances in displacing PMIDA from the resin.

Shown at 207 is a device effective to sense breakthrough of PMIDA from column 205. The device comprises a pair of electrodes immersed in the stream exiting the column or a sample thereof, and is controlled to maintain a select current density or impose a select voltage or schedule of voltages between the electrodes. Where the device is controlled to maintain a select current density, breakthrough of PMIDA is reflected in a drop, typically a relatively sharp drop in the voltage required to maintain the select current density. Where a select voltage, or programmed series of voltages is imposed, breakthrough of PMIDA is indicated by a significant increase in current at a voltage that is sufficient for electrolytic oxidation of $C_1$s and PMIDA but not residual glyphosate. Detailed descriptions of devices which function on these bases are set forth in co-assigned U.S. provisional application Ser. No. 60/667,783, which is expressly incorporated herein by reference.

Whenever any of columns 201, 203 or 205 reaches a breakthrough condition, introduction of mother liquor is terminated and the adsorbed component recovered. In the case of column 205, PMIDA may be eluted with a strong acid such as HCl. Both columns 203 and 205 may be regenerated using a caustic eluant, followed by a water wash, as described above. The aqueous NaCl eluate may be discarded. In the case of column 201, the noble metal component may optionally be eluted with an eluant, e.g., an acidic eluant where the noble metal species is present in the form of cation, or a caustic eluant where the noble metal is present in an anion. However, in the case of column 201, more quantitative recovery can generally be achieved by removing the loaded resin from the column, incinerating the resin, and recovering noble metal from the ash.

Recovery of noble metal in column 201 is typically in the range between about 60% and about 85%. Thus, in monitoring operation of this column "breakthrough" is a relative term, and the breakthrough detection device is calibrated to detect an increase in signal above a steady state level. In any event, a portion of the noble metal is typically lost in purge stream 133 or in the product glyphosate salt concentrate. Where PMIDA is removed by ion exchange via column 205, it has been found that a portion of the noble metal passing through columns 201 and 203 is adsorbed on the resin contained in column 205. If this column is regenerated or washed with aqueous ammonia, the platinum is desorbed, and ultimately lost either in the purge stream or by incorporation into the aqueous glyphosate salt product. However, it has been discovered that if the column is regenerated with a strong base such as an alkali metal hydroxide, e.g., NaOH or KOH, and washed with strong base or water, platinum species are typically not desorbed, but remain on the column, thus allowing ultimate recovery of this fraction of the platinum by removal and incineration of the resin.

Disposition of the eluates from columns 203 and 205, respectively, is as described above. The acidic eluate comprising PMIDA is typically recycled to the reaction system. As regeneration proceeds, the chloride content typically declines in the caustic regeneration solution exiting the column. Advantageously, a portion of the caustic regeneration solution, particularly that exiting the column toward the end of the regeneration cycle, may be preserved and used in a subsequent regeneration cycle in the same or a parallel PMIDA removal column.

Although an anion exchange resin which has a substantially higher affinity for PMIDA than for glyphosate is preferably selected for column 205, some glyphosate is typically removed along with PMIDA from the mother liquor or other solution that is processed in the column. The incidence of glyphosate removal may be relatively significant when the column contains fresh or freshly regenerated resin. As PMIDA accumulates in the column, the glyphosate fraction moves down (or in any event toward the column exit) in a manner similar to the operation of a chromatographic column. In an alternative embodiment of the process, the effluent from column 205 may be monitored not only for PMIDA but also for glyphosate. As the column becomes loaded with PMIDA, glyphosate breaks through first. When the column is eluted, a glyphosate fraction comes off first and may be segregated for recycle, e.g., to the evaporative crystallizer. Prior to elution, the column is washed for removal of residual glyphosate caught in the interstitial spaces between the resin beads. The glyphosate content of the wash solution may also be sufficient to justify recycle to the evaporative crystallizer.

Where the operation of column 205 is monitored by use of device 207, the threshold voltage at which a significant current density is realized may first be observed to decline to a value reflective of the oxidation of glyphosate. Such threshold voltage substantially prevails until PMIDA breakthrough approaches. During elution, a similar voltage response or requirement should be observed during elution of the glyphosate fraction which may be directed, e.g., to a feed tank for the evaporative crystallizer. When the voltage required to sustain a target current density declines to a value reflective of the oxidation of PMIDA, the eluate may be redirected for recycle to the reactor, or alternatively to the purge.

According to a further alternative for recovery of glyphosate, a column loaded with both glyphosate and PMIDA may be initially eluted with a relatively weak base such as isopropylamine ("IPA") to remove the relatively weakly sorbed glyphosate in the form of the salt. Optionally and preferably, neat liquid IPA can be used for the elution, which produces an eluate consisting of a relatively concentrated solution of the IPA salt of glyphosate. This eluate may directed to neutralization and mixing tank 127 and used directly in producing aqueous IPA glyphosate concentrates.

In accordance with a further process alternative, as mentioned above, another column comprising an ion exchange zone comprising a resin effective for sorption of glyphosate, typically a further ion exchange column, can be provided downstream of column 205. This column is not shown in FIG. 3 but may be positioned to receive the process stream that has been passed in series through columns 203 and 205, or in series through columns 201, 203 and 205.

Finishing Reactor in Product Recovery Process

According to a further alternative, PMIDA can be removed from product recovery process streams by catalytic oxidation to glyphosate. In addition to or in lieu of a finishing reactor as described above in the principal reaction train, polishing reactor(s) can be positioned in one or more process streams within a product recovery system of the type illustrated in FIG. 1. For example such a reactor could be positioned in the feed stream to evaporative crystallizer 111 (as a pre-recovery polishing reactor), in mother liquor stream 131 exiting evaporative crystallizer centrifuge 121 (and/or 137), or elsewhere in the process.

Such further finishing reactor can optionally be operated with only a carbon catalyst. Moreover, since only marginal oxidation is involved, thermal effects are minimal, making it at least potentially advantageous to operate the reactor as a flow reactor with a fixed bed of catalyst, thus enhancing the driving force for substantial extinction of PMIDA. Where the reactor is placed in stream 131, ahead of the purge stream, the effect on overall yield of the marginal oxidation of glyphosate to AMPA is minimal. Oxidation reaction systems for preparation of glyphosate reaction solutions by catalytic oxidation of a PMIDA substrate including finishing or pre-recovery polishing reactors are described by Haupfear et al. in U.S. Application Publication No. U.S. 2002/0068836 A1, the entire contents of which is incorporated herein by reference.

Crystallizer Operations

Process options effective to produce a product of relatively low PMIDA content have implications for the operation of evaporative crystallizer 111. PMIDA has been found to function as a solubilizer for glyphosate. Thus, where the reaction system is operated under such conditions as to yield a filtered product reaction solution of relatively low PMIDA content, and/or where the filtered reaction solution is passed through a finishing reactor for further conversion of PMIDA to glyphosate, and/or where PMIDA is removed from recycle mother liquor by ion exchange, solubility of glyphosate in the recycle mother liquor can be lowered. At a given system pressure, a lower PMIDA/glyphosate ratio causes crystallization to commence at relatively lower temperature, which can result in fouling of process side heat exchanger surfaces in or associated with the evaporative crystallizer.

Figure 4:
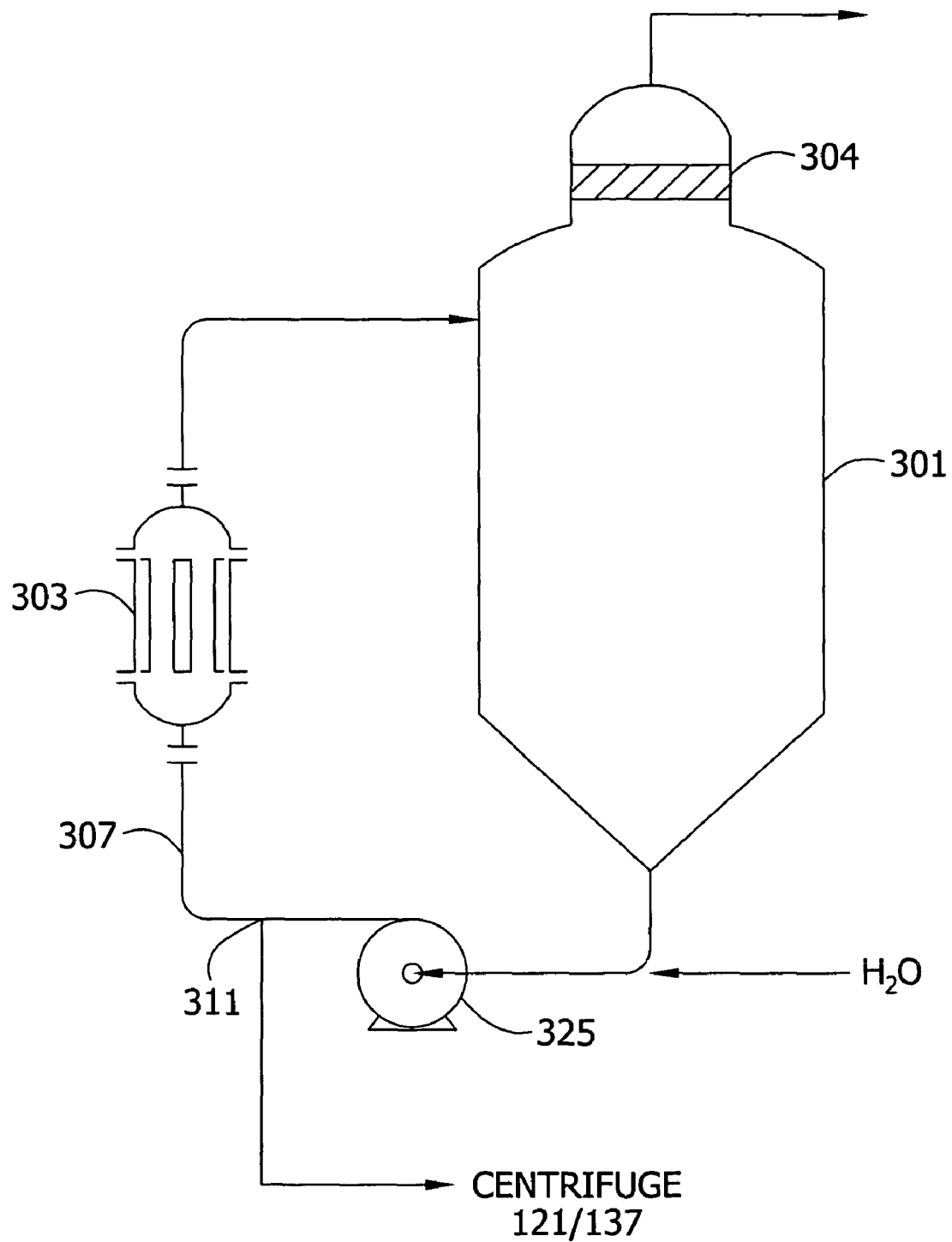
FIG. 4 is a schematic flow sheet illustrating an evaporative crystallization system modified to accommodate low N-(phosphonomethyl)iminodiacetic acid (PMIDA) content in the feed solution without excessive fouling of the heat exchange surfaces and which may be used in conjunction with the process for the manufacture of glyphosate illustrated in FIG. 1 or 2.

FIG. 4 illustrates an evaporative crystallization system modified to accommodate low PMIDA content in the feed solution without excessive fouling of the heat exchange surfaces. In the system of FIG. 4, crystallizer 109 comprises a vapor liquid separator 301, an external heat exchanger 303, and an axial or centrifugal circulation pump 305 and line 307 for circulation of the crystallization slurry between the vapor liquid separator through the heat exchanger. A mist eliminator 309 in the upper portion of the vapor liquid separator helps to collect entrained liquid and return it to the liquid phase within the separator body. Crystallization slurry is drawn off through port 311 in the circulation line for delivery to centrifuge 121 and optionally centrifuge 137. Fouling of heat exchanger 303 is potentially attributable to accumulation of glyphosate on the process side tube surfaces, but may also be attributable to plugging of the heat exchanger tubes with large chunks of crystalline material which may calve off the walls of separator 301.

It may further be noted that the commencement of crystallization at lower temperature results in an enhanced crystallization yield. While this effect may be advantageous from the standpoint of initial crystallizer productivity, and marginally beneficial with regard to yield on raw materials, the higher solids content of the circulating slurry is believed to have an adverse effect on heat transfer. Increased solids content increases the effective viscosity of the circulating slurry, thereby increasing pressure drop through the heat exchanger. At a given limiting pump head, this results in a decreased flow rate, decreased velocity along the process side of the tube wall, and consequently decreased heat transfer coefficients. Thus, even without any fouling or plugging of tubes, heat transfer rates and productivity can be compromised by the higher solids content obtained as the crystallization temperature drops with PMIDA content.

In any event, injection of water into the circulating pump suction imposes a sensible heat load that tends to reduce the rate of precipitation in the tubes. Although water injection does not reduce the steady state composition of the liquid phase in the vapor/liquid separator, it marginally reduces the degree of supersaturation in the liquid phase entering the heat exchanger, and may thus marginally reduce the tendency of the tubes to foul by further encrustation with glyphosate.

Perhaps more significantly, it reduces the solids content of the slurry passing through the heat exchanger, thus reducing the viscosity, and contributing to increased process side velocity and heat transfer coefficients.

Injection of water above the mist eliminator is useful in minimizing pressure drop through the mist eliminator and controlling the extent of crystallization on the walls of the separator. Increasing the slurry circulation rate via pump 303 serves to reduce the temperature rise in the heat exchanger and enhance the scouring action of the circulating slurry, further contributing to control of fouling.

Aside from the complications which it can create in the operation of the evaporative crystallizer, ion exchange also functions to reduce the chloride and phosphate content of the mother liquor circulating in the evaporative crystallization system. Whether as a result of lower chloride and phosphate content or otherwise, it has been found that enhanced crystal growth is achieved in the evaporative crystallizer in operations wherein PMIDA, and necessarily also chloride and phosphate, is removed by ion exchange. The larger crystals thus produced have superior dewatering properties as compared to the crystals obtained in an evaporative crystallization system wherein a mother liquor of relatively high PMIDA, Cl⁻, and/or phosphate concentration circulates between the evaporative crystallizer and centrifuge 121 or 121 and 137. Production of relatively larger crystals is advantageous in removal of residual impurities, including PMIDA, by separation of solids from mother liquor in the centrifuge(s) and washing of the centrifuge cake. It has further been observed that, where the crystallizer is operated to consistently generate relatively large glyphosate particles, the fouling effect of reduced PMIDA content is at least partially offset. Heat exchange surfaces are generally less prone to fouling in an operation wherein heat is transferred to a slurry comprising relatively large particles than in an operation where relatively fine crystals are produced.

Programmed Control Scheme

The present invention contemplates the use of essentially all combinations and permutations of the various measures that are described hereinabove for reducing the PMIDA content of a glyphosate product. In some instances, it may not be technically feasible or economically attractive to achieve a target PMIDA concentration by resort solely to increased oxygen flow rate, solely to increased purge, or solely to another single process stratagem outlined herein. Although certain process modifications such as ion exchange, where justified, may be quite sufficient to achieve any desired PMIDA level, there can still be advantages in adopting ion exchange in combination with other operational variations.

In practicing the various methods of the invention, operational stability, economic optimization, product and emission specification and/or other advantages and constraints may be met or achieved by a programmed control scheme under which a combination of various measures such as increased oxygen flow, purge adjustment, allocation of PMIDA among plural product forms, ion exchange conditions, process flows, reactor and crystallizer temperatures, reactor and crystallizer pressures, etc., may be monitored and controlled at values which achieve a target PMIDA specification in one or more glyphosate product forms according to an optimal or otherwise desirable operational mode. In accordance with such a control scheme, signals conveying the current values of various parameters and the control set points for the control loops for such parameters may be transmitted to a programmed controller which, in response to these inputs, may generate out put signals to adjust the various set points according to an algorithm inscribed in controller software. For example, the algorithm may be adapted to achieve a target PMIDA content in a specified glyphosate product form at minimum cost, and/or at maximum throughput, and/or to meet other product specifications, and/or to conform to emission standards, etc.

Such a program may be periodically adjusted as necessary to reflect changes in raw material prices, product demand, production scheduling, environmental conditions, etc.

Glyphosate Product

By implementation of one or more of the process modifications and stratagems as described above, a manufactured glyphosate product may be recovered and removed from the process in a desired form with a PMIDA content of less than, 6,000 ppm, 5,000 ppm, 4,000 ppm, 3,000 ppm, 2,000 ppm, 1,000 ppm, 600 ppm or even significantly lower. A glyphosate product of such low PMIDA level can be produced, for example, in the form of a solid crystalline glyphosate acid, or in the form of an aqueous concentrate of glyphosate salt, such as a potassium or isopropylamine salt having a glyphosate content of at least about 360 gpl, a.e., preferably at least about 500 gpl, a.e., more preferably at least about 600 gpl, a.e.

Glyphosate having a relatively low PMIDA content, e.g., not greater than about 0.45 wt. % acid equivalent on a glyphosate, a.e., basis, can be prepared by any of a variety of manufacturing processes. Significant commercial advantages result from the preparation of glyphosate by a process comprising the catalytic oxidation of a PMIDA substrate as described in detail hereinabove. Glyphosate obtained in this manner has a very low glyphosine content, typically less than about 0.010 wt. % acid equivalent on a glyphosate a.e. basis. It generally has a small but acceptable glycine content, i.e., at least about 0.02 wt. % acid equivalent as also computed on a glyphosate, a.e., basis. PMIDA-derived glyphosate product may also include small, but acceptable concentrations of a number of other by-products and impurities. These may include for example: iminodiacetic acid or salt thereof (IDA) in a concentration of at least about 0.02 wt. % acid equivalent on a glyphosate, a.e., basis; N-methyl glyphosate or a salt thereof (NMG) in a concentration of at least about 0.01 wt. % on a glyphosate, a.e., basis; N-formyl glyphosate or a salt thereof (NFG) in a concentration of at least about 0.010 wt. % acid equivalent on a glyphosate, a.e., basis; iminobis(methylenephosphonic acid) or a salt thereof(iminobis) in a concentration of at least about 0.010 wt. % acid equivalent on a glyphosate, a.e., basis; and N-methylaminomethylphosphonic acid (MAMPA) or a salt thereof in a concentration of at least about 0.010 wt. % acid equivalent on a glyphosate, a.e., basis.

These relative proportions generally apply regardless of the form of the glyphosate product, i.e., regardless of whether it is in the form of solid state glyphosate acid or a concentrated aqueous liquid solution comprising a glyphosate salt such as, for example, a potassium, isopropylamine, monoammonium or diammonium salt. Preferred aqueous concentrates comprise at least about 360 grams per liter glyphosate on an acid equivalent basis, with proportionate minor concentrations of the common by-products and impurities as listed above.

Further detailed limits and ranges for IDA, NMG, AMPA, NFG, iminobis, and MAMPA are set out below. All are expressed on an acid equivalent basis relative to glyphosate, a.e.

More typically, the IDA content may be between about 0.02 wt. % and about 1.5 wt. %, e.g., between about 0.05 wt. % and about 1.0 wt. %, on a glyphosate a.e. basis. Preferably, the IDA content is not greater than about 0.58 wt. %, not greater than about 0.55 wt. %, or not greater than about 0.50 wt. % on the same basis. In most operations, the product obtained has an IDA content between about 0.1 and about 0.58 wt. %, between about 0.1 and about 0.55 wt. %, between about 0.02 and about 0.55 wt. %, or between about 0.1 and about 0.50 wt. %.

Generally, the NMG content is between about 0.02 and about 1.5 wt. %, for example, between about 0.02 and about 1.0 wt. %, or between about 0.070 and about 1 wt. % on a glyphosate, a.e., basis. Preferably, the NMG content is not greater than about 0.55 wt. % or not greater than about 0.50 wt. %.

The glyphosate product also typically contains aminomethylphosphonic acid or a salt thereof (AMPA) in a concentration that may be incrementally higher than that of glyphosate products which have relatively higher residual PMIDA content. For example, the AMPA content may range between about 0.15 and about 2 wt. %, more typically between about 0.2 and about 1.5 wt. % aminomethylphosphonic acid or a salt thereof on a glyphosate, a.e., basis. In most instances, the AMPA content is at least about 0.30 wt. % on the same basis.

The NFG content is ordinarily between about 0.01 and about 1.5 wt. %, e.g., between about 0.03 and about 1.0 wt. %, more typically between about 0.010 and about 0.70 wt. % on a glyphosate, a.e., basis. It is generally preferred that the NFG content be not greater than about 0.70 wt. %, not greater than about 0.60 wt. %, not greater than about 0.50 wt. %, not greater than about 0.40 wt. %, or not greater than about 0.30 wt. % on the same basis.

Typically the iminobis content of the glyphosate product is between about 0.1 and about 1.5 wt. %, e.g., between about 0.2 and about 1.0 wt. % on a glyphosate, a.e., basis. Preferably, the iminobis content is not greater than about 0.8 wt. % iminobis(methylenephosphonic acid), normally between about 0.2 and about 0.8 wt. % on the same basis.

The MAMPA content is ordinarily between 0.1 about and about 2 wt. %, e.g., between 0.15 about and about 1.0 wt. % on a glyphosate, a.e., basis. Most typically, the MAMPA content is at least about 0.25 wt. % MAMPA on the same basis. Most PMIDA-derived product comprises between about 0.25 and about 0.6 wt. % MAMPA.

Although the typical levels of these various impurities and by-products are inconsequential so far as the function, use and handling of the glyphosate product is concerned, they serve as markers which distinguish a product produced by catalytic oxidation of PMIDA from glyphosate product as produced by other processes. The presence of such impurities and by-products in the upper portions of the above described ranges have some measurable impact on manufacturing process yields, and thus on product manufacturing cost.

Other Glyphosate Manufacturing Processes

Glyphosate product of low PMIDA content may also be manufactured by processes that use substrates such as AMPA or glycine. Each of these processes generates a profile of by-products and impurities that is somewhat different from that of the PMIDA oxidation process. For example, the product of the glycine process most typically contains glyphosine in a concentration greater than about 0.010 wt. %, more typically at least about 0.1 wt. %, and most typically in the range of about 0.3 to about 1 wt. %, all on a glyphosate, a.e., basis. The product of the AMPA-based process may have a modest to significant fraction of unreacted AMPA, though the product of the PMIDA process can have a comparable AMPA content, especially when latter is operated to minimize residual PMIDA and the former to minimize residual AMPA. The glycine content of the AMPA process product is generally significantly lower than 0.02 wt. % on a glyphosate, a.e., basis.

According to an alternative embodiment of the present invention, glyphosate of low PMIDA content may be produced from glycine, e.g., by a process as described in U.S. Pat. No. 4,486,359, which is expressly incorporated in its entirety herein by reference. In this process, glycine is initially reacted with paraformaldehyde in the presence of triethylamine to produce N,N-bis(hydroxymethyl)glycine. The reaction is conducted in a methanol medium, typically at MeOH reflux temperature (i.e., about 65° C.). The N,N-bis(hydroxymethyl)glycine intermediate is reacted with dimethyl phosphite to yield an ester, which the above-mentioned patent characterizes as the methyl ester of glyphosate. The ester is hydrolyzed in HCl to glyphosate acid. This product generally has a glyphosine content in excess of 0.010 wt. %, more typically between about 0.05% and about 2% on a glyphosate, a.e., basis. Commercial sources of glycine process glyphosate may commonly contain between about 0.2% and about 1.5% by weight glyphosine and between about 0.05% and about 0.5% by weight glycine, more typically between about 0.3 and about 1% by weight glyphosine and between about 0.1 and about 0.3% by weight glycine, all on a glyphosate, a.e., basis.

In an alternative to the process of U.S. Pat. No. 4,486,359, Japanese Published Application Hei 9-227583 (application no. Hei-9-6881) describes a process in which the reaction between paraformaldehyde and glycine may be conducted in the presence of tributylamine rather than triethylamine, and the ester intermediate may be hydrolyzed in an alkaline medium such as NaOH rather than in acidic medium such as HCl. The Japanese patent publication reports that the base hydrolysis may produce a product of lower glyphosine content than the product of the process of U.S. Pat. No. 4,486,359.

In conducting the process, a source of formaldehyde, preferably paraformaldehyde is mixed with a reaction medium comprising $C_1$ to $C_4$ alcohol at moderately elevated temperature, tributylamine is added to the resulting solution and the mixture preferably agitated at about 35° to 50° C. for typically 30 to 60 minutes. Glycine is added to the alcohol medium in a proportion which preferably assures a formaldehyde to glycine molar ratio from about 1 to 5, and the glycine is preferably completely dissolved in the medium. Preferably, the molar ratio of tributylamine to glycine is from about 0.5 to about 3. The temperature is maintained at least about 30° C., preferably between about 50° and about 60° C. for typically about 10 to 60 minutes, resulting in reaction of glycine with formaldehyde to form the tributylamine salt of N-methylolglycine. A dialkylphosphite, e.g., dimethylphosphite, is then added to the solution under agitation at elevated temperature, preferably at least about 50° C., more typically about 65° to about 80° C., conveniently under alcohol reflux, preferably at a molar ratio to N-methylolglycine from about 0.6 to about 2.0. Dialkylphosphite condenses with the tributylamine salt of N-methylolglycine to yield an ester intermediate depicted in the Japanese patent publication as the dialkyl ester of the tributylamine carboxylate salt of glyphosate. Addition of a strong base such as NaOH, to this solution saponifies the ester, liberates tributylamine and forms the Na salt of glyphosate. The reaction mixture separates into two liquid phases, yielding an upper layer containing tributylamine and a lower layer comprising a solution of Na or K salt of glyphosate. Tributylamine may be recovered from the upper layer for recycle. The lower layer may be acidified to crystallize glyphosate acid.

In accordance with the present invention, the alkaline hydrolysis may be conducted with a strong base comprising a desired countercation such as, e.g., KOH, as a step in the preparation of an aqueous concentrate of the potassium salt of glyphosate. Where the phase separation is carried out under conditions that assure substantially quantitative partition of tributylamine to the upper layer, the lower layer may be used directly in the preparation of an aqueous glyphosate concentrate comprising the potassium salt. Alternatively, the glyphosate salt may be acidified to precipitate glyphosate acid, and the glyphosate acid separated by filtration or centrifugation and washed, and the washed glyphosate wet-cake reslurried with water and base to produce the desired salt. In the latter process, the advantage of using KOH for the conversion of intermediate ester to glyphosate salt is diminished. Where triethylamine is used as the alkylamine, it can be quantitatively removed by distillation of the hydrolyzate, which may in certain instances facilitate direct preparation of a concentrate of the glyphosate salt of the base used for the conversion of the intermediate ester. Preferably, the concentrate comprises at least about 360 gpl glyphosate on an acid equivalent basis.

Regardless of whether the aqueous or solid glyphosate concentrate is prepared from glyphosate produced by oxidation of PMIDA or from glyphosate produced from glycine or other starting material, the concentrates of the invention include mixed countercation concentrates comprising any combination of monoammonium, diammonium, isopropylamine, potassium, dipotassium, sodium, monoethanolamine, ethylamine, ethylenediamine, n-propylamine, hexamethylenediamine, or trimethylsulfonium salt. A preferred combination may comprise potassium, or a mixture of potassium and isopropylamine salts, wherein each of potassium and isopropylamine is in a mole ratio to glyphosate between about 0.1 and about 0.9. In such a concentrate, the mole ratio of isopropylamine to potassium may be between about 0.1 and about 0.9, in certain embodiments between about 0.2 and about 0.8, and in certain particular embodiments between about 0.3 and about 0.7. In such mixed countercation concentrates, the mole ratio of the sum of isopropylamine and potassium to glyphosate may typically be between about 0.7 and about 1.2.

As far as is known, glyphosate has not been manufactured on a commercial scale in the United States using tributylamine and/or an alkaline hydrolysis process. However, it is understood that this process may be capable of producing a glyphosate product of the present invention, preferred embodiments of which contain relatively low concentrations of glyphosine. For example, it is understood that the alkaline hydrolysis process may be conducted in a manner effective to yield a glyphosate product containing glyphosine in a proportion between about 0.05 to about 0.8 wt. %, about 0.05 to about 0.6 wt. %, about 0.05 to about 0.5 wt. % or about 0.05 to about 0.4 wt. %, about 0.1 to about 0.8 wt. %, about 0.1 to about 0.6 wt. %, 0.1 to 0.5 wt. %, 0.1 to 0.4 wt. % or about 0.1 to 0.3 wt. %, basis glyphosate a.e. Such product may typically contain glycine in a concentration between about 0.05 and about 4 wt. %, more typically between about 0.05 and about 2 wt. %, or between about 0.1 and about 0.5 wt. %, on a glyphosate, a.e., basis.

As noted above, aqueous liquid concentrates comprising agronomically acceptable salts of glyphosate preferably contain a surfactant that promotes penetration of the herbicide into the foliage of the plant. Cationic surfactants are generally preferred, but nonionic surfactants and combinations of cationic and nonionic surfactants are also advantageous. Particularly preferred cationic surfactants include alkoxylated alkylamines, alkoxylated etheramines, alkoxylated phosphate esters, and combinations thereof. It will be understood that the present invention encompasses each all of the various PMIDA-based, glycine-based and other glyphosate products described or referred to above in combination with such surfactants or combinations of surfactants.

To provide a reliable commercial source of glyphosate having a relatively low residual PMIDA content, it is necessary to either operate the manufacturing process on a sustained basis to consistently produce glyphosate product of low PMIDA content, or to segregate product from designated operations in order to accumulate commercial quantities of low PMIDA product.

Although glyphosate products having a low PMIDA content have been incidentally produced on a transient basis during startup of a manufacturing facility for the catalytic oxidation of PMIDA to glyphosate, or in operation well below rated capacity, the processes of the prior art have not been effective for the preparation of a low PMIDA glyphosate product on a continuing basis during steady state operations at or near capacity. Thus, each of the various glyphosate products of the invention encompasses a lot, run, shipment, segregate, campaign or supply of glyphosate product as produced by a process capable of maintaining a low PMIDA content on a continuing basis. According to the present invention, such a lot, run, shipment, campaign, segregate or supply comprises a quantity of solid state glyphosate acid, or concentrated aqueous solution of glyphosate salt, comprising at least 1500 metric tons, preferably at least about 3000 metric tons, glyphosate on a glyphosate a.e. basis.

For purposes of this invention, a "lot" may be considered a designated quantity of glyphosate product that is produced under substantially consistent process conditions in a particular manufacturing facility during a defined period of operations or over a designated period of time. Production of the lot may be interrupted for production of other glyphosate product or non-glyphosate product, or purge of impurities from the process, but not otherwise by catalyst replacement, turnaround or startup operations. Glyphosate may be produced according to various different processes, some of which (e.g., a process comprising the aqueous phase catalytic oxidation of PMIDA) can be conducted in either a batch or continuous mode in the oxidation step and/or or in the recovery of glyphosate by crystallization thereof from an aqueous medium. With reference to a process comprising a batch reaction and/or batch glyphosate crystallization operation, it is understood that a lot may comprise the product of a plurality of batches.

A "run" is quantity of glyphosate product made in a particular manufacturing facility in continuing or consecutive operations over a designated period without interruption for maintenance, catalyst replacement, or catalyst loading. It may include both startup and steady state operations. With reference to a batch reaction and/or batch glyphosate crystallization operation, it is understood that a run may comprise the product of a plurality of batches.

A "campaign" is a series of runs conducted over an identifiable period of time during which the runs may be interrupted by other runs not part of the campaign or by purge of impurities, or for maintenance, but not by turnaround or catalyst replacement. No more than one of the runs may include startup operations; provided, however, that more than one of the runs may comprise operation at a rate more than 30% below established capacity. Compare the description of startup operations as set out hereinbelow.

A "shipment" is a commercial quantity of glyphosate product transported to a particular customer or user in either a single unit, single combination of units, consecutive units, or consecutive combinations of units without interruption by transport of a commercial quantity of a glyphosate product of materially different average PMIDA content on a glyphosate, a.e., basis to the same user or customer. A materially different PMIDA content is PMIDA content that is either more than 0.15 wt. % higher than the average PMIDA content of the shipment on a glyphosate, a.e., basis, more than 35% higher than the average PMIDA content of the shipment on a PMIDA basis, or is above 4500 ppm on a glyphosate a.e. basis.

A "supply" is a series of shipments that may be interrupted by other shipments of glyphosate product to other customers or users.

A "segregate" is a quantity of glyphosate product that is isolated from other glyphosate product produced in the same manufacturing facility over the same period of time (i.e., the time during which the segregate is produced). The segregate may be produced in different runs, and may be allocated among different shipments or different supplies.

Startup operations are operations that are conducted in a manufacturing facility in which glyphosate product has not previously been produced, or directly following interruption of the production of glyphosate product and removal of a substantial fraction of the inventory of process liquids contained in process equipment, with the effect of lowering the total inventory of by-products and impurities in the process facility by at least 25 wt. %. Impurities and by-products include PMIDA, IDA, AMPA, NMG, NFG, iminobis(methylenephosphonic acid), MAMPA, formic acid, NMIDA, glycine and glyphosine. For purposes of this invention, operations at a rate that is more than 30% below currently established capacity of a manufacturing facility is also deemed within the ambit of startup operations.

OTHER DEFINITIONS

Unless otherwise noted, terms and abbreviations are to be understood according to conventional usage by those of ordinary skill in the relevant art. Definitions of common terms in molecular biology may also be found in Rieger et al., *Glossary of Genetics: Classical and Molecular*, 5th edition, Springer-Verlag: New York, 1991; and Lewin, *Genes V*, Oxford University Press: New York, 1994. The nomenclature for DNA bases as set forth at 37 CFR §1.822 is used.

"Affinity" as used herein means the tendency of an ion exchange resin to complex with another species, such as PMIDA or glyphosate, under the existing process conditions, including the particular combination of acids, solvents, and other ingredients that are present.

When a maximum or minimum "average number" is recited herein with reference to a structural feature such as oxyethylene units or glucoside units, it will be understood by those skilled in the art that the integer number of such units in individual molecules in a surfactant preparation typically varies over a range that can include integer numbers greater than the maximum or smaller than the minimum "average number". The presence in a composition of individual surfactant molecules having an integer number of such units outside the stated range in "average number" does not remove the composition from the scope of the present invention, so long as the "average number" is within the stated range and other requirements are met.

A transgenic "event" is produced by transformation of a plant cell with heterologous DNA, e.g., a nucleic acid construct that includes a transgene of interest; regeneration of a population of plants resulting from the insertion of the transgene into the genome of the plant cell, and selection of a particular plant characterized by insertion into a particular genome location. The term "event" also refers to the original transformant plant and progeny of the transformant that include the heterologous DNA.

"Exogenous" refers to materials originating from outside of an organism or cell. This typically applies to nucleic acid molecules used in producing transformed or transgenic host cells and plants.

"Fruiting branch" refers to a reproductive branch of a cotton plant upon which the fruit (boll) appears and typically arises at the fourth through eighth plant node.

The term "gene" refers to chromosomal DNA, plasmid DNA, cDNA, synthetic DNA, or other DNA that encodes a peptide, polypeptide, protein, or RNA molecule, and regions flanking the coding sequence involved in the regulation of expression.

"Glyphosate-tolerant" refers to a plant exhibiting reduced phytotoxic effects from application of glyphosate (e.g., N-(phosphonomethyl)glycine or a salt thereof) on the plant.

Herbicidal effectiveness is one of the biological effects that can be enhanced through this invention. "Herbicidal effectiveness," as used herein, refers to any observable measure of control of plant growth, which can include one or more of the actions of (1) killing, (2) inhibiting growth, reproduction or proliferation, and (3) removing, destroying, or otherwise diminishing the occurrence and activity of plants. The herbicidal effectiveness data set forth herein report "control" as a percentage following a standard procedure in the art which reflects a visual assessment of plant mortality and growth reduction by comparison with untreated plants, made by technicians specially trained to make and record such observations. In all cases, a single technician makes all assessments of percent control within any one experiment or trial. Such measurements are relied upon and regularly reported by Monsanto Company in the course of its herbicide business.

"Heterologous DNA" refers to DNA from a source different than that of the recipient cell.

"Homologous DNA" refers to DNA from the same source as that of the recipient cell.

"Layby" refers to the growth point at which a final herbicide ground application is made that is designed to eliminate or suppress weeds until harvest.

"Node" refers to a point along the main cotton plant stem from which vegetative and fruiting branches originate.

When used in the context of a surfactant or a glyphosate salt, "predominantly" means at least about 50%, preferably at least about 75% and more preferably at least about 90%.

A "recombinant" nucleic acid is made by an artificial combination of two otherwise separated segments of sequence, e.g., by chemical synthesis or by the manipulation of isolated segments of nucleic acids by genetic engineering techniques.

The term "recombinant DNA construct" or "recombinant vector" refers to any agent such as a plasmid, cosmid, virus, autonomously replicating sequence, phage, or linear or circular single-stranded or double-stranded DNA or RNA nucleotide sequence, derived from any source, capable of genomic integration or autonomous replication, comprising a DNA molecule that one or more DNA sequences have been linked in a functionally operative manner. Such recombinant DNA constructs or vectors are capable of introducing a 5' regulatory sequence or promoter region and a DNA sequence for a selected gene product into a cell in such a manner that the DNA sequence is transcribed into a functional mRNA that is translated and therefore expressed. Recombinant DNA constructs or recombinant vectors may be constructed to be capable of expressing antisense RNAs, in order to inhibit translation of a specific RNA of interest.

"Regeneration" refers to the process of growing a plant from a plant cell (e.g., plant protoplast or explant).

"Transcription" refers to the process of producing an RNA copy from a DNA template.

"Transformation" refers to a process of introducing an exogenous nucleic acid sequence (e.g., a vector, recombinant nucleic acid molecule) into a cell or protoplast that exogenous nucleic acid is incorporated into a chromosome or is capable of autonomous replication.

"Transformed" or "transgenic" refers to a cell, tissue, organ, or organism into that has been introduced a foreign nucleic acid, such as a recombinant vector. A "transgenic" or "transformed" cell or organism also includes progeny of the cell or organism and progeny produced from a breeding program employing such a "transgenic" plant as a parent in a cross and exhibiting an altered phenotype resulting from the presence of the foreign nucleic acid.

The term "transgene" refers to any nucleic acid sequence nonnative to a cell or organism transformed into said cell or organism. "Transgene" also encompasses the component parts of a native plant gene modified by insertion of a nonnative nucleic acid sequence by directed recombination.

"Vector" refers to a plasmid, cosmid, bacteriophage, or virus that carries foreign DNA into a host organism.

Following are Examples presented to illustrate the present invention and are not intended to limit the scope of this invention. The examples will permit better understanding of the invention and perception of its advantages and certain variations of execution.

EXAMPLES

The following Examples are presented to illustrate the present invention and are not intended to limit the scope of this invention. The examples will permit better understanding of the invention and perception of its advantages and certain variations of execution. All glyphosate concentrations are on a glyphosate acid equivalent (a.e.) basis and all concentrations are on a weight basis unless stated otherwise.

In the following Examples 1, M1-M4, AO1, H1, H2, D1, M9 and M10, greenhouse tests were conducted to evaluate the relative effectiveness of compositions in reducing PMIDA-induced necrosis in ROUNDUP READY FLEX cotton. Compositions for comparative purposes included the following:

Composition A: which consists of approximately 37.2% a.e. by weight of glyphosate IPA salt in aqueous solution together with approximately 11.7% surfactant. The surfactant was a blend of an alkoxylated alkylamine and an alkoxylated phosphate ester. The IPA salt of glyphosate was made from a technical grade glyphosate having <100 ppm PMIDA (dry weight basis) resulting in non-detectable levels of PMIDA level in the composition.

Composition B: which consists of approximately 39.6% a.e. by weight of glyphosate potassium salt in aqueous solution together with approximately 10% surfactant. The surfactant was a blend of alkoxylated coco and tallow amines. The potassium salt of glyphosate was made from a technical grade glyphosate having <100 ppm PMIDA (dry weight basis) resulting in non-detectable levels of PMIDA level in the composition.

Composition C: which contains approximately 37.2% a.e. by weight of glyphosate IPA salt in aqueous solution together with approximately 12% surfactant. The surfactant was a blend of an alkoxylated alkylamine and an alkoxylated phosphate ester. The composition contained 280 ppm PMIDA, equivalent to approximately 720 ppm PMIDA (dry weight basis) in the technical grade glyphosate from which the composition was prepared.

Composition D: sold by Monsanto Company as ROUNDUP WEATHERMAX and containing approximately 39.9% a.e. by weight of glyphosate potassium salt in aqueous solution. The PMIDA concentration was determined to be 1890 ppm, equivalent to approximately 4760 ppm PMIDA (dry weight basis) in the technical grade glyphosate from which the composition was prepared.

Composition E: which contains approximately 37.2% a.e. by weight of glyphosate IPA salt in aqueous solution together with approximately 11.7% surfactant. The surfactant was a blend of an alkoxylated alkylamine and an alkoxylated phosphate ester. The IPA salt of glyphosate was made from a technical grade glyphosate having 1880 ppm PMIDA (dry weight basis) resulting a PMIDA level in the composition of 730 ppm.

Composition F: sold by Monsanto Company as ROUNDUP WEATHERMAX and containing approximately 39.4% a.e. by weight of glyphosate potassium salt in aqueous solution. The PMIDA concentration was determined to be 550 ppm, equivalent to approximately 1340 ppm PMIDA (dry weight basis) in the technical grade glyphosate from which the composition was prepared.

Composition G: was prepared by blending two samples of commercial ROUNDUP WEATHERMAX sold by Monsanto Company containing glyphosate potassium salt in aqueous solution. The blend comprised approximately 56.4% of a sample containing 0.085% PMIDA and 43.6% of another sample containing 0.174% PMIDA. The resulting blend contained 0.1238% PMIDA, equivalent to approximately 0.300% PMIDA (dry weight basis) in the technical grade glyphosate from which the samples were prepared.

Composition H: sold by Monsanto Company as ROUNDUP WEATHERMAX and containing approximately 39.5% a.e. by weight of glyphosate potassium salt in aqueous solution and 0.205% PMIDA, equivalent to approximately 0.498% PMIDA (dry weight basis) in the technical grade glyphosate from which the composition was prepared.

Composition I: sold by Monsanto Company as ROUNDUP WEATHERMAX and containing approximately 39.8% a.e. by weight of glyphosate potassium salt in aqueous solution. The PMIDA concentration was determined to be 1740 ppm, equivalent to approximately 4190 ppm PMIDA (dry weight basis) in the technical grade glyphosate from which the composition was prepared.

For greenhouse testing of the glyphosate concentrates, 30 mL spray solutions were prepared as follows:
1. A stock solution was prepared for each concentrate sprayed by adding 14.502 g of concentrate to 15.50 g de-ionized (DI) water.
2. From the stock solution, the following dilutions were made to prepare the actual spray solution (total volume of 30 mL).

| Rate Desired | Stock Solution (mL) | DI Water (mL) |
| --- | --- | --- |
| 1X (1260 g/ha) | 2.11 | 27.89 |
| 2X (2520 g/ha) | 4.22 | 25.78 |
| 4X (5040 g/ha) | 8.43 | 21.57 |

Greenhouse Testing

The following greenhouse testing procedure provides a highly reproducible assay for showing PMIDA-induced necrosis in ROUNDUP READY FLEX cotton and was used for evaluating compositions of the Examples to determine their effectiveness in reducing the necrosis.

1. Two seeds of a ROUNDUP READY FLEX cotton variety were planted in six inch round plastic pots containing a commercially available potting mix (Redi-Earth), supplemented with fertilizer (Osmocote 14-14-14 slow release, 100 g/ft$^3$).
2. Pots were then placed in a greenhouse with the following conditions: 33° C. day/21° C. night, variable relative humidity, and 14-hour day-length. Water was provided as needed through sub-irrigation.
3. Upon emergence plants were thinned to one per pot.
4. Plants were grown for 21-25 days in order to achieve a minimum growth stage of four true leaves (five-six leaves was preferred).
5. Plants were then transferred to a growth chamber with the following conditions: 27° C./60% relative humidity day, 15° C./80% relative humidity night, and 14-hour day-length. Plants were maintained in these conditions for forty-eight hours.
6. Plants were removed from the growth chamber for an application of glyphosate with a known level of PMIDA. Applications were made utilizing a standard research track sprayer with a single spray nozzle (flat fan even spray tip). The sprayer was calibrated to deliver ninety-four liters of spray solution per hectare at a spray pressure of 165 kPa. Glyphosate application rates varied depending upon the objectives of the test, but typically were 1260, 2520 and 5040 g/ha which are, respectively, 1×, 2× and 4× of the highest proposed field use rates on ROUNDUP READY FLEX cotton.
7. When applications were complete the plants were returned to the growth chamber for another forty-eight hour incubation under the conditions listed in number 5 above.
8. Plants were evaluated at this point, two days after treatment (2 DAT), with a visual assessment of percent necrosis (tissue death) relative to an untreated check plant. Maximum injury was evident at this time point.
9. Resulting assessment data was statistically evaluated by least significant difference (LSD). The LSD is a valid statistical test procedure for evaluating multiple comparisons. The magnitude of the LSD value is related to the variability across replicates for each comparison. The greater the variability among replicates the higher the LSD value. Comparisons are thus made between mean values generated across replicates. The LSD, typically provided as a 95% confidence limit (LSD 0.05), specifies the minimum degree of difference between mean comparisons that would be considered statistically significant. In other words one is 95% sure that this minimum difference is statistically valid. For example, where Treatment A mean value is 10, Treatment B mean value is 15, and Treatment C mean value is 20. Calculated LSD (0.05) is 7.2. The difference between Treatment A and Treatment C would be considered statistically significant, whereas Treatment B would not be considered statistically different from either Treatment A or Treatment C.

Example 1

Aqueous concentrate compositions were prepared containing PMIDA at known concentrations. For composition A-1, 0.05 g of dry PMIDA (99% assay) were added to 100 g of composition A and stirred until the PMIDA was dissolved. PMIDA concentrations reported in these Examples were determined or confirmed by high-pressure liquid chromatography (HPLC) analysis in accordance with the procedure in Example 3 below. Compositions A-2 and A-3 were prepared in like manner using 0.15 g and 0.20 g PMIDA, respectively.

TABLE 1a

| Composition | PMIDA g/ha (1X, 2X, 4X rates) | % necrosis (2 DAT) | | |
|---|---|---|---|---|
| | | 1260 g/ha | 2520 g/ha | 5040 g/ha |
| A | nd, nd, nd* | 0 | 0 | 4 |
| C | 0.95, 1.90, 3.79 | 0 | 0 | 15 |
| A-1 | 1.69, 3.39, 6.77 | 0 | 6 | 65 |
| E | 2.47, 4.95, 9.89 | 0 | 25 | 66 |
| A-2 | 5.08, 10.16, 20.3 | 4 | 40 | 83 |
| D | 5.97, 11.9, 23.9 | 9 | 51 | 79 |
| A-3 | 6.77, 13.6, 27.1 | 9 | 61 | 83 |
| LSD (0.05) | | 4.4 | 9.2 | 8.8 |

*nd = not detected

Results show a clear titration effect as increasing levels of PMIDA cause a proportionate rise in necrosis. Maximum necrosis appears to reach a plateau at the 80-85% range as noted with the highest application rate and higher levels of PMIDA.

Example M1

Spray solutions for glyphosate application rates of 2520 and 5040 g/ha were prepared using composition D. All metal salts were tank-mixed at a glyphosate:metal salt weight ratio of 10:1. For each spray solution, the amount of metal salt required to give the 10:1 ratio was dissolved in an equal amount of water. This 50% w/w metal salt solution was then mixed with the requisite amount of composition D and water to provide the desired volume of spray solution. This resulted in Metal:PMIDA molar ratios as follows:

| Metal Salt | CAS Number | Metal:PMIDA Molar Ratio |
|---|---|---|
| Ferric chloride | 7705-08-0 | 29.6:1 |
| Nickel sulfate hexahydrate | 10101-97-0 | 18.2:1 |
| Aluminum chloride hexahydrate | 7784-13-6 | 19.9:1 |
| Cupric Nitrate (2.1) hydrate | 19004-19-4 | 20.6:1 |
| Zinc sulfate heptahydrate | 7446-20-0 | 16.7:1 |
| Magnesium sulfate heptahydrate | 10034-99-8 | 19.5:1 |
| Calcium chloride (anhydrous) | 10043-52-4 | 43.2:1 |

TABLE M1a

| | % necrosis (2 DAT) | | Necrosis Reduction Relative to Control | |
|---|---|---|---|---|
| Glyphosate (g/ha) | 2520 | 5040 | 2520 | 5040 |
| PMIDA (g/ha) | 11.9 | 23.9 | 11.9 | 23.9 |
| Tank-mix Additive | | | | |
| None | 38 | 78 | na* | na |
| Ferric chloride | 0 | 2 | 100% | 97% |
| Nickel sulfate | 4 | 28 | 89% | 64% |
| Aluminum chloride | 2 | 23 | 95% | 71% |
| Cupric Nitrate | 3 | 25 | 92% | 68% |
| Zinc sulfate | 10 | 54 | 74% | 31% |
| Magnesium sulfate | 46 | 73 | 0% | 6% |
| Calcium chloride | 26 | 73 | 32% | 6% |
| LSD (0.05) | 6.2 | 8 | | |

*na = not applicable

Several of the metal salts significantly reduce necrosis at both application rates. These included nickel, zinc, aluminum, copper, and iron. Calcium and magnesium, known glyphosate antagonists, had relatively little impact on the degree of necrosis.

Example M2

An aqueous concentrate composition containing Iron(III) Citrate at known Iron:PMIDA molar ratios was prepared from composition F as follows:

| Iron:PMIDA Molar Ratio | Composition F (g) | Iron (III) Citrate (g) |
|---|---|---|
| 1.5:1 | 99.882 | 0.118 |
| 2.5:1 | 99.804 | 0.196 |
| 3.5:1 | 99.725 | 0.275 |

Composition D containing 1890 ppm PMIDA and no iron was used as a control.

TABLE M2a

| | % necrosis (2 DAT) Glyphosate (g/ha) | | | Necrosis Reduction Relative to Control Glyphosate (g/ha) | | |
|---|---|---|---|---|---|---|
| | 1260 | 2520 | 5040 | 1260 | 2520 | 5040 |
| Iron:PMIDA | | | PMIDA (g/ha) | | | |
| (molar ratio) | 1.76 | 3.52 | 7.04 | 1.76 | 3.52 | 7.04 |
| No Iron | 9 | 34 | 71 | na | na | na |
| 1.5:1 | 0 | 2 | 16 | 100% | 94% | 77% |
| 2.5:1 | 0 | 0 | 11 | 100% | 100% | 85% |
| 3.5:1 | 0 | 1 | 9 | 100% | 97% | 87% |
| LSD (0.05) | 1.6 | 3.4 | 7.5 | | | |

Previous studies have shown that a formulation with PMIDA at 549 ppm will produce necrosis of 60-65% at the high application rate.

An aqueous concentrate composition containing Iron(III) Citrate at known Iron:PMIDA molar ratios was prepared from composition G as follows:

| Iron:PMIDA Molar Ratio | Composition G (g) | Iron (III) Citrate (g) |
|---|---|---|
| 1.5:1 | 99.735 | 0.265 |
| 2.5:1 | 99.559 | 0.441 |
| 3.5:1 | 99.484 | 0.616 |

Composition D containing 1890 ppm PMIDA and no iron was used as a control.

TABLE M2b

| | % necrosis (2 DAT) Glyphosate (g/ha) | | | Necrosis Reduction Relative to Control Glyphosate (g/ha) | | |
|---|---|---|---|---|---|---|
| | 1260 | 2520 | 5040 | 1260 | 2520 | 5040 |
| | | | PMIDA (g/ha) | | | |
| Iron citrate:PMIDA | 3.95 | 7.90 | 15.8 | 3.95 | 7.90 | 15.8 |
| No Iron | 9 | 34 | 71 | na | na | na |
| 1.5:1 | 0 | 3 | 30 | 100% | 91% | 58% |
| 2.5:1 | 0 | 1 | 18 | 100% | 97% | 75% |
| 3.5:1 | 0 | 1 | 11 | 100% | 97% | 85% |
| LSD (0.05) | 1.6 | 3.4 | 7.5 | | | |

Previous studies have shown that a formulation with PMIDA at 1238 ppm will produce necrosis at slightly lower levels than that of composition D at all three application rates.

An aqueous concentrate composition containing Iron(III) Citrate at known Iron:PMIDA molar ratios was prepared from composition H as follows:

| Iron:PMIDA Molar Ratio | Composition H (g) | Iron(III) Citrate (g) |
|---|---|---|
| 1.5:1 | 99.562 | 0.438 |
| 2.5:1 | 99.272 | 0.728 |
| 3.5:1 | 98.984 | 1.016 |

Composition D containing 1890 ppm PMIDA and no iron was used as a control.

TABLE M2c

| | % necrosis (2 DAT) Glyphosate (g/ha) | | | Necrosis Reduction Relative to Control Glyphosate (g/ha) | | |
|---|---|---|---|---|---|---|
| | 1260 | 2520 | 5040 | 1260 | 2520 | 5040 |
| | | | PMIDA (g/ha) | | | |
| Iron citrate:PMIDA | 6.54 | 13.08 | 26.16 | 6.54 | 13.08 | 26.16 |
| No Iron | 9 | 34 | 71 | na | na | na |
| 1.5:1 | 0 | 18 | 43 | 100% | 47% | 39% |
| 2.5:1 | 0 | 2 | 31 | 100% | 94% | 56% |
| 3.5:1 | 0 | 0 | 30 | 100% | 100% | 58% |
| LSD (0.05) | 1.6 | 3.4 | 7.5 | | | |

Previous experience has shown that the composition with 2050 PMIDA will cause slightly more necrosis than composition D with 1890 ppm PMIDA.

Example M3

An aqueous concentrate composition containing iron(III) citrate in a 2.5:1 molar ratio with PMIDA was prepared by mixing together 99.559 g of composition G and 0.441 g iron(III) citrate.

An aqueous concentrate composition containing iron(III) sulfate plus citric acid having an iron:PMIDA molar ratio of 2.5:1 was prepared by first dissolving 15.638 g iron(III) sulfate pentahydrate (CAS Number 15244-10-7) into 46.48 g of a 50% aqueous solution of citric acid to make an "iron sulfate+citric acid" premix. Then 1.381 g of the premix was added drop-wise to 98.619 g composition G while stirring continuously.

An aqueous concentrate composition containing iron(III) ethylenediaminetetraacetic acid having an iron:PMIDA molar ratio of 2.5:1 was prepared by mixing together 99.434 g of composition G and 0.566 g iron(III) EDTA sodium salt hydrate (CAS Number 15708-41-5).

TABLE M3a

|  | % necrosis (2 DAT) | | | Necrosis Reduction Relative to Control | | |
|---|---|---|---|---|---|---|
|  | Glyphosate (g/ha) | | | | | |
|  | 1260 | 2520 | 5040 | 1260 | 2520 | 5040 |
|  | PMIDA (g/ha) | | | | | |
| Iron Addition | 3.95 | 7.90 | 15.8 | 3.95 | 7.90 | 15.8 |
| None | 9 | 34 | 71 | na | na | na |
| Iron citrate | 0 | 1 | 18 | 100% | 97% | 75% |
| Iron sulfate + citric acid | 0 | 2 | 20 | 100% | 94% | 72% |
| Iron + EDTA | 0 | 11 | 39 | 100% | 68% | 45% |
| LSD (0.05) | 1.6 | 3.4 | 7.5 | | | |

There was no significant difference between iron citrate and iron sulfate plus citric acid relative to the reduction in necrosis at any application rate. Iron plus EDTA was significantly less effective.

Example M4

The metal salt compositions in this Example were prepared as in Example M3 except that the metal salts were added to composition I which has 1740 ppm PMIDA. Mixtures were prepared containing 1.5:1, 2.5:1 or 3.5:1 Metal:PMIDA molar ratios.

TABLE M4a

|  |  | % necrosis (2DAT) | | | Necrosis Reduction Relative to Control | | |
|---|---|---|---|---|---|---|---|
|  |  | Glyphosate (g/ha) | | | | | |
|  |  | 1260 | 2520 | 5040 | 1260 | 2520 | 5040 |
|  |  | PMIDA (g/ha) | | | | | |
| Metal Addition | metal:PMIDA | 5.51 | 11.0 | 22.0 | 5.51 | 11.0 | 22.0 |
| None |  | 6 | 43 | 63 | na | na | Na |
| zinc sulfate + citric acid | 1.5:1 | 2 | 40 | 67 | 67% | 7% | 0% |
| zinc sulfate + citric acid | 2.5:1 | 1 | 28 | 67 | 83% | 35% | 0% |
| zinc sulfate + citric acid | 3.5:1 | 4 | 23 | 60 | 33% | 47% | 5% |
| zinc oxide + citric acid | 1.5:1 | 9 | 47 | 63 | 0% | 0% | 0 |
| zinc oxide + citric acid | 2.5:1 | 3 | 43 | 72 | 50% | 0% | 0% |
| zinc oxide + citric acid | 3.5:1 | 1 | 38 | 57 | 83% | 12% | 10% |
| Ferric sulfate + citric acid | 1.5:1 | 0 | 20 | 57 | 100% | 53% | 10% |
| ferric sulfate + citric acid blended with | 1.5:1 | | | | | | |
| zinc oxide + citric acid | 2.5:1 | 0 | 8 | 60 | 100% | 81% | 5% |
| LSD (0.05) |  | 3.1 | 9.2 | 10.4 | | | |

Ferric sulfate plus citric acid was significantly more effective in reducing necrosis than either zinc sulfate plus citric acid or zinc oxide plus citric acid. Ferric sulfate plus citric acid and zinc sulfate plus citric acid combined in the same formulation showed a significantly greater degree of necrosis reduction at the 2520 g/ha glyphosate application rate than ferric sulfate plus citric acid alone.

Example AO1

Spray solutions for glyphosate application rates of 2520 and 5040 g/ha were prepared using composition D. All antioxidants were tank-mixed at a glyphosate:antioxidant weight ratio of 10:1. This resulted in an antioxidant:PMIDA weight ratio of 22:1. The sodium sulfite and L-ascorbic acid were added to the spray solutions as solids. Butylated hydroxy anisole and butylated hydroxyl toluene were added as 33% solutions in 2-ethyl-1-hexanol. The hydroquinone was added as a 33% solution in ethanol and the resorcinol was added as a 50% aqueous solution.

TABLE AO1a

|  | % necrosis (2 DAT) | | Necrosis Reduction Relative to Control | |
|---|---|---|---|---|
| Glyphosate (g/ha) | 2520 | 5040 | 2520 | 5040 |
| PMIDA (g/ha) | 11.9 | 23.9 | 11.9 | 23.9 |
| Tank-mix Additive | | | | |
| None | 49 | 78 | na | na |
| butylated hydroxy anisole | 10 | 55 | 80% | 29% |
| butylated hydroxy toluene | 10 | 60 | 80% | 23% |
| Hydroquinone | 15 | 74 | 69% | 5% |
| Resorcinol | 14 | 61 | 71% | 22% |
| L-ascorbic acid | 33 | 78 | 33% | 0% |
| Sodium sulfite | 30 | 83 | 39% | 0% |
| LSD (0.05) | 6.1 | 7.8 | | |

All antioxidants significantly reduced necrosis at the 2520 g a.e./ha application rate. Butylated hydroxy anisole, butylated hydroxy toluene, and resorcinol also significantly reduced necrosis at the higher application rate.

Example H1

Spray solutions for glyphosate application rates of 2520 and 5040 g/ha were prepared using composition D. Additionally, urea (50% w/w solution) or glycerin were added to the spray solution on a % volume/volume (v/v) basis.

TABLE H1a

|  | % Necrosis (2 DAT) | | Necrosis Reduction Relative to Control | |
|---|---|---|---|---|
| Glyphosate (g/ha) | 2520 | 5040 | 2520 | 5040 |
| PMIDA (g/ha) | 11.9 | 23.9 | 11.9 | 23.9 |
| Tank-mix Additive Study 1 | | | | |
| None | 33 | 76 | na | na |
| glycerin 2% v/v | 29 | 65 | 12% | 14% |
| glycerin 4% v/v | 18 | 45 | 45% | 41% |
| LSD (0.05) | 6.4 | 9.5 | | |

TABLE H1a-continued

|  | % Necrosis (2 DAT) |  | Necrosis Reduction Relative to Control | |
| --- | --- | --- | --- | --- |
| Study 2 | | | | |
| None | 28 | 86 | na | na |
| glycerin 4% v/v | 5 | 70 | 82% | 19% |
| urea 8% v/v | 18 | 75 | 36% | 13% |
| LSD (0.05) | 7 | 7.8 | | |

Glycerin (4% v/v) and urea (8% v/v) significantly reduced necrosis in ROUNDUP READY FLEX cotton.

Example H2

Various proprietary additives were used in the compositions of this Example. They may be identified as follows:

| Trade Name | Chemical Description |
| --- | --- |
| Surfynol 104A | tetramethyl-6-decyne-4,7-diol |
| Surfonic ADA-170 | ethylenediamine ethoxylate |
| Tetronic 304 | ethylenediamine ethoxylate/propoxylate |
| Pluronic L64 | EO/PO block copolymer |
| Agrimul PG 2069 | decyl polyglucose |

Spray solutions for glyphosate application rates of 2520 and 5040 g/ha were prepared using composition D. All tank-mix additives were tested at a glyphosate:additive weight ratio of 10:1. Tank-mix additives were added to the spray solution in neat form except for the following:

| Tank-mix Additive | Form Added to Spray Solution |
| --- | --- |
| Polyethylene glycol 900 | 50% aqueous solution |
| Surfynol 104A | 50% solution in ethyl hexyl alcohol |
| Agrimul PG 2069 | 50% aqueous solution |
| Corn syrup (light) | 50% aqueous solution |
| trimethylol-propane | 50% aqueous solution |

TABLE H2a

|  | % Necrosis (2 DAT) | | Necrosis Reduction Relative to Control | |
| --- | --- | --- | --- | --- |
| Glyphosate (g/ha) | 2520 | 5040 | 2520 | 5040 |
| PMIDA (g/ha) | 11.9 | 23.9 | 11.9 | 23.9 |
| Tank-mix Additive | | | | |
| None | 46 | 79 | na | na |
| propylene glycol | 49 | 81 | 0% | 0% |
| dipropylene glycol | 45 | 80 | 2% | 0% |
| Ethylene glycol | 40 | 78 | 13% | 1% |
| Diethylene glycol | 28 | 73 | 39% | 8% |
| triethylene glycol | 40 | 75 | 13% | 5% |
| polyethylene glycol 200 | 35 | 71 | 24% | 10% |
| polyethylene glycol 900 | 31 | 75 | 33% | 5% |
| 2-methyl-2,4-pentanediol | 34 | 73 | 26% | 8% |
| 1,4-butanediol | 28 | 73 | 39% | 8% |
| 3-hexyne-2,5-diol | 33 | 80 | 28% | 0% |
| Surfynol 104A | 23 | 73 | 50% | 8% |
| Surfonic ADA-170 | 33 | 73 | 28% | 8% |
| Tetronic 304 | 45 | 80 | 2% | 0% |
| Triethanolamine | 34 | 76 | 26% | 4% |
| Triisopropanolamine | 49 | 84 | 0% | 0% |
| Pluronic L64 | 50 | 76 | 0% | 4% |
| Agrimul PG 2069 | 36 | 80 | 22% | 0% |
| Glycerol propoxylate, mw 260 (1PO/OH) | 38 | 78 | 17% | 1% |
| Corn syrup (light) | 55 | 86 | 0% | 0% |
| trimethylol-propane | 53 | 84 | 0% | 0% |
| LSD (0.05) | 8.8 | 6.6 | | |

Several of these additives significantly decreased necrosis at the 2520 g/ha application rate. These included diethylene glycol, polyethylene glycol 200, polyethylene glycol 900, 2-methyl-2,4-pentanediol, 1,4-butanediol, 3-hexyne-2,5-diol, Surfynol 104A, Surfonic ADA-170, triethanolamine, and Agrimul PG 2069.

Example D1

Spray solutions for glyphosate application rates of 2520 and 5040 g/ha were prepared using composition D. Dyes were tested at a glyphosate:dye weight ratio of 10:1, 100:1 or 1000:1. The dyes were added to the spray solution as aqueous solutions with the following concentrations: FD&C Yellow #5 and FD&C Blue #1 were at 15% while the remaining dyes were at 10%.

TABLE D1a

|  |  | % necrosis (2 DAT) | | Necrosis Reduction Relative to Control | |
| --- | --- | --- | --- | --- | --- |
|  |  | Glyphosate (g/ha) | | | |
|  |  | 2520 | 5040 | 2520 | 5040 |
|  |  | PMIDA (g/ha) | | | |
| Tank-mix Additive | glyphosate:dye | 11.9 | 23.9 | 11.9 | 23.9 |
| Study 1 | | | | | |
| None | | 49 | 78 | na | na |
| FD&C Yellow #5 | 10:1 | 2 | 35 | 96% | 55% |
| LSD (0.05) | | 6.1 | 7.8 | | |
| Study 2 | | | | | |
| None | | 38 | 78 | na | na |
| FD&C Yellow #5 | 10:1 | 6 | 38 | 84% | 51% |
| FD&C Yellow #5 | 100:1 | 31 | 55 | 18% | 29% |
| FD&C Yellow #5 | 1000:1 | 28 | 69 | 26% | 12% |
| FD&C Blue #1 | 10:1 | 13 | 46 | 66% | 41% |
| LSD (0.05) | | 6.2 | 8 | | |
| Study 3 | | | | | |
| None | | 54 | 73 | na | na |
| FD&C Red #40 | 100:1 | 48 | 75 | 11% | 0% |
| FD&C Red #33 | 100:1 | 51 | 75 | 6% | 0% |
| FD&C Violet #1 | 100:1 | 34 | 75 | 37% | 0% |
| Fast Green FCF | 100:1 | 53 | 78 | 2% | 0% |
| Methylene Blue | 100:1 | 28 | 54 | 48% | 26% |
| LSD (0.05) | | 11.6 | 13.2 | | |

Results indicate that dyes in the spray solution that absorb light in the visible light spectrum can decrease necrosis induced by PMIDA.

Example M5

A potassium glyphosate formulation containing iron (III) citrate to mitigate the adverse effects of PMIDA is prepared by simply mixing the following ingredients in a 250 ml beaker. The mixture becomes homogeneous in a few minutes at 23° C.

| Ingredient | Weight Added (grams) | Description |
|---|---|---|
| Potassium Glyphosate Salt Concentrate | 84.2 | 58% K salt of glyphosate acid in water, containing 47.387% a.e. glyphosate, 0.1974% PMIDA |
| Blend of alkoxylated coco and tallow amines | 10.0 | Proprietary Blend |
| Agnique DFM 111S | 0.0075 | A silicone defoamer from Cognis Corporation, Cincinnati, Ohio |
| Iron (III) Citrate | 0.713 | (CAS Number 3522-50-7, containing 17.2% iron) from Sigma-Aldrich, St. Louis, Missouri |
| De-ionized Water | 5.078 | |
| Total weight | 100.00 | |

The finished formulation contains 39.9% a.e. glyphosate, 0.1663% PMIDA, and 0.1226% iron, which is a 3 to 1 mole ratio of iron to PMIDA.

These values are calculated from the amounts and assays of the ingredients.

0.842*47.387% a.e.=39.9% a.e. glyphosate in formulation
0.842*0.1974% PMIDA=0.1663% PMIDA in formulation
(0.713 g iron citrate/100 g)*(17.2% iron in iron citrate) =0.1226% iron in formulation
0.1663 g/(226.97 g/mole of PMIDA)=0.7327×$10^{-3}$ moles PMIDA
0.1226 g/(55.847 g/mole of iron)=2.195×$10^{-3}$ moles iron
The mole ratio of Iron to PMIDA=(2.195/0.7327)=3.0.

Example M6

A potassium glyphosate formulation that uses a mixture of iron sulfate pentahydrate, zinc oxide, and citric acid to mitigate the effects of PMIDA is prepared by mixing the ingredients given in the following table in a 250 ml beaker. Before proceeding, the salts are premixed with citric acid. A 50% citric acid solution is made by mixing 100 g of citric acid (CAS Number 77-92-9, anhydrous) with 100 g of de-ionized water. Adding 25.17 g of iron (III) sulfate pentahydrate (CAS Number 15244-10-7, containing 21.6% iron) to 74.83 g of the 50% citric acid solution yields the iron sulfate+citric acid premix. Adding 10.046 g zinc oxide (CAS Number 1314-13-2, containing 80.35% zinc) to 89.954 g of the 50% citric acid solution, and stirring until the oxide dissolves, produces the zinc premix. The components can now be mixed in a 250 ml beaker with stirring.

| Ingredient | Weight Added (grams) | Description |
|---|---|---|
| Potassium Glyphosate Salt Concentrate | 84.2 | 58% K salt of glyphosate acid in water, containing 47.387% a.e. glyphosate, 0.1974% PMIDA |
| Etheramine surfactant | 7.48 | Proprietary Surfactant |
| Agnique DFM 111S | 0.01 | A silicone defoamer from Cognis Corporation, Cincinnati, Ohio |
| Sethness P212 | 0.01 | Caramel dye from Sethness-Roquette Company, Chicago IL |
| Premix of Iron (III) Sulfate Citric Acid Water | 1.128 Added drop-wise | Amounts by component: 0.284 g iron sulfate hydrate 0.422 g citric acid 0.422 g water |
| Premix of Zinc Oxide Citric acid Water | 1.431 Added drop-wise | Amounts by component: 0.149 g zinc oxide 0.641 citric acid 0.641 water |
| De-ionized Water | 5.741 | |
| Total weight | 100.00 | |

The preparation used the same potassium glyphosate salt concentrate as Example M5, so the finished formulation contains 39.9% a.e. glyphosate and 0.1663% PMIDA. The iron content is 0.06134%, and the zinc content is 0.1197%.

These values are obtained from the salt amount and metal assays of same.

0.284 g iron sulfate/100 g*21.6% iron in salt=0.06134% iron
0.149 g zinc oxide/100 g*80.35% zinc in oxide=0.1197% zinc
Moles of iron/100 g=0.06134 g/(55.847 g/mole)=1.098× $10^{-3}$ moles
Moles of zinc/100 g=0.1197 g/(65.38 g/mole)=1.831×$10^{-3}$ moles The moles of PMIDA is the same as in Example M5, 0.7327× $10^{-3}$ moles PMIDA.
The mole ratio of iron to PMIDA (1.098/0.7327) is 1.5.
The mole ratio of zinc to PMIDA (1.831/0.7327) is 2.5.

Example M7

The metal salts to be tested were first dissolved in water at a high concentration. This facilitates the handling and dilution required to make the spray solutions. For example 15.0 grams of aluminum chloride hexahydrate (CAS Number 7784-13-6, containing 11.17% Al) was first dissolved in 15 grams water to give a 50% solution in salt. To prepare the application mixture for the 2520 g (glyphosate acid)/ha, wherein the metal salt is to be applied 10 parts glyphosate acid to 1 part metal salt, one needs to use 252.0 g/ha aluminum chloride hexahydrate. The spray volume of water is usually 94 liters/ha. A simple ratio is used to scale the batch size to the amount needed for a small greenhouse application of 0.03 liters. Using composition 270 as the source of glyphosate, containing 0.1890% PMIDA and 39.7% a.e. glyphosate, for the selected rate, (2520 g a.e./ha)/(94 l/ha)="g needed"/0.03l) is solved for "g needed", and one obtains 0.80425 g of glyphosate acid. Dividing by the glyphosate assay of composition 270, 0.80425 g a.e./(0.397 g a.e./g of composition=) one determines that 2.026 g of composition 270 must be added to 0.03 liters. The "grams needed" calculation is repeated for the 252.0 g/ha rate for the metal salt, and after dividing by the 50% assay of the premix, one determines that 0.1609 g of the 50% aqueous aluminum chloride hexahydrate premix must be added to the 0.03 liters. This completes the preparation of the spray solution, and the other materials are handled similarly.

Example M8

An isopropyl amine (IPA) glyphosate formulation with a metal salt added to mitigate the effects of PMIDA is prepared by mixing the following ingredients in a 250 ml beaker equipped with a stirrer. Before proceeding, in a separate beaker, 100 grams of an "aluminum and citric acid" premix is made; 16.338 g of citric acid (CAS Number 77-92-9) is dissolved in 49.172 g of de-ionized water, then, while stirring, 34.44 g of aluminum (III) sulfate octadecahydrate (CAS Number 7784-31-8, containing 8.1% aluminum) is added. Continue stirring until the aluminum salt dissolves completely. Once completed, the formulation can be prepared by adding the following.

| Ingredient | Weight Added (grams) | Description |
|---|---|---|
| Isopropyl amine Glyphosate Salt Concentrate | 66.13 | 62% IPA salt of glyphosate acid in water, containing 45.93% a.e. glyphosate, 0.09569% PMIDA |
| Ethoxylated tallow amine | 8.0 | Proprietary Surfactant |
| Premix of Al Sulfate 18Hydrate Citric Acid Water | 0.810 Added drop-wise | Amounts by component: 0.279 g Al sulfate 18hydrate 0.133 g Citric acid 0.398 g Water |
| De-ionized Water | 25.06 | |
| Total weight | 100.00 | |

The finished formulation contains 41% IPA salt of glyphosate, 30.37% a.e. glyphosate, 0.06346% PMIDA, 0.02260% aluminum, and an aluminum to PMIDA mole ratio of 3.

These values were calculated from the amounts and assays of the ingredients.

66.13 g/100 g*62% IPA salt=41.00% IPA salt of glyphosate in formulation 66.13 g/100 g*45.93% a.e. glyphosate=30.37% a.e. glyphosate in formulation 66.13 g/100 g*0.09596% PMIDA=0.06346% PMIDA in formulation 0.279 g/100 g*8.1% Al in salt=0.02260% aluminum in formulation Moles of PMIDA in formulation (0.06346 g/226.97 g/mole) are $0.2796 \times 10^{-3}$ moles.

Moles of aluminum in formulation (0.02260 g/26.98 g/mole) are $0.8377 \times 10^{-3}$ moles.

Example M9

Two spray solution sets (A and B) for glyphosate application to ROUNDUP READY FLEX COTTON were prepared from ROUNDUP WEATHERMAX (Monsanto Company), an aqueous glyphosate potassium salt concentrate. The concentrate used to prepare spray solution set A contained 0.2% PMIDA and the concentrate used to prepare a spray solution set B contained 0.4% PMIDA. For each spray set, six spray solutions were prepared that varied with respect to the amount of added ferric sulfate content. Solution 1 of each spray set was prepared with no ferric sulfate addition and solutions 2 through 6 of each set were prepared with ferric sulfate additions at a molar ratio of metal ion to PMIDA of 0.2:1, 0.4:1, 0.6:1, 0.8:1 and 1:1, respectively. Using the greenhouse testing protocol described above and an application volume of 94 L/hectare, spray solution set A was applied to ROUNDUP READY FLEX cotton at application rates of 1260, 2520 and 5040 grams acid equivalent per hectare and spray solution set B was applied at application rates of 2520 and 5040 grams acid equivalent per hectare.

The results for the evaluation of the two spray solution sets are presented in the following two tables.

% Necrosis 2 DAT for ROUNDUP WEATHERMAX Containing 0.2% by Weight PMIDA and Ferric Sulfate

| Spray Solution | Iron:PMIDA Molar Ratio | % necrosis (2 DAT) | | |
|---|---|---|---|---|
| | | 1260 g a.e./ha | 2520 g a.e./ha | 5040 g a.e./ha |
| 1A | 0 | 2 | 9 | 44 |
| 2A | 0.2:1 | 0 | 4 | 34 |
| 3A | 0.4:1 | 0 | 4 | 38 |
| 4A | 0.6:1 | 0 | 2 | 19 |
| 5A | 0.8:1 | 0 | 0 | 19 |
| 6A | 1.0:1 | 0 | 1 | 24 |
| LSD | | 0.4 | 7.2 | 10.8 |

% Necrosis 2 DAT for ROUNDUP WEATHERMAX Containing 0.4% by Weight PMIDA and Ferric Sulfate

| Spray Solution | Iron:PMIDA Molar Ratio | % necrosis (2 DAT) | |
|---|---|---|---|
| | | 2520 g a.e./ha | 5040 g a.e./ha |
| 1B | 0 | 28 | 66 |
| 2B | 0.2:1 | 14 | 47 |
| 3B | 0.4:1 | 11 | 49 |
| 4B | 0.6:1 | 11 | 45 |
| 5B | 0.8:1 | 3 | 38 |
| 6B | 1.0:1 | 3 | 31 |
| LSD | | 7.2 | 10.8 |

Iron to PMIDA ratios of 0.6:1 and higher significantly reduced necrosis at the two highest application rates with ROUNDUP WEATHERMAX containing 0.2% PMIDA. When the PMIDA level was raised to 0.4%, all iron to PMIDA ratios, including the lowest at 0.2:1, significantly reduced necrosis at both 2520 and 5040 g glyphosate a.e./ha application rates. This may be due to the greater magnitude of necrosis with 0.4% PMIDA allowing for a more clearly discernable decrease in necrosis with iron addition. It should be noted with the higher PMIDA levels that 0.8:1 and 1:1 ratios were the only ones to reduce necrosis below the commercially acceptable level of about 5% at the 2× normal application rate (2520 g/ha). The 1:1 ratio also reduced necrosis to a significantly greater degree than ratios of 0.2:1, 0.4:1, and 0.6:1 at the highest application rate. This would suggest that as PMIDA levels increase and necrosis potential increases, the iron to PMIDA ratio may need to increase to mitigate cotton necrosis, and certainly within the context of ratios of 1:1 and lower.

Example M10

A comparison was made between the standard greenhouse incubation conditions of 27° C./60% relative humidity day, 15° C./80% relative humidity night, 14 hour day, 48 hours before and after glyphosate application (as described in the greenhouse testing protocol and termed "low temp" conditions) versus higher temperature/higher humidity incubation conditions of 35° C./80% relative humidity day, 27° C./80% relative humidity night, 14 hour day, 48 hours before and after glyphosate application (termed "high temp" conditions).

Two spray solutions for glyphosate application to ROUNDUP READY FLEX COTTON were prepared from ROUNDUP WEATHERMAX (Monsanto Company) containing either 0.2% PMIDA or 0.4% PMIDA and without ferric sulfate addition. Using an application volume of 94 L/hectare, each spray solution was applied to ROUNDUP READY FLEX cotton at application rates of 1260, 2520 and 5040 grams acid equivalent per hectare. The greenhouse testing protocol described above was utilized with either the "low temp" incubation conditions or the "high temp" incubation conditions. The results are reported in the table below.

% Necrosis 2 DAT for ROUNDUP WEATHERMAX Containing 0.2% and 0.4% by Weight PMIDA

|  | % necrosis (2 DAT) | | |
| --- | --- | --- | --- |
|  | 1260 g a.e./ha | 2520 g a.e./ha | 5040 g a.e./ha |
| 0.2% PMIDA - low temp | 1 | 9 | 44 |
| 0.2% PMIDA - high temp | 0 | 1 | 8 |
| 0.4% PMIDA - low temp | 0 | 28 | 65 |
| 0.4% PMIDA - high temp | 0 | 0 | 8 |
| LSD | 0.4 | 7.2 | 10.8 |

The data show that high temperature, high humidity incubation conditions result in less PMIDA-induced necrosis than do comparable treatments evaluated under "low temp" incubation conditions.

Example 2

Field Trials

Field trials were conducted at Fredricksburg, Tex., Leland, Miss., and Loxley, Ala., USA. Glyphosate formulations were applied to ROUNDUP READY FLEX cotton at the 5-6 leaf node stage of development or later and was dependent upon environmental conditions to maximize necrosis expression. Application rates were 1250, 1680, and 2520 g glyphosate a.e./ha, representing 1×, 1.5×, and 2× rates. All treatments were replicated four times in each study. Cotton necrosis was evaluated 2 DAT. Eight trials were conducted for each example.

Commercial glyphosate formulations containing known amounts of PMIDA were fortified as necessary with PMIDA and iron to give the compositions listed below for use in the field trials. The iron was added as a solution of ferric sulfate including citric acid as a solubilizing ligand.

| Composition | Formulation | PMIDA (wt %) | Fe:PMIDA Ratio (wt:wt) |
| --- | --- | --- | --- |
| 539 | ROUNDUP WEATHERMAX | 0.06 | No Fe Added |
| 640 | ROUNDUP WEATHERMAX | 0.1 | No Fe Added |
| 922 | ROUNDUP WEATHERMAX | 0.2 | No Fe Added |
| 740 | ROUNDUP WEATHERMAX | 0.3 | No Fe Added |
| 825 | ROUNDUP WEATHERMAX | 0.4 | No Fe Added |
| 739 | ROUNDUP WEATHERMAX | 0.1 | 4:1 |
| 734 | ROUNDUP WEATHERMAX | 0.2 | 1.5:1 |
| 770 | ROUNDUP WEATHERMAX | 0.2 | 2:1 |
| 735 | ROUNDUP WEATHERMAX | 0.2 | 2.5:1 |
| 741 | ROUNDUP WEATHERMAX | 0.3 | 1.3:1 |
| 742 | ROUNDUP WEATHERMAX | 0.4 | 1:1 |
| 736 | ROUNDUP WEATHERMAX | 0.4 | 1.5:1 |
| 737 | ROUNDUP WEATHERMAX | 0.4 | 2:1 |
| 738 | ROUNDUP WEATHERMAX | 0.4 | 2.5:1 |
| 772 | ROUNDUP ORIGINALMAX | 0.1 | No Fe Added |
| 807 | ROUNDUP ORIGINALMAX | 0.2 | No Fe Added |
| 775 | ROUNDUP ORIGINALMAX | 0.3 | No Fe Added |
| 902 | ROUNDUP ORIGINALMAX | 0.4 | No Fe Added |
| 773 | ROUNDUP ORIGINALMAX | 0.1 | 6:1 |
| 743 | ROUNDUP ORIGINALMAX | 0.2 | 1.5:1 |
| 831 | ROUNDUP ORIGINALMAX | 0.2 | 2:1 |
| 744 | ROUNDUP ORIGINALMAX | 0.2 | 2.5:1 |
| 774 | ROUNDUP ORIGINALMAX | 0.2 | 3:1 |
| 776 | ROUNDUP ORIGINALMAX | 0.3 | 2:1 |
| 745 | ROUNDUP ORIGINALMAX | 0.4 | 1.5:1 |
| 746 | ROUNDUP ORIGINALMAX | 0.4 | 2:1 |
| 747 | ROUNDUP ORIGINALMAX | 0.4 | 2.5:1 |
| 817 | ROUNDUP ORIGINAL | 0.4 | 2:1 |

A number of trials were applied relatively early in the season when the cotton was at the 5-6 leaf node stage and environmental conditions were cool and dry. There was no necrosis evident in any of these early trials. Later trials sprayed over 8-12 leaf node stage cotton with hot temperatures, high relative humidity, and abundant soil moisture showed high levels of necrosis with compositions containing no iron. The analyses that follow include only trials where necrosis was observed. T-test analyses combine data across trials and application rates.

Example 2A

Figure 5:
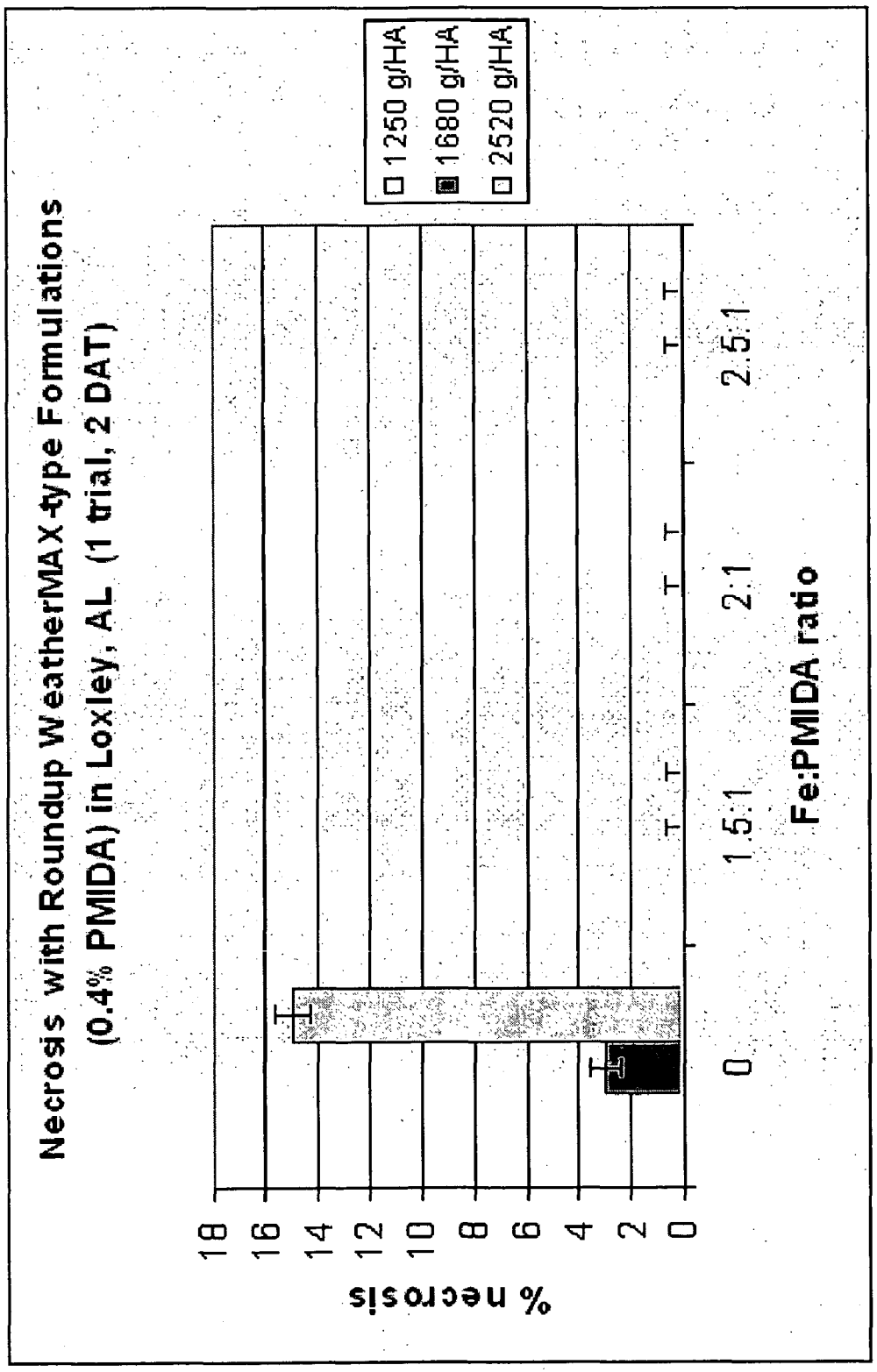
FIG. 5 is a graphical representation of the degree of necrosis reduction in ROUNDUP READY FLEX cotton 2 days after treatment (2 DAT) following field application of ROUNDUP WEATHERMAX-type glyphosate herbicidal formulations (0.4% PMIDA) safened with ferric sulfate addition in Example 2A.

This example investigated ROUNDUP WEATHERMAX-type compositions with set levels of PMIDA (0.2% or 0.4%) and varying ratios of iron to PMIDA. Necrosis was evident in one trial and only at the higher level of PMIDA (composition 825, 0.4% PMIDA). All iron containing compositions with 0.4% PMIDA showed significantly less necrosis than the standard (Table 2A). Necrosis reduction was similar for all iron containing compositions regardless of the iron to PMIDA ratio (1.5:1, 2:1, or 2.5:1). An example of the degree of necrosis reduction is shown in FIG. 5.

TABLE 2A

T-Test Pairwise Mean Comparisons For 1 Experiment Compositions compared to 825 as a Standard - Overall and by Species

| Standard | Composition | % Difference In Necrosis | Significance | n |
| --- | --- | --- | --- | --- |
| 825 | 736 | 6.1 | ‡ | 12 |
| 825 | 737 | 6.1 | ‡ | 12 |
| 825 | 738 | 6.1 | ‡ | 12 |

‡ Composition shows significantly less necrosis than Standard ($p < 0.05$)

Example 2B

Figure 6:
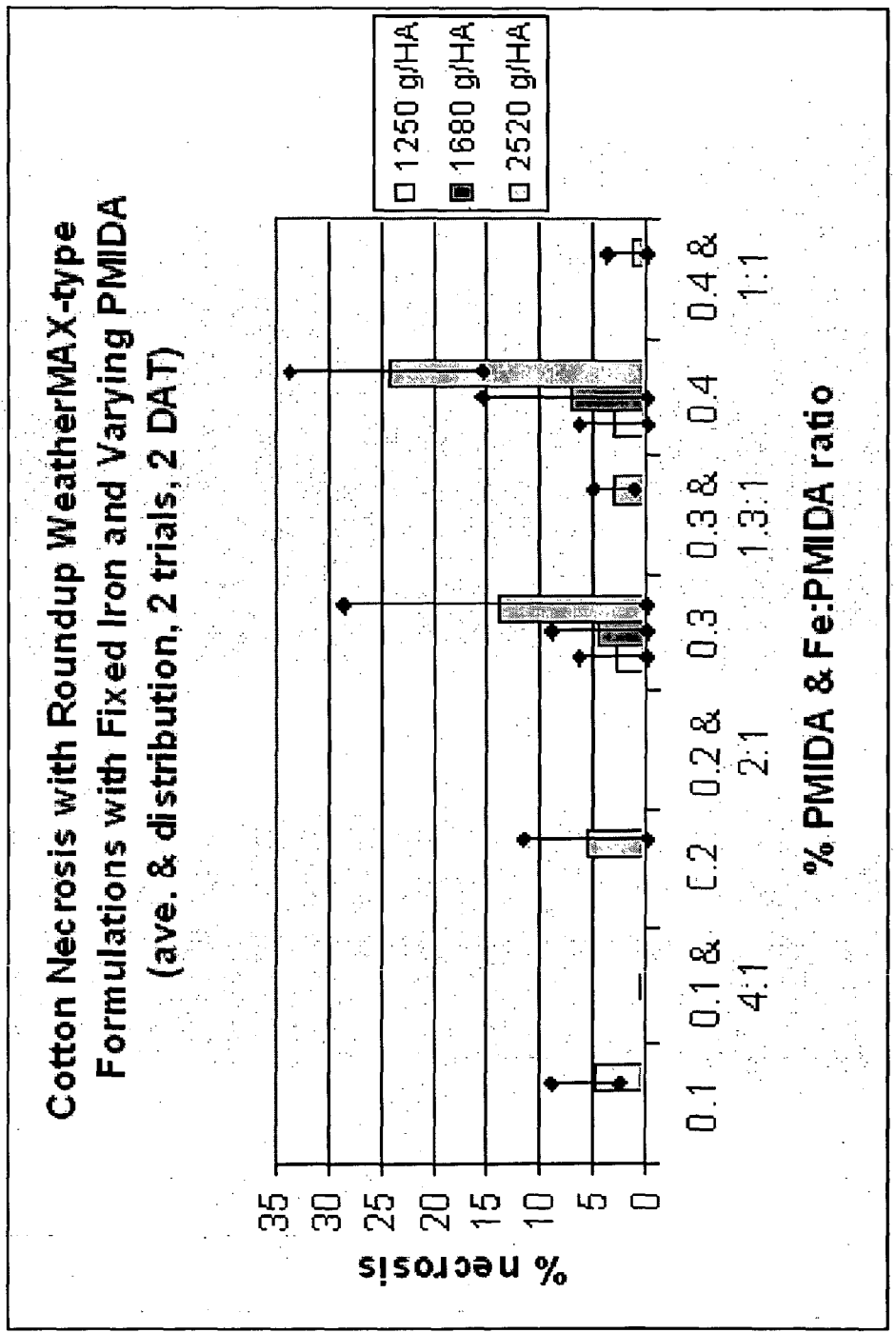
FIG. 6 is a graphical representation of the degree of necrosis reduction in ROUNDUP READY FLEX cotton 2 days after treatment (2 DAT) following field application of ROUNDUP WEATHERMAX-type glyphosate herbicidal formulations with varying PMIDA levels and safened with fixed levels of iron in Example 2B.

This example investigated ROUNDUP WEATHERMAX-type compositions with constant levels of iron and varying levels of PMIDA. Necrosis was evident in two of the eight trials. Due to the low levels of necrosis with compositions containing 0.1% and 0.2% PMIDA, differences between compositions with and without iron were not evident. When the level of PMIDA was 0.3% or 0.4%, compositions containing iron showed significantly less necrosis than compositions with no iron (Table 2B). FIG. 6 graphically represents the data.

TABLE 2B

T-Test Pairwise Mean Comparisons For 2 Experiments
Compositions compared to 640, 922, 740, or 825 as a Standard

| Standard | Composition | % Difference In Necrosis | Significance | N |
|---|---|---|---|---|
| 640 | 739 | 1.3 | − | 24 |
| 922 | 770 | 1.9 | − | 24 |
| 740 | 741 | 6.0 | ‡ | 24 |
| 825 | 742 | 11.1 | + | 24 |

− Composition can not be distinguished from Standard ($p \geq 0.05$)
‡ Composition shows significantly less necrosis than Standard ($p < 0.05$)
+ Composition shows significantly less necrosis than Standard ($p < 0.01$)

Example 2C

Figure 7:
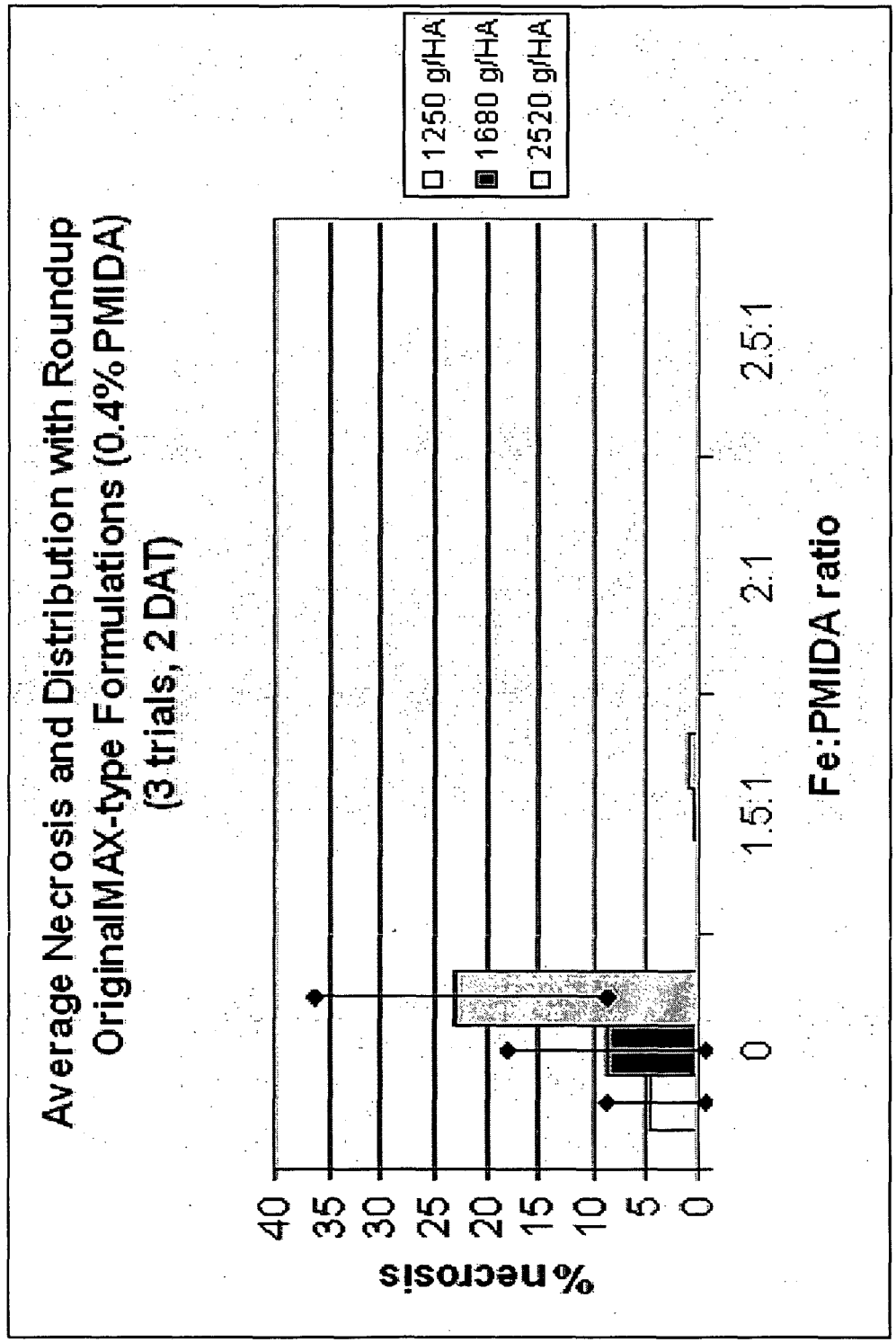
FIG. 7 is a graphical representation of the average necrosis and distribution in ROUNDUP READY FLEX cotton 2 days after treatment (2 DAT) following field application of ROUNDUP ORIGINALMAX-type glyphosate herbicidal formulations (0.4% PMIDA) and varying ratios of iron to PMIDA in Example 2C.

This example investigated the ability of iron to mitigate necrosis in ROUNDUP ORIGINALMAX-type compositions with set levels of PMIDA (0.2 or 0.4%) and varying ratios of iron to PMIDA (1.5:1, 2:1, or 2.5:1). Necrosis was evident in three of the eight trials. All compositions containing iron showed significantly less necrosis than the relevant standards, composition 807 (0.2% PMIDA) and composition 902 (0.4% PMIDA) (Table 2C). The decrease in necrosis was similar for all ratios of iron to PMIDA (1.5:1, 2:1 or 2.5:1) and necrosis was essentially eliminated (FIG. 7).

TABLE 2C

T-Test Pairwise Mean Comparisons For 3 Experiments
Compositions compared to 807 or 902 as a Standard

| Standard | Composition | % Difference In Necrosis | Significance | n |
|---|---|---|---|---|
| 807 | 831 | 2.1 | ‡ | 35 |
| 807 | 744 | 2.3 | + | 36 |
| 807 | 743 | 2.4 | + | 36 |
| 902 | 745 | 10.1 | + | 36 |
| 902 | 746 | 10.4 | + | 36 |
| 902 | 747 | 10.4 | + | 36 |

‡ Composition shows significantly less necrosis than Standard ($p < 0.05$)
+ Composition shows significantly less necrosis than Standard ($p < 0.01$)

Example 2D

Figure 8:
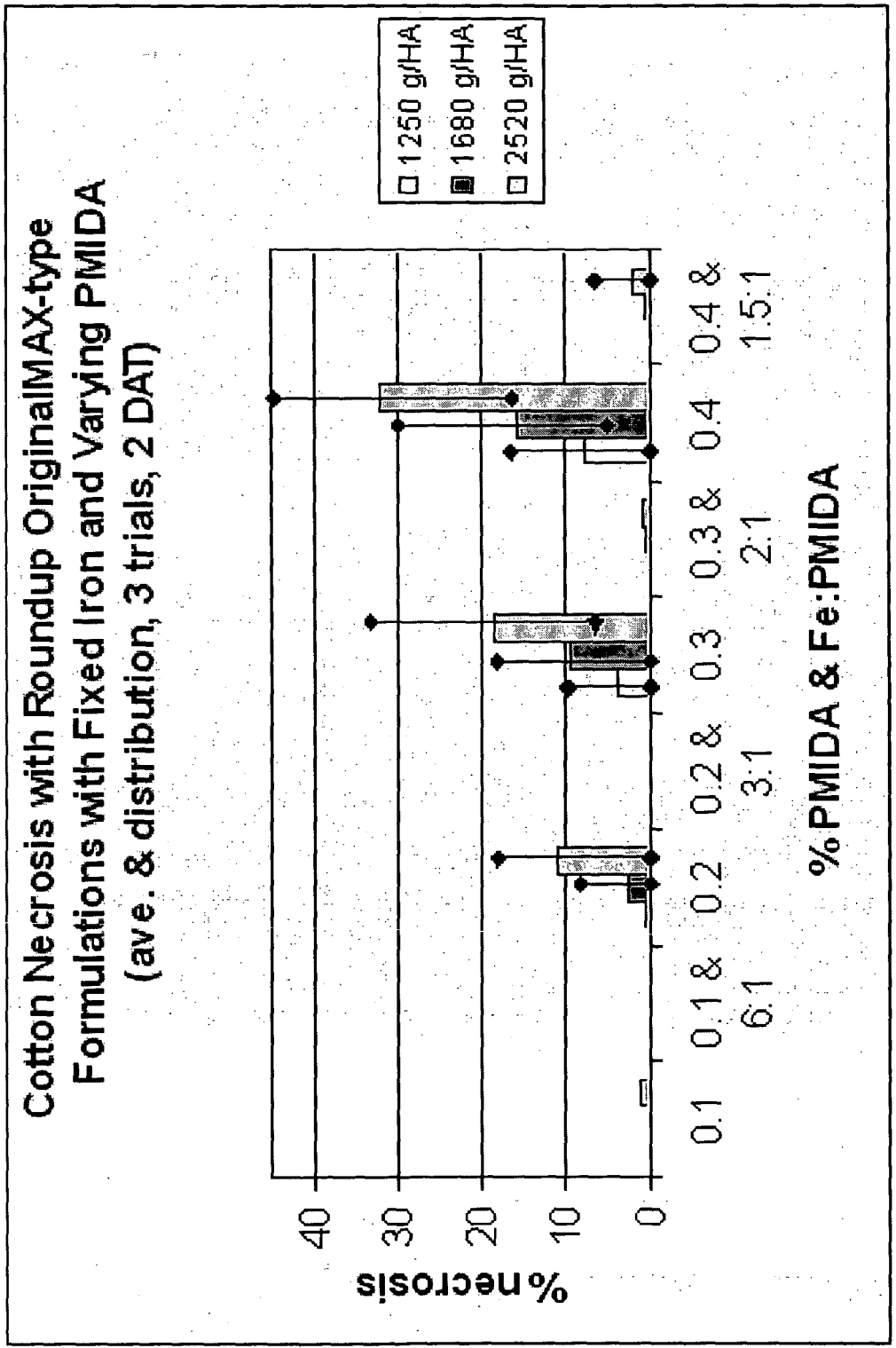
FIG. 8 is a graphical representation of the degree of necrosis reduction in ROUNDUP READY FLEX cotton 2 days after treatment (2 DAT) following field application of ROUNDUP ORIGINALMAX-type glyphosate herbicidal formulations with varying PMIDA levels and safened with fixed levels of iron in Example 2D.

This example investigated ROUNDUP ORIGINALMAX-type compositions with constant levels of iron and varying levels of PMIDA. Necrosis was evident in three of the eight trials. The lack of necrosis with composition 772 (0.1% PMIDA) resulted in no significant differences with composition 773 (Table 2D). The iron containing compositions with higher levels of PMIDA all showed significantly less necrosis than their corresponding compositions without iron. FIG. 8 graphically represents the data

TABLE 2D

T-Test Pairwise Mean Comparisons For 3 Experiments
Compositions compared to 772, 807, 775, or 902 as a Standard

| Standard | Composition | % Difference In Necrosis | Significance | n |
|---|---|---|---|---|
| 772 | 773 | 0.2 | − | 36 |
| 807 | 774 | 4.7 | † | 36 |
| 775 | 776 | 10.3 | † | 36 |
| 902 | 745 | 17.9 | † | 36 |

− Composition can not be distinguished from Standard ($p \geq 0.05$)
† Composition is significantly less efficacious than Standard ($p < 0.01$)

Example 2E

Figure 9:
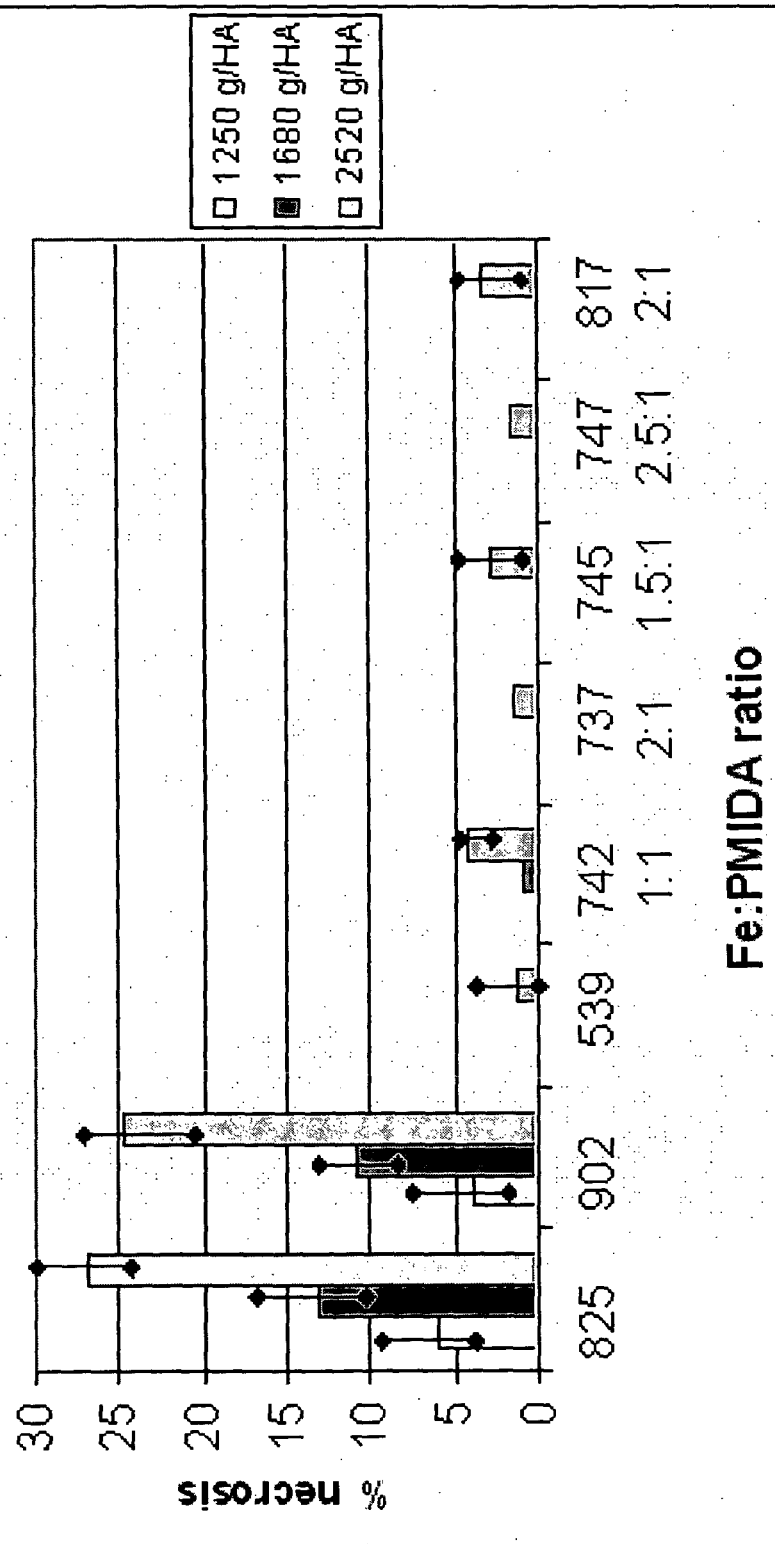
FIG. 9 is a graphical representation of the average necrosis and distribution in ROUNDUP READY FLEX cotton 2 days after treatment (2 DAT) following field application of: ROUNDUP WEATHERMAX or ROUNDUP ORIGINALMAX-type glyphosate herbicidal formulations (0.4% PMIDA) and varying ratios of iron to PMIDA; or ROUNDUP WEATHERMAX-type glyphosate herbicidal formulations of low PMIDA content (0.06% PMIDA) without ferric sulfate addition in Example 2E.

All compositions contained 0.4% PMIDA, except composition 539 (0.06% PMIDA), and varying levels of iron. Those compositions containing iron showed significantly less necrosis than composition 902 (ROUNDUP ORIGINALMAX, 0.4% PMIDA) and composition 825 (ROUNDUP WEATHERMAX, 0.4% PMIDA) (Table 2E). Composition 539, the 0.06% PMIDA and no iron composition, also was effective in minimizing necrosis. A graphical representation of the data is shown in FIG. 9.

TABLE 2E

T-Test Pairwise Mean Comparisons For 5 Experiments
Compositions compared to 902 as a Standard

| Standard | Composition | % Difference In Necrosis | Significance | n |
|---|---|---|---|---|
| 902 | 825 | −1.4 | ‡ | 60 |
| 902 | 742 | 11.4 | + | 60 |
| 902 | 817 | 12.0 | + | 60 |
| 902 | 737 | 12.4 | + | 60 |
| 902 | 745 | 13.4 | + | 60 |
| 902 | 539 | 13.9 | + | 60 |
| 902 | 747 | 14.2 | + | 60 |

‡ Composition shows significantly more necrosis than Standard ($p < 0.01$)
+ Composition shows significantly less necrosis than Standard ($p < 0.01$)

Example 3

Analytical Procedure

N-(phosphonomethyl)iminodiacetic acid (PMIDA) levels were determined using a high-pressure liquid chromatography (HPLC) procedure. Separation was performed on a pre-column (5 μm, Zorbax SB-C18 Analytical Guard Column, 4.6×12.5 mm) and analytical column (5 μm, Zorbax SAX-300, 150 mm×4.6 mm ID) with an isocratic solvent system of 100 mM $KH_2PO_4$ with the pH adjusted to 2.0 with concentrated phosphoric acid or an alternative isocratic solvent system of 54.4 g $KH_2PO_4$, 4 g concentrated sulfuric acid and 22 mL concentrated phosphoric acid diluted to 4 L with HPLC grade water. Flow rate was 0.70 mL/min. Post-column reagent (3.2 mM $CuSO_4$, 0.70 mL/min) was added to the column eluate just prior to an in-line reaction coil [PTFE tubing, 8 ft.×1/32 in. ID (1/16 in. OD)] installed before the UV detector which produced a copper-PMIDA chromophore that was quantified at 250 nm.

A stock solution of 0.2000 wt. % PMIDA was prepared in HPLC grade water. The working solutions of 0.0020, 0.0050, 0.0080, and 0.0100 wt. % PMIDA were prepared by appropriate dilution of the stock solution in HPLC grade water, were stored at 4° C. and replaced with fresh working solutions every 2 months. A calibration curve was constructed from the working solutions for each set of samples analyzed. Samples were prepared by weighing to four significant figures and diluted with HPLC grade water to give a sample solution containing between 0.0020 to 0.0100 wt. % PMIDA. For both the working solutions and the sample solutions, 50 μL was injected in the chromatographic system.

Figure 10:
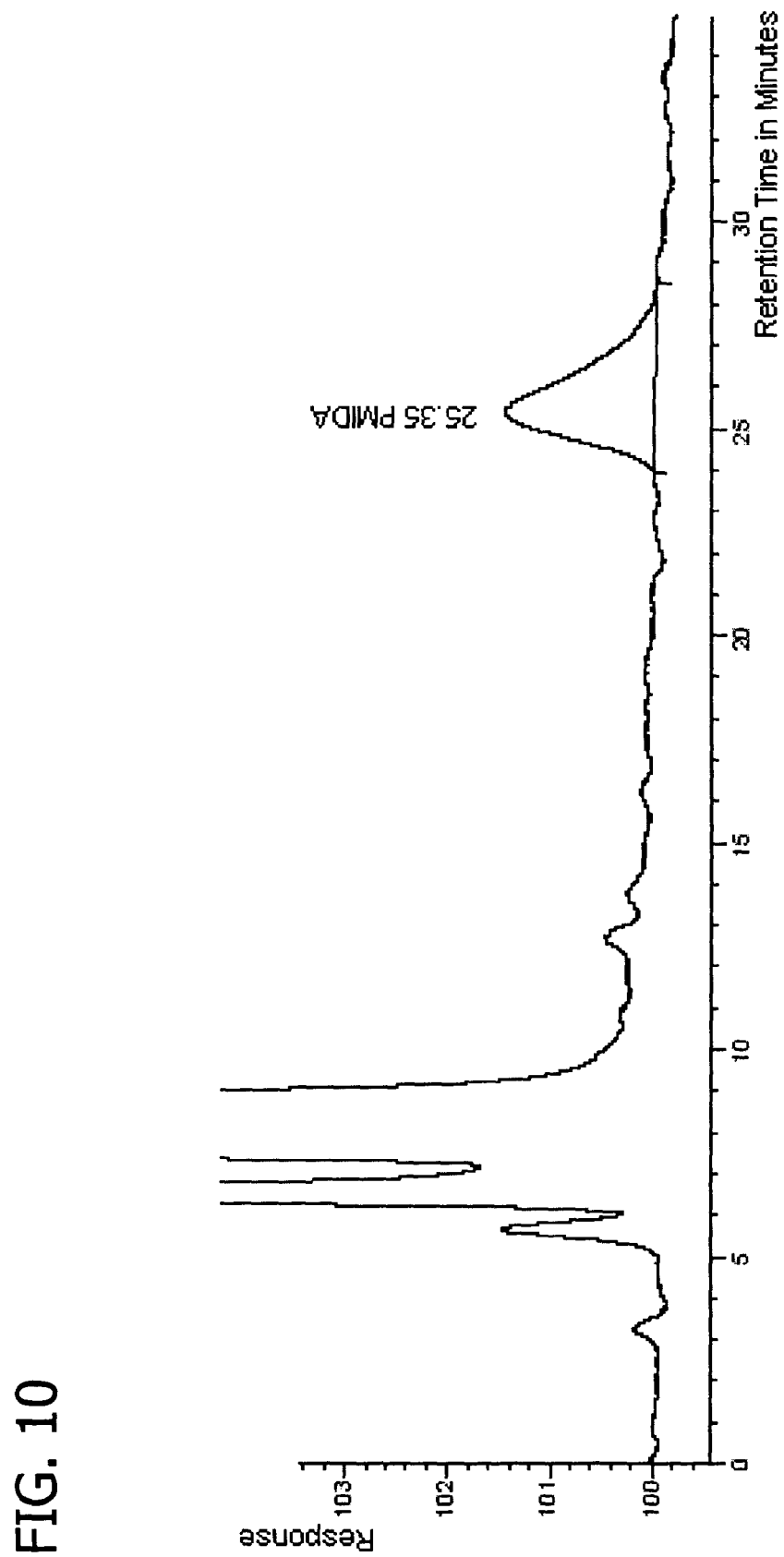
FIG. 10 is the chromatogram (first isocratic solvent system) for an iron-containing glyphosate formulation concentrate subjected to the high-pressure liquid chromatography analytical procedure of Example 3 to determine the concentration of PMIDA in the formulation concentrate.

First Isocratic Solvent System: The chromatogram for an iron-containing glyphosate formulation concentrate sample diluted 20 fold with deionized water is shown in FIG. 10. The concentration of PMIDA in the analyzed sample solution was 0.0021 wt. % PMIDA, which corresponded to a concentration of 0.0437 wt. % PMIDA in the glyphosate formulation concentrate.

Figure 11:
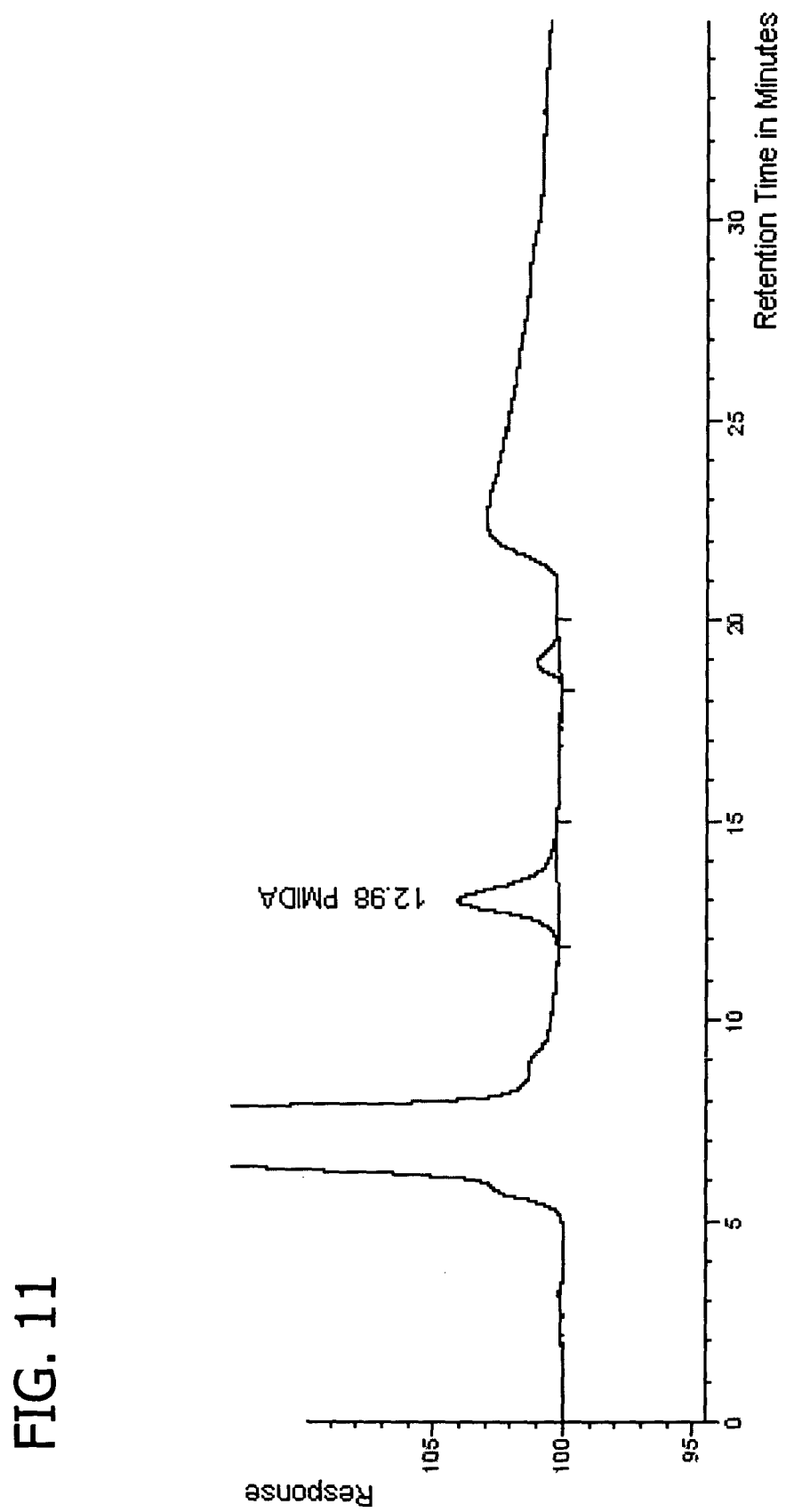
FIG. 11 is the chromatogram (alternative isocratic solvent system) for an iron-containing formulation concentrate subjected to the high-pressure liquid chromatography analytical procedure of Example 3 to determine the concentration of PMIDA in the formulation concentrate.

Alternative Isocratic Solvent System: The chromatogram for an iron-containing formulation concentrate sample diluted 20 fold with HPLC grade water is shown in FIG. 11. The concentration of PMIDA in the analyzed sample solution was 0.0025 wt. % PMIDA, which corresponded to a concentration of 0.0519 wt. % PMIDA in the glyphosate formulation concentrate.

The analytical method set forth in this Example is particularly advantageous in that it can accurately assess PMIDA content of materials containing appreciable quantities of one or more metal ions such as iron used as a safening agent in accordance with the present invention.

In view of the above, it will be seen that the several objects of the invention are achieved and other advantageous results attained.

As various changes could be made in the above methods without departing from the scope of the invention, it is intended that all matter contained in the above description or shown in the accompanying drawings shall be interpreted as illustrative and not in a limiting sense.

When introducing elements of the present invention or the preferred embodiments thereof, the articles "a", "an", "the", and "said" are intended to mean that there are one or more of the elements. The terms "comprising", "including," and "having" are intended to be inclusive and mean that there may be additional elements other than the listed elements.

What is claimed:

1. A method for selectively controlling weeds in a field containing a crop of transgenic glyphosate-tolerant cotton plants having increased glyphosate tolerance in vegetative and reproductive tissues, the method comprising:

when at least five leaf nodes are present on a cotton plant of said crop, applying to foliage of said crop and weeds a sufficient amount of a herbicidal glyphosate formulation comprising N-(phosphonomethyl)glycine or an agronomically acceptable salt thereof to control growth of said weeds without incurring significant glyphosate-mediated reproductive injury to said plant of said crop; and controlling the concentration of N-(phosphonomethyl)iminodiacetic acid and salts thereof present in the herbicidal glyphosate formulation and the application rate of the herbicidal glyphosate formulation to said crop and weeds in said field such that the application rate of N-(phosphonomethyl)iminodiacetic acid and salts thereof is no more than about 2.5 g of N-(phosphonomethyl)iminodiacetic acid equivalent/hectare so as to not induce significant leaf necrosis in said cotton plants of said crop.

2. A method for selectively controlling weeds in a field containing a crop of transgenic glyphosate-tolerant cotton plants having increased glyphosate tolerance in vegetative and reproductive tissues, the method comprising:

when at least five leaf nodes are present on a cotton plant of said crop, applying to the foliage of said crop and weeds a sufficient amount of a herbicidal glyphosate formulation to control growth of said weeds without incurring significant glyphosate-mediated reproductive injury to said plant of said crop, the herbicidal glyphosate formulation comprising N-(phosphonomethyl)glycine or an agronomically acceptable salt thereof, N-(phosphonomethyl)iminodiacetic acid or salt thereof and a safening agent in a concentration sufficient to inhibit significant leaf necrosis in said crop induced by N-(phosphonomethyl)iminodiacetic acid or salt thereof present in the herbicidal glyphosate formulation, wherein said safening agent is selected from the group consisting of metal ions, antioxidants, humectants, light absorbing compounds, and mixtures thereof.

3. The method of claim 1 or 2 wherein the herbicidal glyphosate formulation is applied to said crop and weeds in said field when at least one reproductive node is present on the plant of said crop.

4. The method of claim 1 or 2 wherein the herbicidal glyphosate formulation is applied to said crop and weeds in said field when ten or more leaf nodes are present on the plant of said crop.

5. The method of claim 1 or 2 wherein the herbicidal glyphosate formulation is applied to said crop and weeds in said field up to and including layby of said crop of transgenic glyphosate-tolerant cotton plants.

6. The method of claim 1 or 2 wherein the herbicidal glyphosate formulation is applied to said crop and weeds in said field when six or more leaf nodes and no more than fourteen leaf nodes are present on the plant of said crop.

7. The method of claim 1 or 2 wherein glyphosate-mediated reproductive injury to said plant of said crop is quantified by flower pollen shed and/or lint yield.

8. The method of claim 7 wherein said plant of said crop exhibits a flower pollen shed comparable to that of a transgenic glyphosate-tolerant cotton plant in the absence of foliar application of a herbicidal glyphosate formulation after the four leaf node stage.

9. The method of claim 7 wherein said plant of said crop exhibits a lint yield comparable to that of a transgenic glyphosate-tolerant cotton plant in the absence of foliar application of a herbicidal glyphosate formulation after the four leaf node stage.

10. The method of claim 1 or 2 wherein leaf necrosis in said crop is quantified by the area of necrotic lesions on the surface of the leaves of said plants of said crop and wherein necrotic lesions on the surface of the leaves of said plants of said crop on average account for no more than about 5% of the total leaf area of said plants of said crop.

11. The method of claim 2 wherein said safening agent inhibits significant leaf necrosis in said crop induced by N-(phosphonomethyl)iminodiacetic acid or salt thereof present in the herbicidal glyphosate formulation by inhibiting buildup of phytotoxic free radicals in said plants of said crop.

12. The method of claim 2 wherein said safening agent comprises a metal ion that is subject to formation of a complex or salt with N-(phosphonomethyl)iminodiacetic acid or an anion formed by deprotonation or partial deprotonation thereof, the formation of such complex or salt being effective to inhibit significant leaf necrosis in said crop of transgenic glyphosate-tolerant cotton plants induced by N-(phosphonomethyl)iminodiacetic acid or salt thereof present in said herbicidal glyphosate formulation.

13. The method of claim 12 wherein the metal ion is polyvalent.

14. The method of claim 12 wherein the metal ion is a transition metal ion.

15. The method of claim 12 wherein the metal ion is selected from the group consisting of aluminum, antimony, iron, chromium, nickel, manganese, cobalt, copper, zinc, vanadium, titanium, molybdenum, tin, barium and mixtures thereof.

16. The method of claim 15 wherein the metal ion is selected from the group consisting of aluminum, copper, iron, zinc and mixtures thereof.

17. The method of claim 16 wherein the safening agent comprises a mixture of iron and zinc metal ions or a mixture of iron and copper metal ions.

18. The method of claim 2 wherein the concentration of N-(phosphonomethyl)iminodiacetic acid and salts thereof present in the herbicidal glyphosate formulation and the application rate of the herbicidal glyphosate formulation to said crop and weeds in said field is such that the application rate of N-(phosphonomethyl)iminodiacetic acid and salts thereof is greater than about 2.5 g of N-(phosphonomethyl)iminodiacetic acid equivalent/hectare.

19. The method of claim 1 wherein the concentration of N-(phosphonomethyl)iminodiacetic acid and salts thereof present in the herbicidal glyphosate formulation and the application rate of the herbicidal glyphosate formulation to said crop and weeds in said field are controlled such that the application rate of N-(phosphonomethyl)iminodiacetic acid and salts thereof is no more than about 1.5 g of N-(phosphonomethyl)iminodiacetic acid equivalent/hectare.

20. The method of claim 1 or 2 wherein the genome of the transgenic glyphosate-tolerant cotton plants comprises one or more DNA molecules selected from the group consisting of SEQ ID NO:1, SEQ ID NO:2, SEQ ID NO:3, and SEQ ID NO:4; or the genome of the transgenic glyphosate-tolerant cotton plants in a DNA amplification method produces an amplicon comprising SEQ ID NO:1 or SEQ ID NO:2; or the transgenic glyphosate-tolerant cotton plants comprise a glyphosate tolerant trait that is genetically linked to a complement of a marker polynucleic acid, and the marker polynucleic acid molecule is homologous or complementary to a DNA molecule selected from the group consisting of SEQ ID NO:1 and SEQ ID NO:2.

21. The method of claim 1 or 2 wherein the crop of transgenic glyphosate-tolerant cotton plants comprises cotton plants grown from seed of cotton event designated MON 88913 and having representative seed deposited with American Type Culture Collection (ATCC) with Accession No. PTA-4854 or glyphosate-tolerant progeny thereof.

22. The method of claim 1 or 2 wherein the herbicidal glyphosate formulation is applied to said crop and weeds in said field when six or more leaf nodes and no more than eighteen leaf nodes are present on the plant of said crop.

23. The method of claim 1 or 2 wherein the herbicidal glyphosate formulation is applied to said crop and weeds in said field when six or more leaf nodes and no more than twenty leaf nodes are present on the plant of said crop.

24. The method of claim 19 wherein the concentration of N-(phosphonomethyl)iminodiacetic acid and salts thereof present in the herbicidal glyphosate formulation and the application rate of the herbicidal glyphosate formulation to said crop and weeds in said field are controlled such that the application rate of N-(phosphonomethyl)iminodiacetic acid and salts thereof is no more than about 1.2 g of N-(phosphonomethyl)iminodiacetic acid equivalent/hectare.

25. The method of claim 24 wherein the concentration of N-(phosphonomethyl)iminodiacetic acid and salts thereof present in the herbicidal glyphosate formulation and the application rate of the herbicidal glyphosate formulation to said crop and weeds in said field are controlled such that the application rate of N-(phosphonomethyl)iminodiacetic acid and salts thereof is no more than about 1 g of N-(phosphonomethyl)iminodiacetic acid equivalent/hectare.

26. The method of claim 25 wherein the concentration of N-(phosphonomethyl)iminodiacetic acid and salts thereof present in the herbicidal glyphosate formulation and the application rate of the herbicidal glyphosate formulation to said crop and weeds in said field are controlled such that the application rate of N-(phosphonomethyl)iminodiacetic acid and salts thereof is no more than about 0.7 g of N-(phosphonomethyl)iminodiacetic acid equivalent/hectare.

27. The method of claim 26 wherein the concentration of N-(phosphonomethyl)iminodiacetic acid and salts thereof present in the herbicidal glyphosate formulation and the application rate of the herbicidal glyphosate formulation to said crop and weeds in said field are controlled such that the application rate of N-(phosphonomethyl)iminodiacetic acid and salts thereof is no more than about 0.5 g of N-(phosphonomethyl)iminodiacetic acid equivalent/hectare.

28. The method of claim 27 wherein the concentration of N-(phosphonomethyl)iminodiacetic acid and salts thereof present in the herbicidal glyphosate formulation and the application rate of the herbicidal glyphosate formulation to said crop and weeds in said field are controlled such that the application rate of N-(phosphonomethyl)iminodiacetic acid and salts thereof is no more than about 0.25 g of N-(phosphonomethyl)iminodiacetic acid equivalent/hectare.

29. The method of claim 2 wherein the safening agent comprises an antioxidant.

30. The method of claim 29 wherein the antioxidant is selected from the group consisting of hydroquinone, resorcinol, BHA, BHT, and mixtures thereof.

31. The method of claim 29 or 30 wherein the molar ratio of antioxidant to N-(phosphonomethyl)iminodiacetic acid equivalent is from about 50:1 to about 1:1.

32. The method of claim 2 wherein the safening agent comprises a humectant.

33. The method of claim 32 wherein the humectant is hygroscopic and substantially non-ionizable in water.

34. The method of claim 33 wherein the humectant comprises a polyhydroxy alcohol.

35. The method of claim 34 wherein the humectant is selected from the group consisting of sorbitol, xylitol, inositol, mannitol, pantothenol, glycerol, and derivatives and mixtures thereof.

36. The method of any one of claims 32 to 35 wherein the molar ratio of humectant to N-(phosphonomethyl)iminodiacetic acid equivalent is from about 250:1 to about 1:1.

37. The method of claim 2 wherein the safening agent comprises a light absorbing compound.

38. The method of claim 37 wherein the light absorbing compound comprises a dye.

39. The method of claim 38 wherein the light absorbing compound comprises 3-carboxy-5-hydroxy-1-psulfophenyl-4-p-sulfophenylazopyrazole trisodium salt.

* * * * *

UNITED STATES PATENT AND TRADEMARK OFFICE
CERTIFICATE OF CORRECTION

PATENT NO. : 8,129,564 B2  
APPLICATION NO. : 11/368344  
DATED : March 6, 2012  
INVENTOR(S) : Stephen D. Prosch et al.

Page 1 of 1

It is certified that error appears in the above-identified patent and that said Letters Patent is hereby corrected as shown below:

On the title page, Item 75 Inventors:
"Stephen D. Prosch, Ballwin, MO (US); Michael E. Seitz, Dublin, CA (US); Eric A. Haupfear, St. Charles, MO (US); Eduardo Casanova, Chesterfield, MO (US); Peter E. Rogers, St. Louis, MO (US); David R. Eaton, St. Louis, MO (US); David Z. Becher, St. Louis, MO (US)"

Should read
-- Stephen D. Prosch, Ballwin, MO (US); Michael E. Seitz, Dublin, CA (US); David R. Eaton, St. Louis, MO (US); David Z. Becher, St. Louis, MO (US) --

Signed and Sealed this
Twelfth Day of February, 2013

Teresa Stanek Rea
*Acting Director of the United States Patent and Trademark Office*

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Chimeric DNA of cotton genomic DNA and
      transgene insert DNA

<400> SEQUENCE: 1
attcaatgta gtcaaacact                                                    20

<210> SEQ ID NO 2
<211> LENGTH: 20
<212> TYPE: DNA
<213> ORGANISM: Artificial Sequence
<220> FEATURE:
<223> OTHER INFORMATION: Chimeric DNA of cotton genomic DNA and
      transgene insert DNA

<400> SEQUENCE: 2
ttgaatatat attacaaagc                                                    20

<210> SEQ ID NO 3
<211> LENGTH: 2880
<212> TYPE: DNA
<213> ORGANISM: Artificial sequence
<220> FEATURE:
<223> OTHER INFORMATION: Chimeric DNA of cotton genomic DNA and
      transgene insert DNA

<400> SEQUENCE: 3
gcttggtacc gagctcggat ccactagtaa cggccgccag tgtgctggaa ttcgcccttt         60
tttactacga tgttaagtcc tattttacac agtttctttta agacagattt gaccgctcct      120
acgatacttg gagaaacgtt ggtcgaatgt ctcttagaat acaacaacac gatgatcaaa      180
gcagtagcac ctctgtagtg attaacgaac aagcgttgtc ttttctatc accaaaacat      240 tggaaaacat ggagaggaaa agagtagaat tttggaaaga aaataatctt ggtatgagag      300
agtgagattg agcaaaaaat tttgaagagg tcttagcctt ttatatgcgt tcaaagtgga      360
ggaattttgg aaatatccat gtataatgag acaaaatctg catttaaaat ggcatttcgc      420
gtcgcctgcg tcgtgcgagt gcgccccaac cctgacgggt ttggacttac accctcatac      480
acgcgaggca ggattccaag tttagtcatt caatcactct taaagtgagc ttcaagctta      540
gacattacaa attaaattaa ataatataag ataattgcgc taaataaaca aacatttttt      600
ttgtgatcct gaacgtaatc aacgagggta tgatggttat gattcacgga aagagcgaga      660
```

-continued

```
gaagagaacc gtcgctcgaa gaggatgatg attcatccta ttcatgcacg actgtccaac    720
tccccaccca atcaaattcc aaattatgac atgagaagaa catcatccca cgtggtctgt    780
gcttcacgcc accatgtccc acgtgggctc cattttggtg gggcccttcc ccaccgccca    840
agctgatccc gggttggcca tccctacttt taattatcag agccacctcc caatctgca     900 aaacgacgga aatggaaaac tataattttc ttttttttca acgtacttat aaaatatttt    960
tcaaaaaagt atgaataaaa ttgtgatatt gcttggccta agaggccaat cttttgcaaa   1020
tctcgaagtc gggaggcaca ataaaaactt ggaaagtttt ttcaagtgtc tgctttataa   1080
aattattgaa atgcatgtat tcgtacttgc cttatttatc gacaatttaa acattattat   1140
ttcatgaaaa tgtccttcca ccgatttcaa tgacaaaacc aataattact actttttatt   1200
ttcaattatg tcacggttca catgtttatt agggtttagg ttgaggttaa aacttttcgac  1260 tctctattcg taacgcttaa agatgtaggg tttaggttga ggttaaaaca atcatgtaat   1320
gtaaggatac ctgaaaagct gtcattagtg taagtgttta ttactagggt tgtttaaatt   1380
catgttgatg tcaagcttgg ataacccatt ttactaaaaa aataaatgaa gtcccaaagg   1440
gcattgggca tcctatcaaa gatgggaaat ttttcaaaa ttttaaccta aaaagaggt     1500 ggaaagtctt agtccaaata atcagccaca tcagaatttg attcgtttct ttcaagcaaa   1560
ttatacctat tggctgcaat atctttaagt ggaatggtcg gccaaacttt tccatatcag   1620
cttgattcat ctctaaactt gattattctt ttttattaat attaaattcc acaacttgaa   1680 cttttaatttt tttaattaat taaaaaaatt gtcacctttt caagctgaaa aagaaaaaga  1740
aaccttaatt attatcacta gtattaaatt tcaaaacttg atttgtccta aatttgaaaa   1800
ggggtctcct tcaattcata tatgtagtca tgaagattat aacttagctg aaaatggcct   1860
ccattatttg gcttattcaa tcaaaagttt acaaaactag tgcaaattta atatgataat   1920
gtctacaaga accaaatacg aattgagtaa attttttttgg ctaaaataaa ttacgaattg   1980
atgaattatc attttaaaaa gttctttttta accatttctt ttactgaatt aaaaaaaggt   2040
tttattaatc atatatatta caaattaccc attaagtagc caaattacaa atttttaattc  2100 aatgtagtca aacactgata gtttaaacat gactctctta aggtagccaa agcccgggct   2160
taattaaggc gcgccggcca agtcggccgc ggccgcgtta tcaagcttct gcaggtcctg   2220
ctcgagtgga agctaattct cagtccaaag cctcaacaag gtcagggtac agagtctcca   2280
aaccattagc caaaagctac aggagatcaa tgaagaatct tcaatcaaag taaactactg   2340
ttccagcaca tgcatcatgg tcagtaagtt tcagaaaaag acatccaccg aagacttaaa   2400
gttagtgggc atctttgaaa gtaatcttgt caacatcgag cagctggctt gtggggacca   2460
gacaaaaaag gaatggtgca gaattgttag gcgcacctac caaaagcatc tttgccttta   2520
ttgcaaagat aaagcagatt cctctagtac aagtggggaa caaaataacg tggaaaagag   2580
ctgtcctgac agcccactca ctaatgcgta tgacgaacgc agtgacgacc acaaaagaat   2640
tagcttgagc tcaggattta gcagcattcc agattgggtt caatcaacaa ggtacgagcc   2700
atatcacttt attcaaattg gtatcgccaa aaccaagaag gaactcccat cctcaaaggt   2760
ttgtaaggaa gaattcgata tcaagcttga tatcggaagt ttctctcttg agggaggttg   2820
ctcgtggaat gggacacata tggttgttat aataaaccat ttccattgtc atgagatttt   2880
```

<210> SEQ ID NO 4
<211> LENGTH: 1675
<212> TYPE: DNA
<213> ORGANISM: Artificial sequence

```
<220> FEATURE:
<223> OTHER INFORMATION: Chimeric DNA of cotton genomic DNA and
      transgene insert DNA

<400> SEQUENCE: 4
tgaccgaagt taatatgagg agtaaaacac ttgtagttgt accattatgc ttattcacta      60
ggcaacaaat atattttcag acctagaaaa gctgcaaatg ttactgaata caagtatgtc     120
ctcttgtgtt ttagacattt atgaactttc ctttatgtaa ttttccagaa tccttgtcag     180
attctaatca ttgctttata attatagtta tactcatgga tttgtagttg agtatgaaaa     240
tattttttaa tgcattttat gacttgccaa ttgattgaca acatgcatca atcgacctgc     300
agccactcga gtggaggcct catctaagcc cccatttgga cgtgaatgta gacacgtcga     360
aataaagatt tccgaattag aataatttgt ttattgcttt cgcctataaa tacgacggat     420
cgtaatttgt cgtttttatca aaatgtactt tcattttata ataacgctgc ggacatctac     480
attttgaat tgaaaaaaaa ttggtaatta ctctttcttt ttctccatat tgaccatcat     540
actcattgct gatccatgta gatttcccgg acatgaagcc atttacaatt gaatatatat     600
tacaaagcta tttgcttata acatatgcga aaaattttgt actataatca ggggtaaatt     660
taggaggggg cttgtaggtc tcgcttctct taaaatgaaa aattttctat ttagttattt     720
aaaattttaa aagtaaaata taaaaatttc atttaatcct ttaaaaatta taaagatata     780
gactattaaa atgatgaaat tacaattta ttatcataaa aattataatt taatttcgac     840
ccctaacaaa attttctgat tttgcccca actgtaatat ttgtataaaa acattttctt     900
tttgcattta atgatttctt taattcagtc caagaaagaa atttattaat tgcatatgcg     960
aaagttagtc cttgcctagt gatattaaag gaaagaaaca taaatcaat aaattaattt    1020
ttaaagcaaa tagtaaaaat aaggaaaaac tttctacgat agtctataat tcaaaaaaag    1080
aaataataat ctttaaccat tgaattttaa aataacatca gaataatcta tttatttaat    1140
ttaataaata ataataacat atatattaat attaaaattt ttattgagct tagtgtcaca    1200
aatcaataaa aaatttctta caaaataaat tatattattt tgagggtgtt ttattatttt    1260
atatatttta tacagacata tagaaatata aatacacata ataaaatttg aatccaaatt    1320
tttaattttt aacatttata atttactatt caaccaaaat tttatttatt atttatatca    1380
aattttata aatatattta tcagataatg cgattttttt tacctatata tagatgacat    1440
aatctacttt aaattaagtc ctaaaaataa tatatcatac caaaaaaatt cttaaaatga    1500
atctgataat acttaacccc tttataaaa caatcttaac cccttatata ttttaatatt    1560
aatatcatta taaatataaa tctattgagc atatgtttta aaccaagtaa tgttgagtgc    1620
ggtagtaaaa ctcattacac attttaagta gaacgtagtt cgaaccttgg agaag         1675
```